(12) United States Patent
Glerum et al.

(10) Patent No.: US 12,023,260 B2
(45) Date of Patent: *Jul. 2, 2024

(54) EXPANDABLE FUSION DEVICE AND METHOD OF INSTALLATION THEREOF

(71) Applicant: GLOBUS MEDICAL, INC., Audubon, PA (US)

(72) Inventors: Chad Glerum, Pennsburg, PA (US); Andrew Iott, Newtown Square, PA (US); Mark Weiman, Downingtown, PA (US); Jody Seifert, Birdsboro, PA (US); Kevin Gahman, Douglassville, PA (US); Colm McLaughlin, Glenside, PA (US); Adam Friedrich, Cinnaminson, NJ (US)

(73) Assignee: Globus Medical, Inc, Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/302,229

(22) Filed: Apr. 18, 2023

(65) Prior Publication Data

US 2023/0338164 A1 Oct. 26, 2023

Related U.S. Application Data

(63) Continuation of application No. 17/388,220, filed on Jul. 29, 2021, now Pat. No. 11,666,457, which is a (Continued)

(51) Int. Cl.
*A61F 2/44* (2006.01)
*A61F 2/46* (2006.01)
*A61F 2/30* (2006.01)

(52) U.S. Cl.
CPC ............ *A61F 2/4611* (2013.01); *A61F 2/447* (2013.01); *A61F 2002/30169* (2013.01); (Continued)

(58) Field of Classification Search
CPC .......... A61F 2/44; A61F 2/442; A61F 2/4684; A61F 2002/30168; A61F 2002/30207; (Continued)

(56) References Cited

U.S. PATENT DOCUMENTS 4,349,921 A 9/1982 Kuntz
4,599,086 A 7/1986 Doty
(Continued)

FOREIGN PATENT DOCUMENTS

CA 2088066 A1 1/1992
DE 4012622 C1 7/1991
(Continued)

*Primary Examiner* — Jessica Weiss

(57) ABSTRACT

The present invention provides an expandable fusion device capable of being installed inside an intervertebral disc space to maintain normal disc spacing and restore spinal stability, thereby facilitating an intervertebral fusion. In one embodiment, the fusion device includes a body portion, a first endplate, and a second endplate, the first and second endplates capable of being moved in a direction away from the body portion into an expanded configuration or capable of being moved towards the body portion into an unexpanded configuration. The fusion device is capable of being deployed and installed in both configurations.

17 Claims, 68 Drawing Sheets

Related U.S. Application Data continuation of application No. 16/405,234, filed on May 7, 2019, now Pat. No. 11,103,366, which is a continuation of application No. 14/485,041, filed on Sep. 12, 2014, now Pat. No. 10,327,917, which is a continuation-in-part of application No. 13/845,645, filed on Apr. 3, 2013, now Pat. No. 9,216,095, which is a continuation-in-part of application No. 13/451,230, filed on Apr. 19, 2012, now Pat. No. 8,518,120, which is a continuation of application No. 13/440,158, filed on Apr. 5, 2012, now Pat. No. 8,679,183, which is a continuation-in-part of application No. 13/273,994, filed on Oct. 14, 2011, now Pat. No. 9,358,126, and a continuation-in-part of application No. 12/823,736, filed on Jun. 25, 2010, now Pat. No. 8,685,098, said application No. 13/273,994 is a continuation of application No. 12/579,833, filed on Oct. 15, 2009, now Pat. No. 8,062,375.

(60) Provisional application No. 61/877,034, filed on Sep. 12, 2013.

(52) U.S. Cl.
CPC ........... *A61F 2002/30207* (2013.01); *A61F 2002/3021* (2013.01); *A61F 2002/30265* (2013.01); *A61F 2002/30365* (2013.01); *A61F 2002/30367* (2013.01); *A61F 2002/30372* (2013.01); *A61F 2002/30373* (2013.01); *A61F 2002/30387* (2013.01); *A61F 2002/30405* (2013.01); *A61F 2002/30471* (2013.01); *A61F 2002/30482* (2013.01); *A61F 2002/30484* (2013.01); *A61F 2002/30487* (2013.01); *A61F 2002/30492* (2013.01); *A61F 2002/30495* (2013.01); *A61F 2002/30507* (2013.01); *A61F 2002/30517* (2013.01); *A61F 2002/3052* (2013.01); *A61F 2002/30523* (2013.01); *A61F 2002/30538* (2013.01); *A61F 2002/3055* (2013.01); *A61F 2002/30556* (2013.01); *A61F 2002/30578* (2013.01); *A61F 2002/30579* (2013.01); *A61F 2002/30593* (2013.01); *A61F 2002/30594* (2013.01); *A61F 2002/30601* (2013.01); *A61F 2002/30604* (2013.01); *A61F 2002/30841* (2013.01); *A61F 2002/30904* (2013.01); *A61F 2/4603* (2013.01); *A61F 2002/4627* (2013.01); *A61F 2/4684* (2013.01); *A61F 2310/00017* (2013.01); *A61F 2310/00023* (2013.01); *A61F 2310/00179* (2013.01)

(58) Field of Classification Search
CPC .... A61F 2002/3021; A61F 2002/30265; A61F 2002/30365; A61F 2002/30367; A61F 2002/30372; A61F 2002/30373; A61F 2002/30387; A61F 2002/30405; A61F 2002/30471; A61F 2002/30482; A61F 2002/30484
USPC ................ 623/17.11–17.16; 600/99–100
See application file for complete search history.

(56) References Cited

U.S. PATENT DOCUMENTS

| | | |
|---|---|---|
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 * | 1/2001 | Biedermann ........... A61F 2/447 623/17.11 |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 * | 12/2004 | Erickson ................ A61F 2/446 623/17.15 |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 * | 7/2006 | Lim ...................... A61F 2/442 623/17.16 |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,628,577 B1 * | 1/2014 | Jimenez et al. ......... A61F 2/44 623/17.16 |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | JImenez et al. |

(56) References Cited

U.S. PATENT DOCUMENTS

| | | |
|---|---|---|
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | JImenez et al. |
| 9,532,883 B2 | 1/2017 | McLuen et al. |
| 9,622,878 B2 | 4/2017 | Grotz |
| 9,700,425 B1* | 7/2017 | Smith .................... A61F 2/4637 |
| 9,801,734 B1* | 10/2017 | Stein ...................... A61F 2/447 |
| 11,103,366 B2* | 8/2021 | Glerum ................. A61F 2/4611 |
| 2002/0045945 A1 | 4/2002 | Liu |
| 2002/0068976 A1 | 6/2002 | Jackson |
| 2002/0068977 A1 | 6/2002 | Jackson |
| 2003/0176926 A1 | 9/2003 | Boehm et al. |
| 2004/0030387 A1 | 2/2004 | Landry et al. |
| 2004/0049271 A1 | 3/2004 | Biedermann |
| 2004/0054412 A1 | 3/2004 | Gerbec et al. |
| 2004/0087947 A1* | 5/2004 | Lim ....................... A61F 2/4465 |
| | | 606/279 |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1* | 7/2010 | Greenhalgh ............ A61F 2/44 |
| | | 623/17.11 |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2010/0292796 A1* | 11/2010 | Greenhalgh ....... A61B 17/8858 |
| | | 623/17.11 |
| 2010/0305705 A1* | 12/2010 | Butler ..................... A61F 2/447 |
| | | 623/17.11 |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1* | 6/2016 | McClintock ............ A61F 2/446 |
| | | 623/17.16 |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 | 12/2000 |
| FR | 2794968 A1 | 12/2000 |
| JP | 2000-513263 | 10/2000 |
| JP | 2000-513263 A | 10/2000 |
| JP | 2000513263 A | 10/2000 |
| JP | 2013508031 A | 3/2013 |
| KR | 200290058 Y1 | 9/2002 |
| SU | 1424826 A1 | 9/1988 |

(56) References Cited

FOREIGN PATENT DOCUMENTS

| | | | |
|---|---|---|---|
| WO | 9201428 | A1 | 2/1992 |
| WO | 9525485 | A1 | 9/1995 |
| WO | 199942062 | A1 | 8/1999 |
| WO | 1999042062 | A1 | 8/1999 |
| WO | 199966867 | A1 | 12/1999 |
| WO | 1999066867 | A1 | 12/1999 |
| WO | 2002045625 | A1 | 6/2002 |
| WO | 2004019829 | A1 | 3/2004 |
| WO | 2004069033 | A2 | 8/2004 |
| WO | 2006045094 | A2 | 4/2006 |
| WO | 2006047587 | A2 | 5/2006 |
| WO | 2006113080 | A2 | 10/2006 |
| WO | 2008044057 | A1 | 4/2008 |
| WO | 2008134515 | A1 | 11/2008 |
| WO | 2009114381 | A1 | 9/2009 |
| WO | 2010103344 | A1 | 9/2010 |
| WO | 2012031267 | A1 | 3/2012 |
| WO | 2015009793 | A1 | 1/2015 |

\* cited by examiner

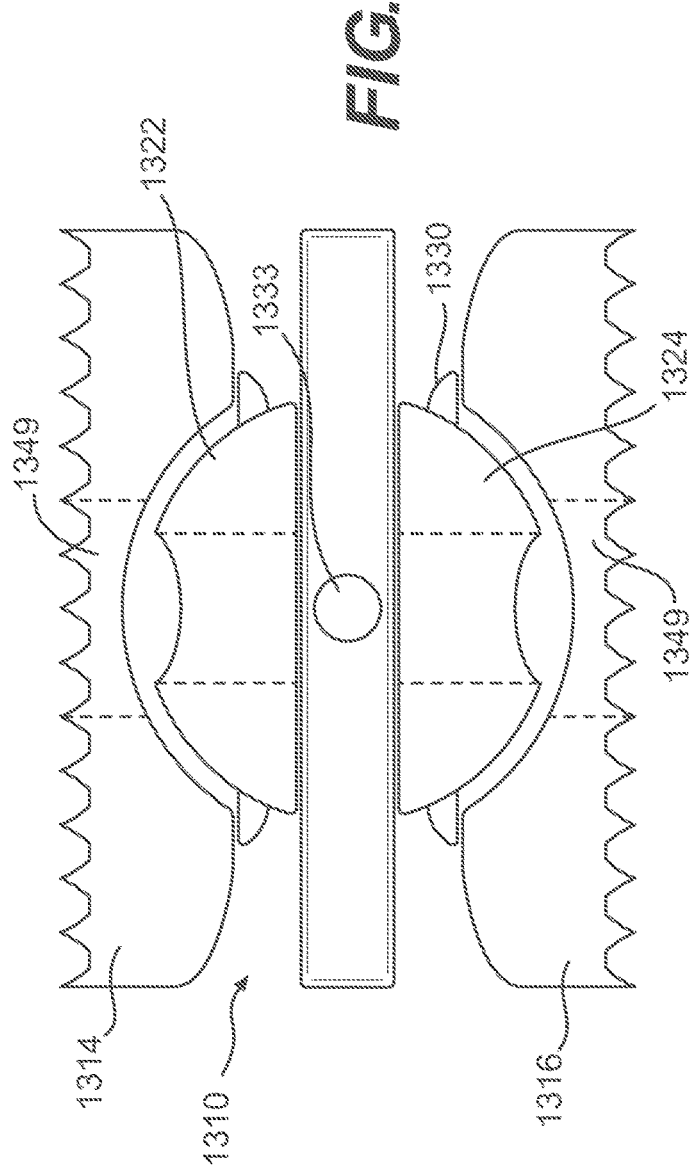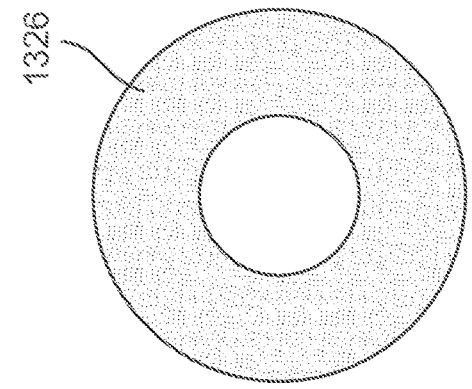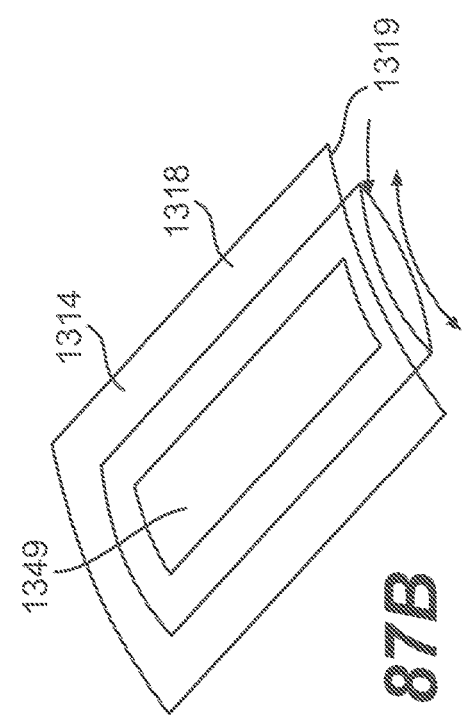

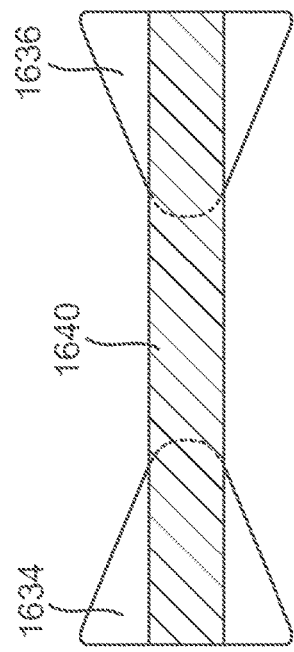
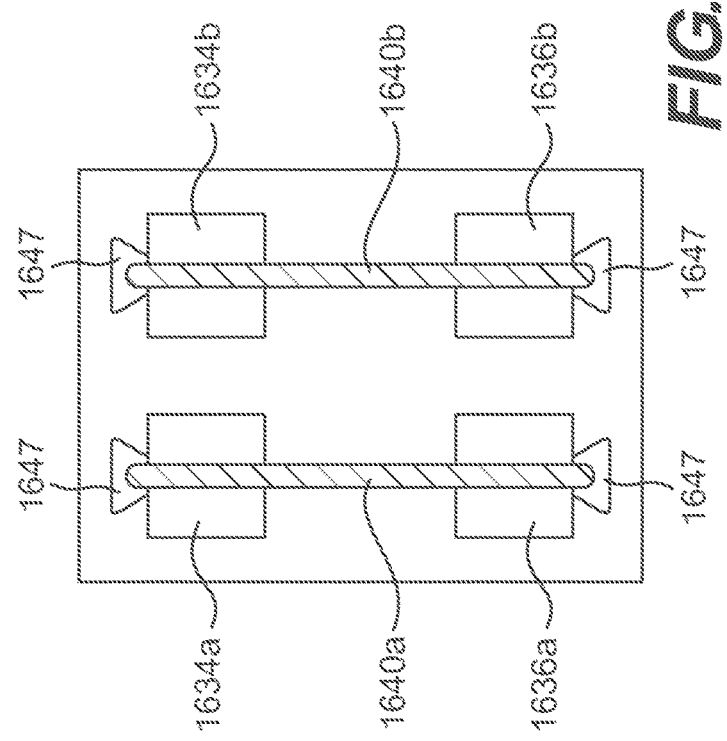
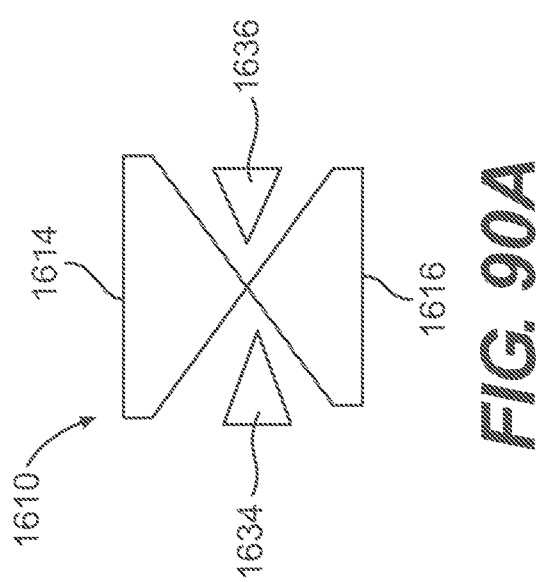

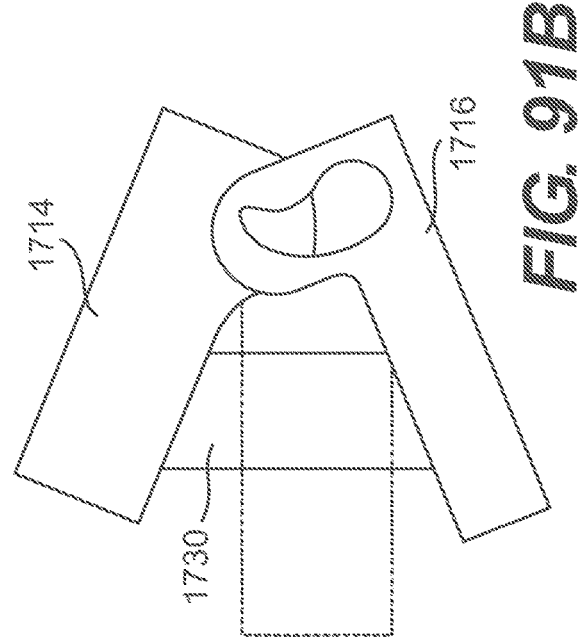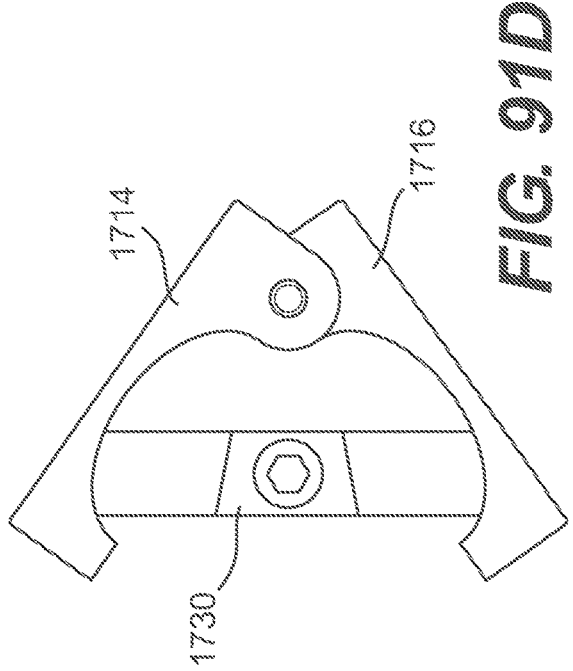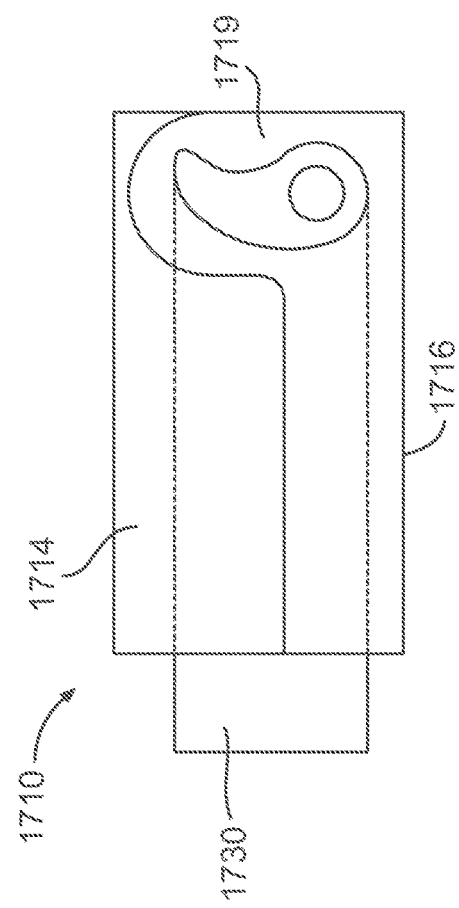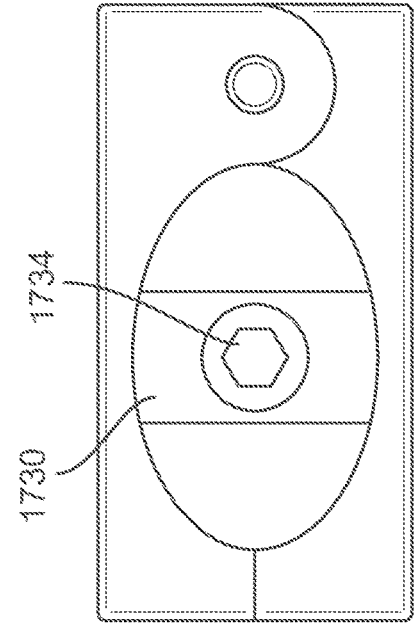

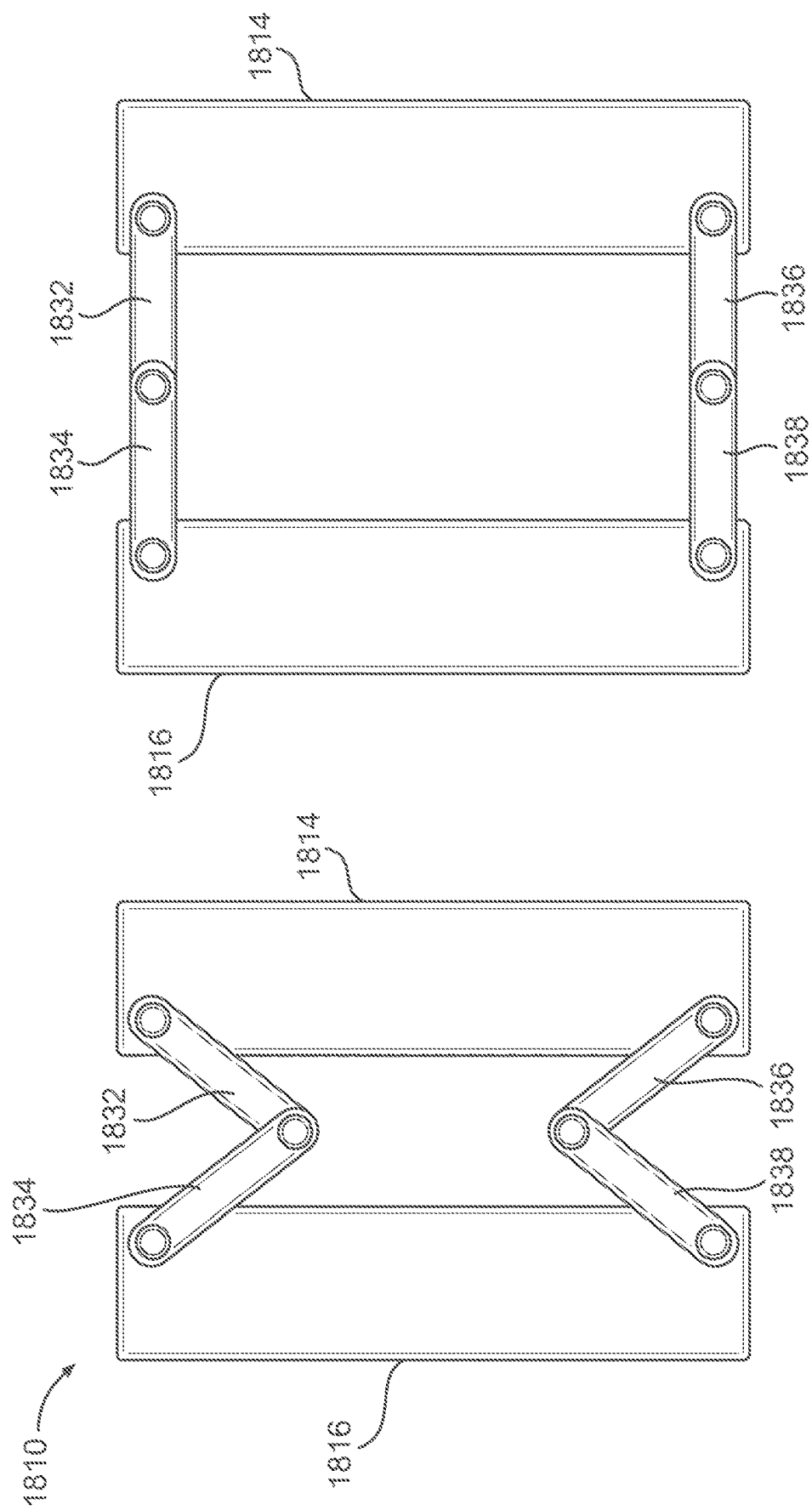

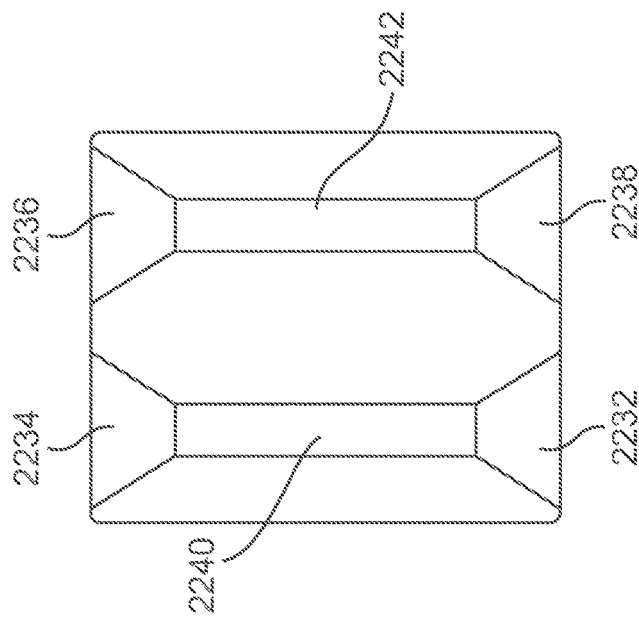
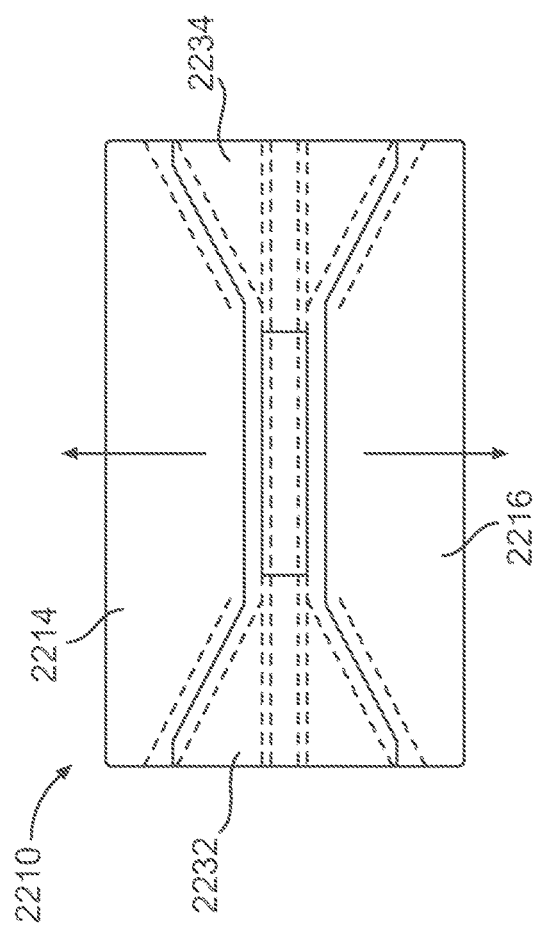
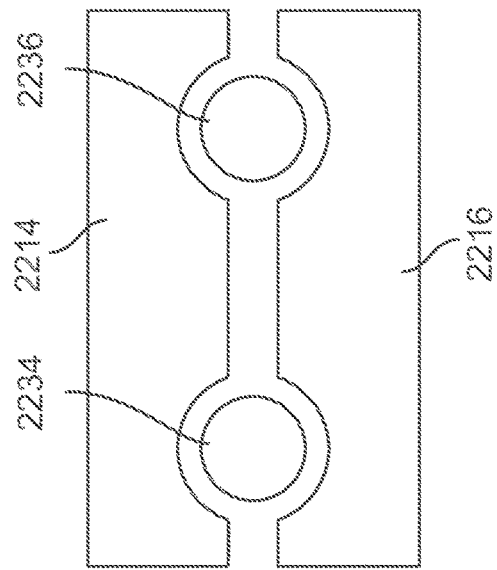
FIG. 96A
FIG. 96B
FIG. 96C

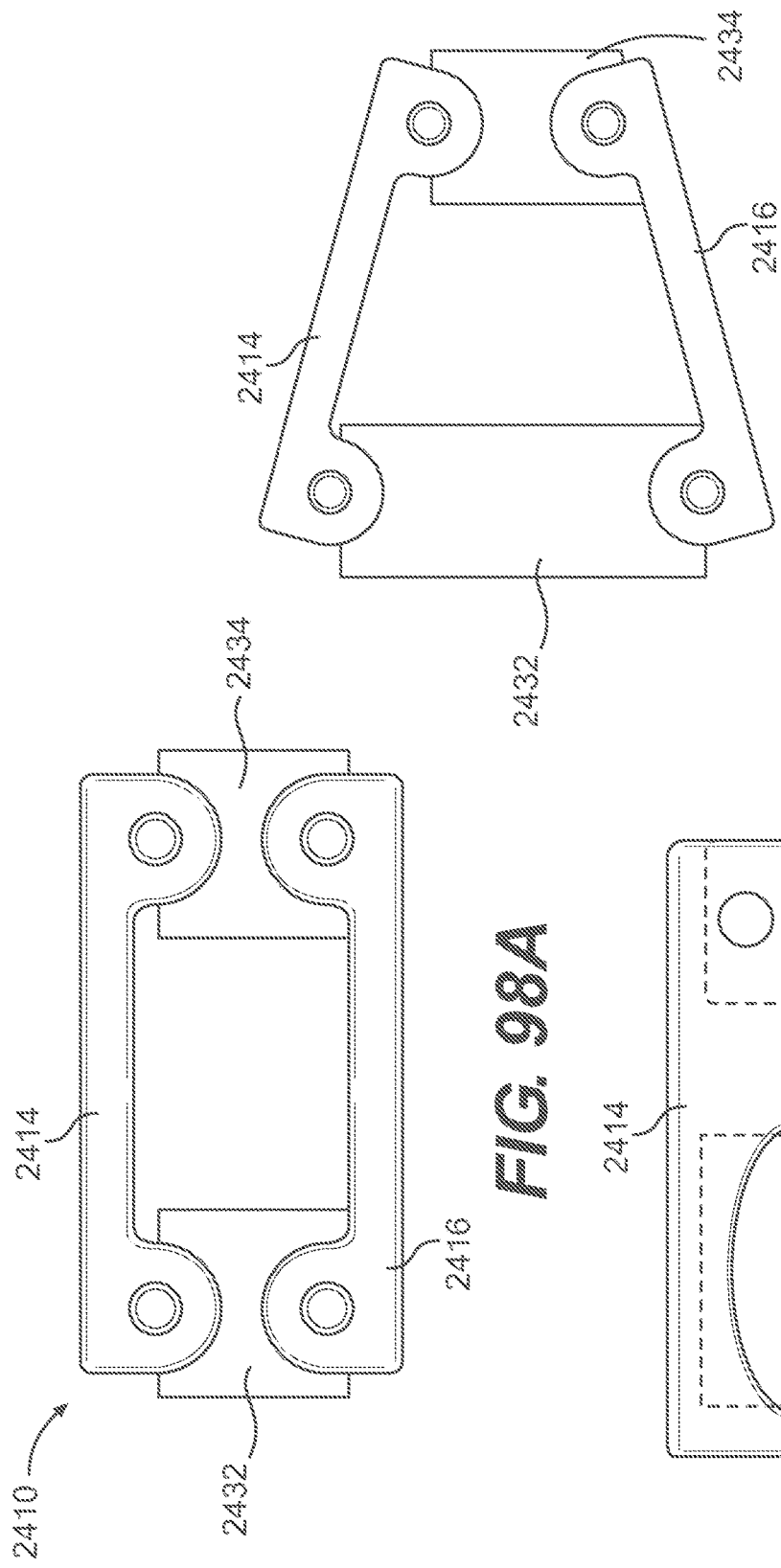

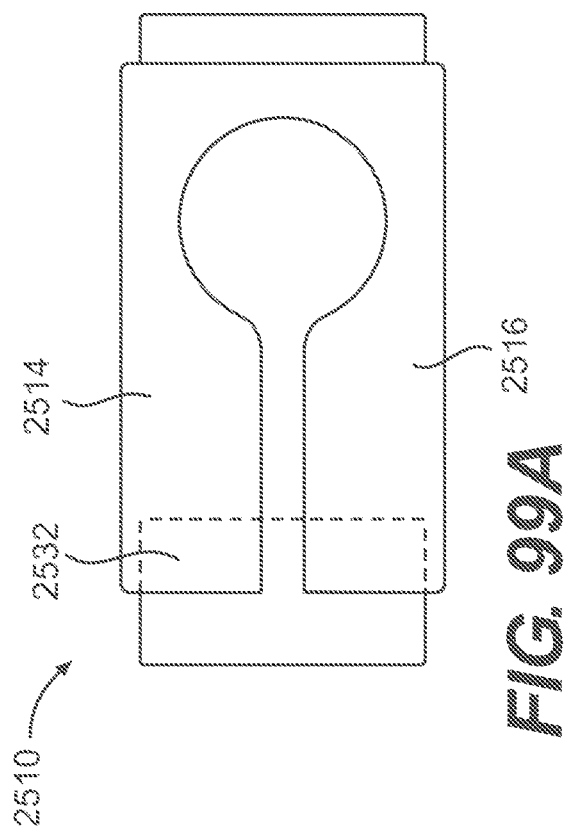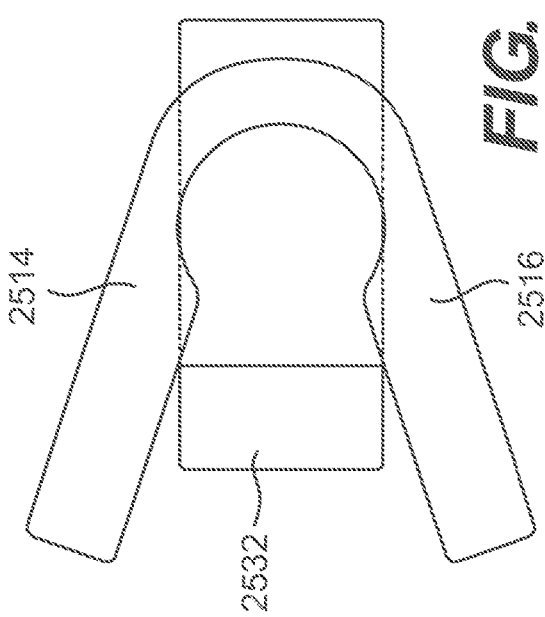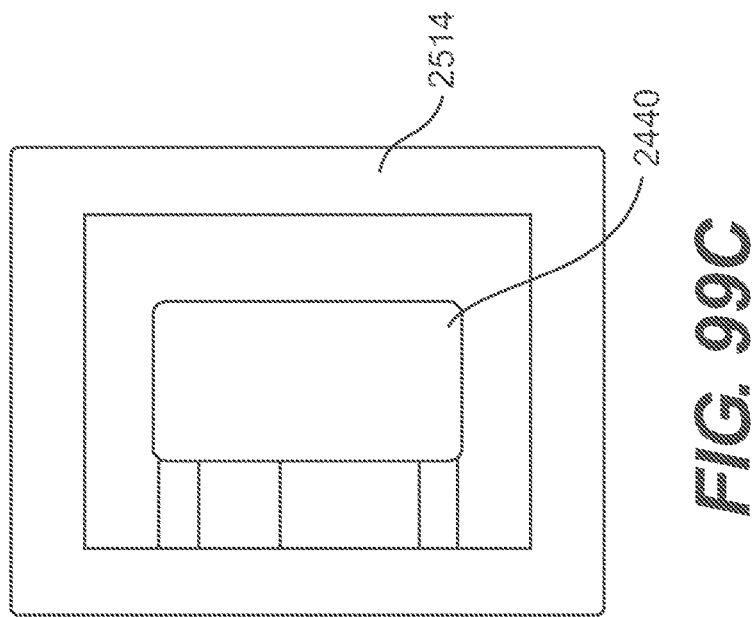

EXPANDABLE FUSION DEVICE AND METHOD OF INSTALLATION THEREOF

CROSS-REFERENCE TO RELATED APPLICATIONS

This Patent Application is a continuation of U.S. patent application Ser. No. 17/388,220, filed on Jul. 29, 2021, which is a continuation of U.S. Ser. No. 16/405,234, filed May 7, 2019, which is a continuation of U.S. Ser. No. 14/485,041, filed Sep. 12, 2014, which (a1) claims priority under 35 U.S.C. § 119(e) to U.S. Provisional Application 61/877,034, filed Sep. 12, 2013, and (a2) is a continuation-in-part application of U.S. Ser. No. 13/845,645, filed Apr. 3, 2013, which is a continuation-in-part application of U.S. patent application Ser. No. 13/451,230, filed Apr. 19, 2012, now issued as U.S. Pat. No. 8,518,120, which is a continuation of U.S. patent application Ser. No. 13/440,158, filed Apr. 5, 2012, now issued as U.S. Pat. No. 8,679,183, which (Ill) is a continuation-in-part application of U.S. patent application Ser. No. 12/823,736, filed Jun. 25, 2010, now issued as U.S. Pat. No. 8,685,098, and (b2) a continuation-in-part application of U.S. patent application Ser. No. 13/273,994, filed Oct. 14, 2011, which is a continuation of U.S. patent application Ser. No. 12/579,833, filed Oct. 15, 2009, now issued as U.S. Pat. No. 8,062,375. The entire content of each of these references cited herein is incorporated by reference in its entirety.

FIELD OF THE INVENTION

The present invention relates to the apparatus and method for promoting an intervertebral fusion, and more particularly relates to an expandable fusion device capable of being inserted between adjacent vertebrae to facilitate the fusion process.

BACKGROUND OF THE INVENTION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing a conventional fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum to no distraction height and for a fusion device that can maintain a normal distance between adjacent vertebral bodies when implanted.

SUMMARY OF THE INVENTION

In an exemplary embodiment, the present invention provides an expandable fusion device capable of being installed inside an intervertebral disc space to maintain normal disc spacing and restore spinal stability, thereby facilitating an intervertebral fusion. In one embodiment, the fusion device includes a body portion, a first endplate, and a second endplate. The first and second endplates are capable of being moved in a direction away from the body portion into an expanded configuration or capable of being moved towards the body portion into an unexpanded configuration. The expandable fusion device is capable of being deployed and installed in the unexpanded configuration or the expanded configuration.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 87A-87C are different views of different components of an alternative expandable fusion device for providing lordosis;

FIGS. 90A-90C illustrate different views of different components of an alternative expandable fusion device having moveable wedges for providing lordosis;

FIGS. 91A-91D illustrate different views of an alternative expandable fusion device having an internal wedge for providing lordosis;

FIGS. 92A and 92B illustrate different views of an alternative expandable fusion device having linking members for providing lordosis;

FIGS. 96A-96C show different views of an implant having a lordotic expansion mechanism comprising threaded barrels;

FIGS. 98A-98C show different views of an implant including a height changing wedge that provides lordotic expansion;

FIGS. 99A-99C show different views of an implant having a driving wedge for providing lordotic expansion;

DETAILED DESCRIPTION OF THE EMBODIMENTS

The following description of the preferred embodiment(s) is merely exemplary in nature and is in no way intended to limit the invention, its application, or uses.

Figure 1:
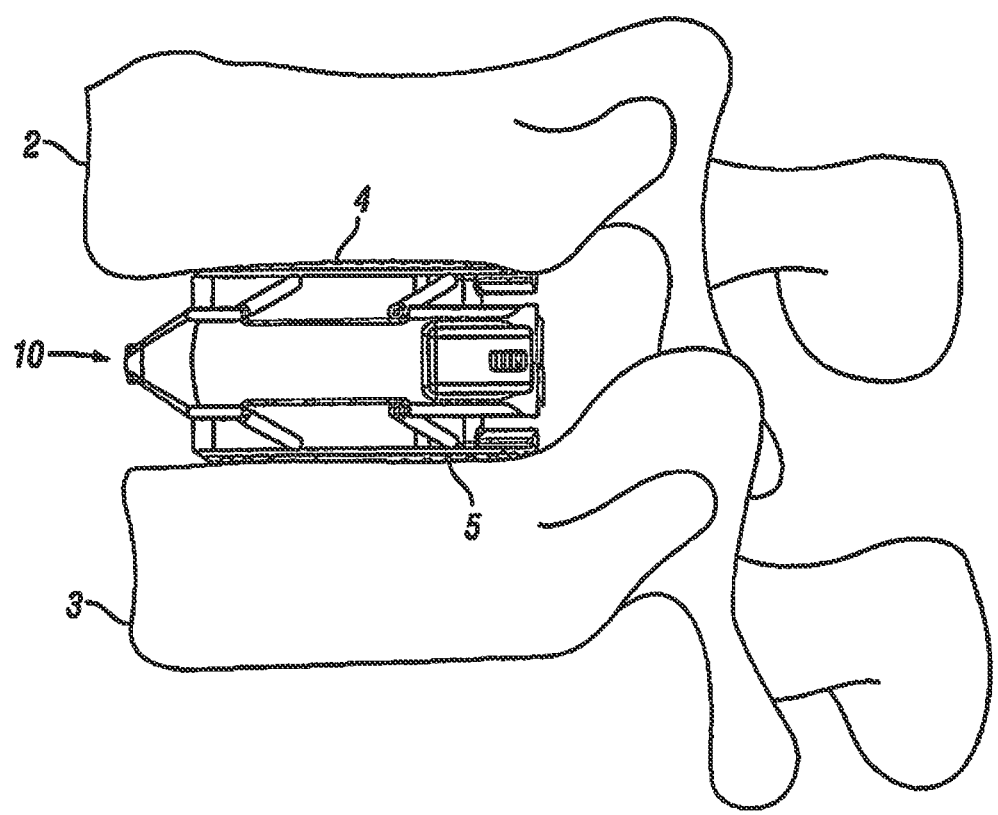
FIG. 1 is a side view of an embodiment of an expandable fusion device shown between adjacent vertebrae according to the present invention.

A spinal fusion is typically employed to eliminate pain caused by the motion of degenerated disk material. Upon successful fusion, a fusion device becomes permanently fixed within the intervertebral disc space. Looking at FIG. 1, an exemplary embodiment of an expandable fusion device 10 is shown between adjacent vertebral bodies 2 and 3. The fusion device 10 engages the endplates 4 and 5 of the adjacent vertebral bodies 2 and 3 and, in the installed position, maintains normal intervertebral disc spacing and restores spinal stability, thereby facilitating an intervertebral fusion. The expandable fusion device 10 can be manufactured from a number of materials including titanium, stainless steel, titanium alloys, non-titanium metallic alloys, polymeric materials, plastics, plastic composites, PEEK, ceramic, and elastic materials.

In an exemplary embodiment, bone graft or similar bone growth inducing material can be introduced around and within the fusion device 10 to further promote and facilitate the intervertebral fusion. The fusion device 10, in one embodiment, is preferably packed with bone graft or similar bone growth inducing material to promote the growth of bone through and around the fusion device. Such bone graft may be packed between the endplates of the adjacent vertebral bodies prior to, subsequent to, or during implantation of the fusion device.

Figure 2:
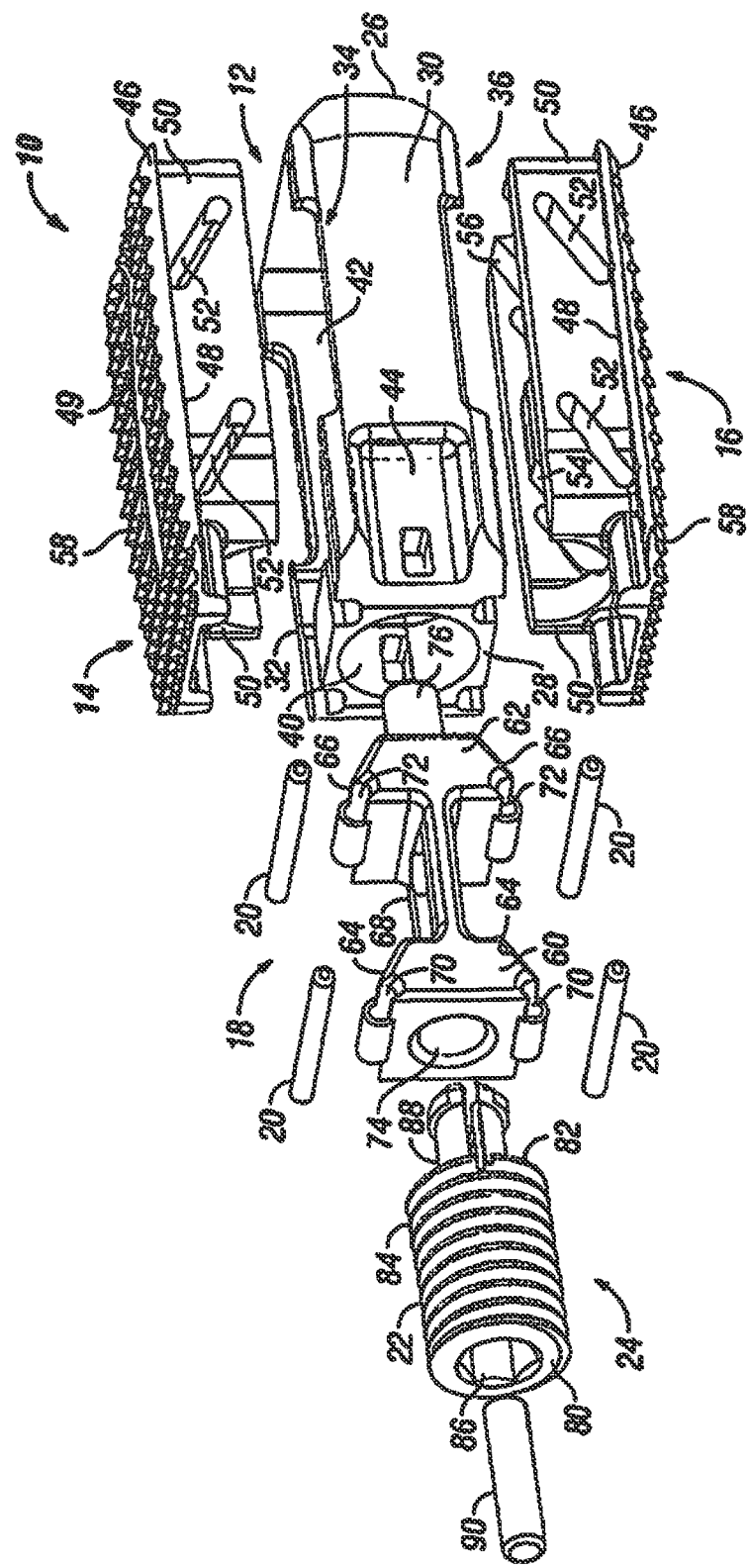
FIG. 2 is an exploded view of the expandable fusion device of FIG. 1.
Figure 3:
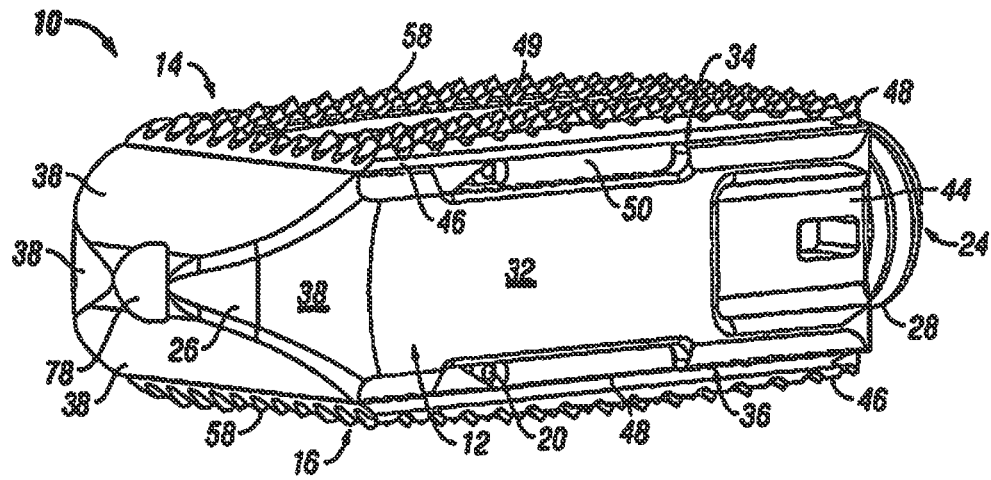
FIG. 3 is a front perspective view of the expandable fusion device of FIG. 1 shown in an unexpanded position

With reference to FIG. 2, an exploded perspective view of one embodiment of the fusion device 10 is shown. In an exemplary embodiment, the fusion device 10 includes a body portion 12, a first endplate 14, a second endplate 16, a translation member 18, a plurality of pins 20, an actuation member 22, and a locking mechanism 24.

With additional reference to FIGS. 3-8, in an exemplary embodiment, the body portion 12 has a first end 26, a second end 28, a first side portion 30 connecting the first end 26 and the second end 28, and a second side portion 32 connecting the first end 26 and the second end 28. The body portion 12 further includes an upper end 34, which is sized to receive at least a portion of the first endplate 14, and a lower end 36, which is sized to receive at least a portion of the second endplate 16.

The first end 26 of the fusion device 10, in an exemplary embodiment, includes at least one angled surface 38, but can include multiple angled surfaces. The angled surface can serve to distract the adjacent vertebral bodies when the fusion device 10 is inserted into an intervertebral space. In another preferred embodiment, it is contemplated that there are at least two opposing angled surfaces forming a generally wedge shaped to distract the adjacent vertebral bodies when the fusion device 10 is inserted into an intervertebral space.

The second end 28 of the body portion 12, in an exemplary embodiment, includes an opening 40 which may include threading. In another exemplary embodiment, the opening 40 may include ratchet teeth instead of threading. The opening 40 extends from the second end 28 of the body portion 12 into a central opening 42 in the body portion 12. In one embodiment, the central opening 42 is sized to receive the translation member 18 and the opening 40 is sized to threadingly receive the actuation member 22. In another exemplary embodiment, the opening 40 is sized to receive the actuation member 22 in a ratcheting fashion. In yet another exemplary embodiment, first side portion 30 and second side portion 32 each include a recess 44 located towards the second end 28 of the body portion 12. The recess 44 is configured and dimensioned to receive an insertion instrument (not shown) that assists in the insertion of the fusion device 10 into an intervertebral space.

Although the following discussion relates to the first endplate 14, it should be understood that it also equally applies to the second endplate 16 as the second endplate 16 is substantially identical to the first endplate 14. Turning now to FIGS. 2-11, in an exemplary embodiment, the first endplate 14 has an upper surface 46, a lower surface 48, and a through opening 49. The through opening 49, in an exemplary embodiment, is sized to receive bone graft or similar bone growth inducing material and further allow the bone graft or similar bone growth inducing material to be packed in the central opening 42 in the body portion 12.

Figure 4:
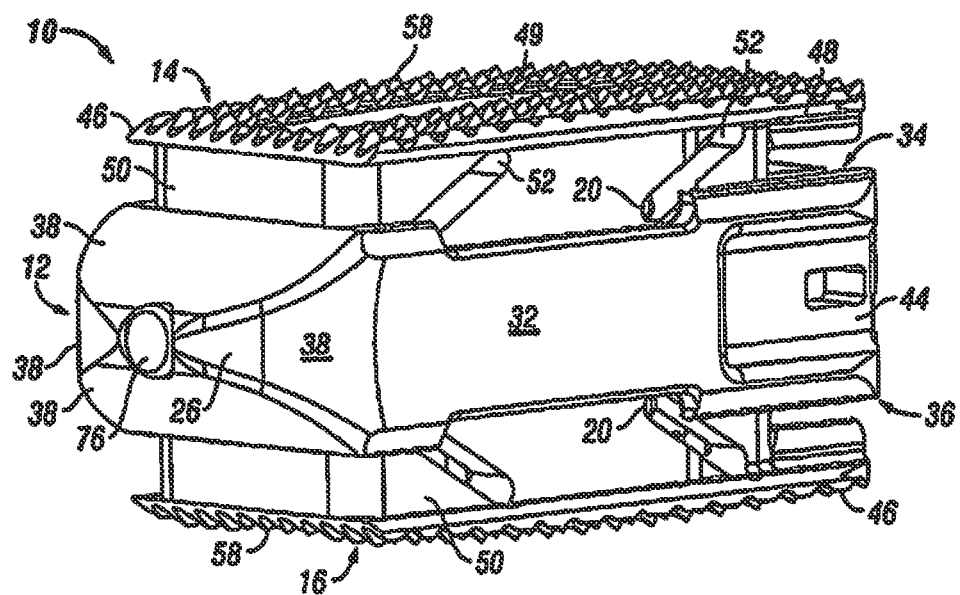
FIG. 4 is a front perspective view of the expandable fusion device of FIG. 1 shown in an expanded position.
Figure 5:
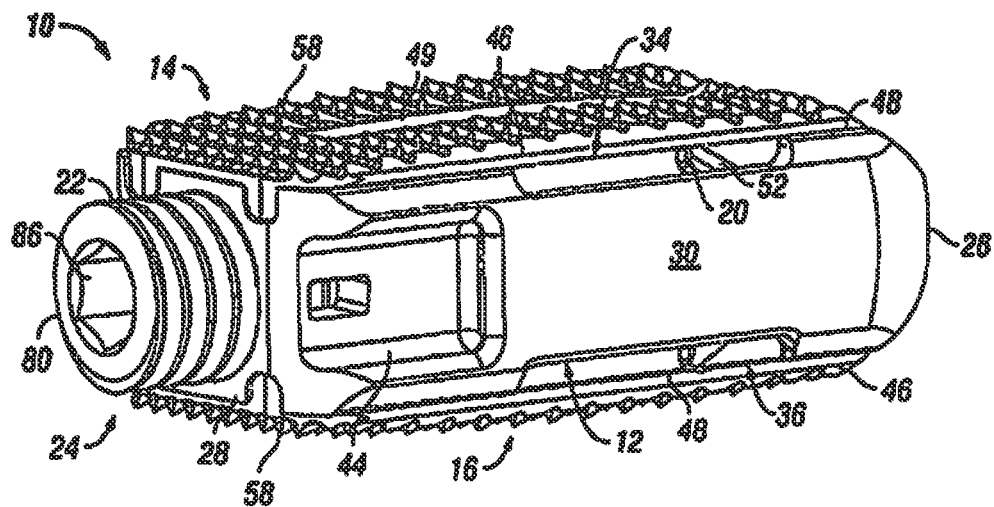
FIG. 5 is a rear perspective view of the expandable fusion device of FIG. 1 shown in an unexpanded position.
Figure 6:
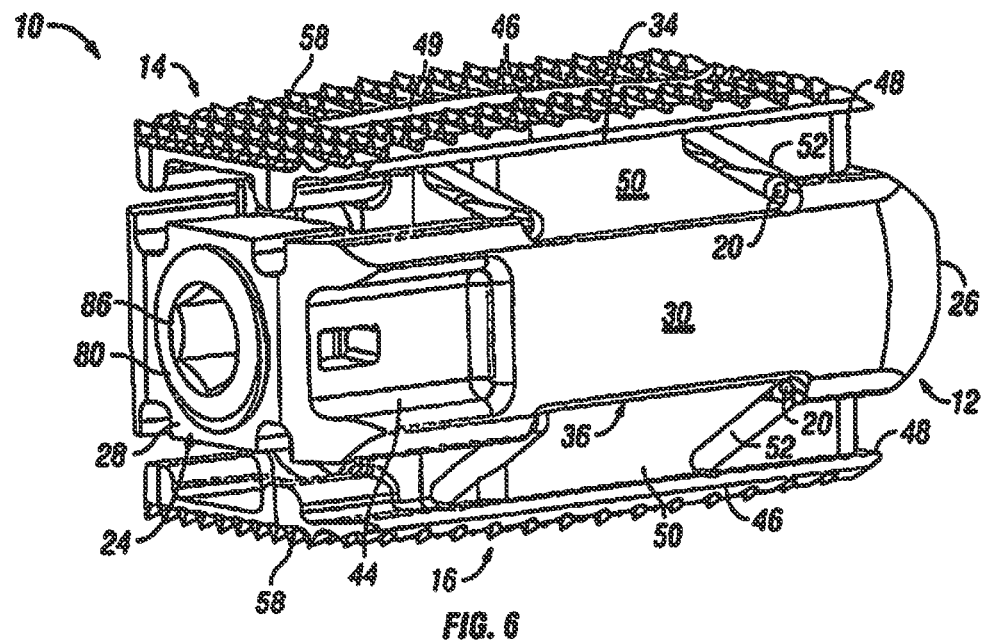
FIG. 6 is a rear perspective view of the expandable fusion device of FIG. 1 shown in an expanded position.
Figure 7:
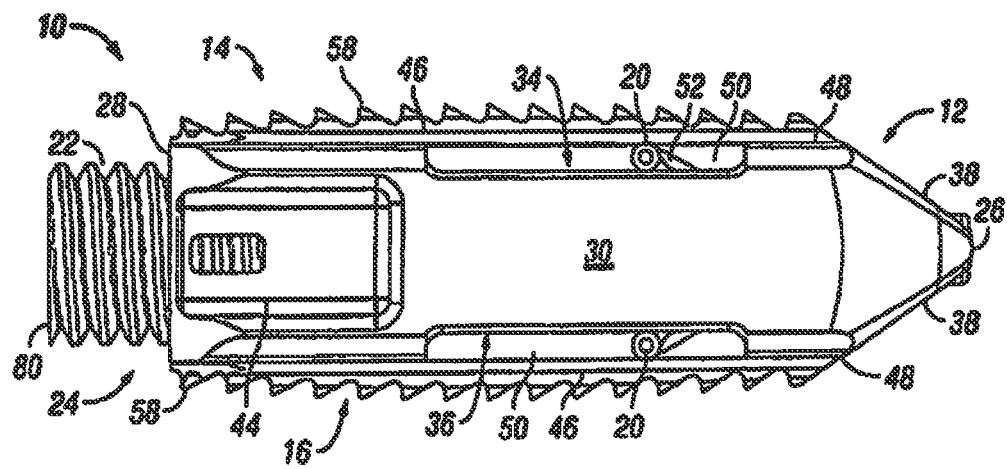
FIG. 7 is a side view of the expandable fusion device of FIG. 1 shown in an unexpanded position.
Figure 8:
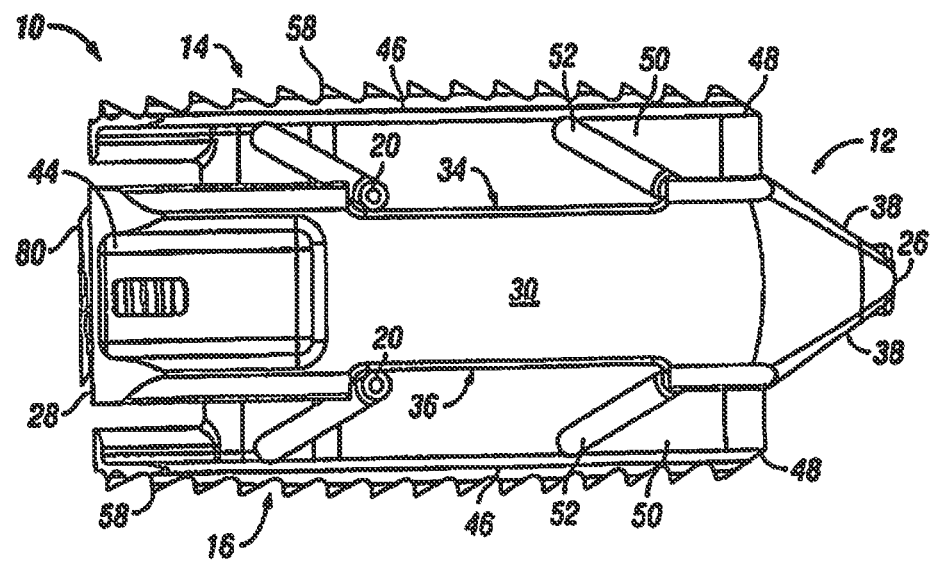
FIG. 8 is a side view of the expandable fusion device of FIG. 1 shown in an expanded position.
Figure 9:
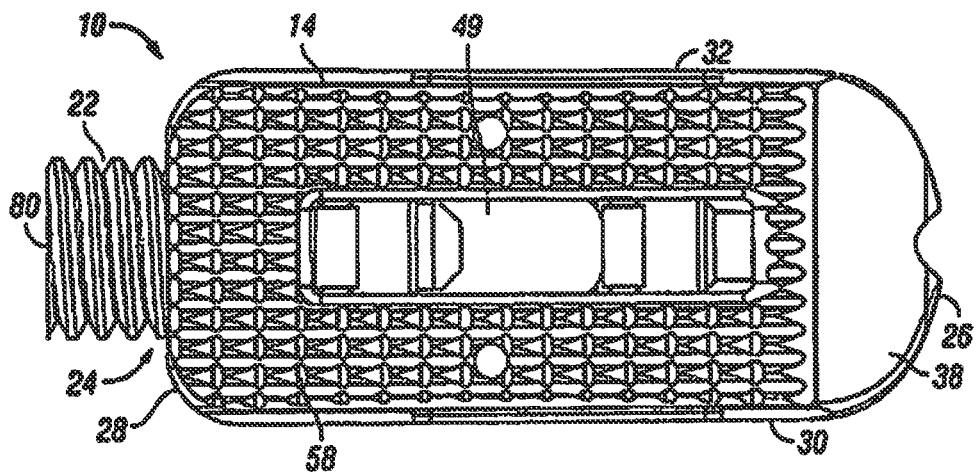
FIG. 9 is a top view of the expandable fusion device of FIG. 1.

In one embodiment, the lower surface 48 includes at least one extension 50 extending along at least a portion of the lower surface 48. As best seen in FIGS. 2 and 4, in an exemplary embodiment, the extension 50 can extend along a substantial portion of the lower surface 48, including, along each side of the endplate 14 and along the front end of the endplate 14. In another exemplary embodiment, the extension 50 includes at least one slot 52, but can include any number of slots 52, including two sets of slots 52 opposing each other, as best seen in FIG. 2. The slots 52 are configured and dimensioned to receive pins 20 and are oriented in an oblique fashion. In another embodiment, the slots 52 may be oriented in a generally vertical orientation.

Figure 12:
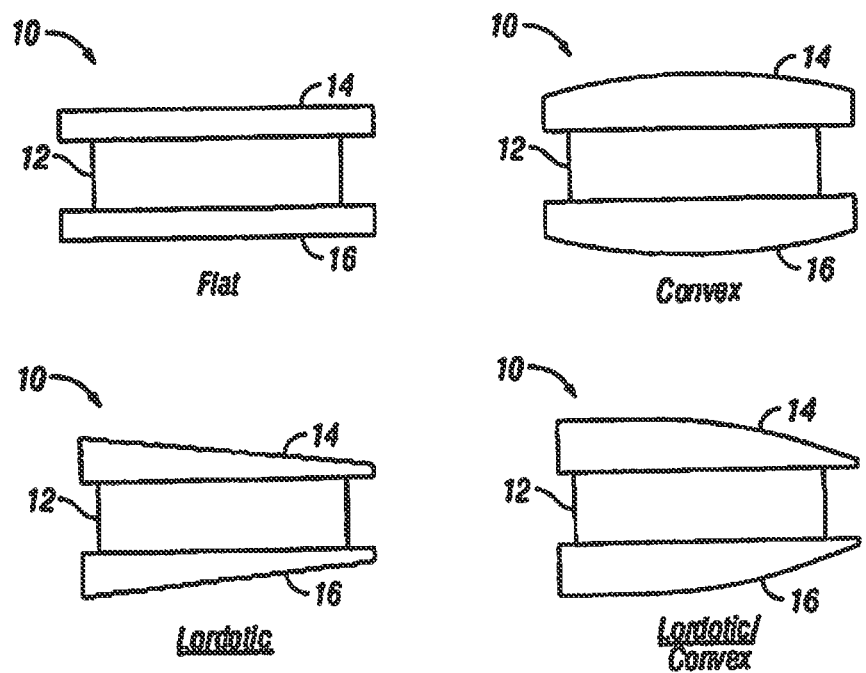
FIG. 12 is a side schematic view of the expandable fusion device of FIG. 1 having different endplates.
Figure 11:
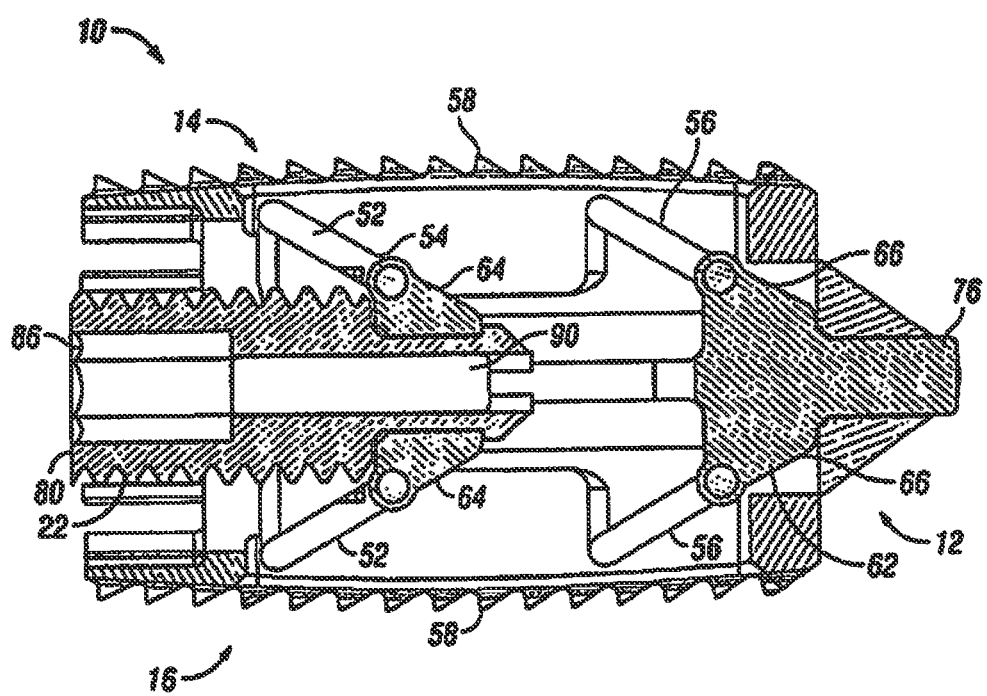
FIG. 11 is a side partial cross-sectional view of the expandable fusion device of FIG. 1 shown in an expanded position.

In an exemplary embodiment, the extension 50 is sized to be received within the central opening 42 of the body portion 12. As best seen in FIGS. 11-12, the lower surface 48 of the first endplate 14 further includes, in an exemplary embodiment, at least one ramped surface 54. In another exemplary embodiment, there are two spaced ramped surfaces 54, 56. It is contemplated that the slope of the ramped surfaces 54, 56 can be equal or can differ from each other. The effect of varying the slopes of the ramped surfaces 54, 56 is discussed below.

Referring now to FIGS. 2-9, in one embodiment, the upper surface 46 of the first endplate 14 is flat and generally planar to allow the upper surface 46 of the endplate 14 to engage with the adjacent vertebral body 2. Alternatively, as shown in FIG. 12, the upper surface 46 can be curved convexly or concavely to allow for a greater or lesser degree of engagement with the adjacent vertebral body 2. It is also contemplated that the upper surface 46 can be generally planar but includes a generally straight ramped surface or a curved ramped surface. The ramped surface allows for engagement with the adjacent vertebral body 2 in a lordotic fashion. Turning back to FIGS. 2-9, in an exemplary embodiment, the upper surface 46 includes texturing 58 to aid in gripping the adjacent vertebral bodies. Although not limited to the following, the texturing can include teeth, ridges, friction increasing elements, keels, or gripping or purchasing projections.

Figure 10:
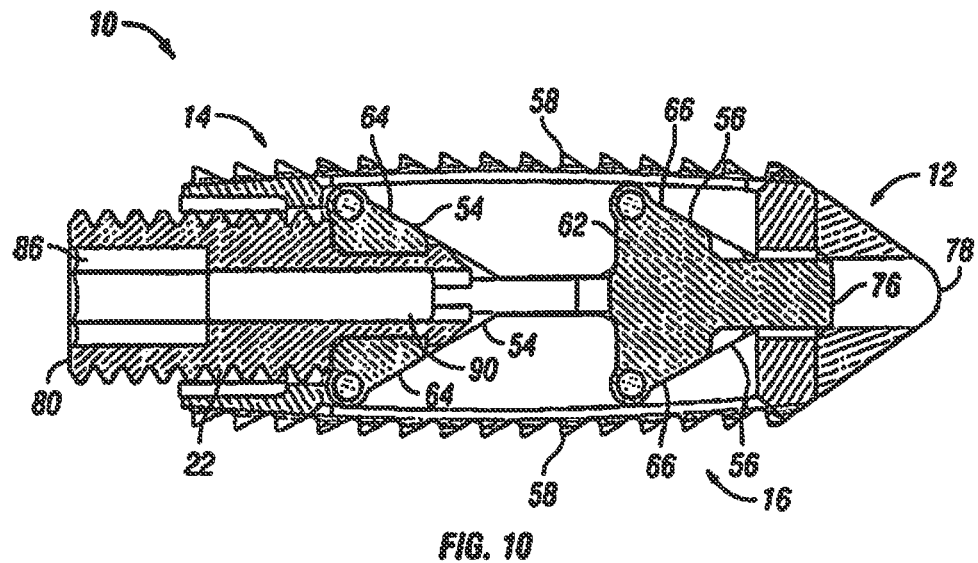
FIG. 10. is a side partial cross-sectional view of the expandable fusion device of FIG. 1 shown in an unexpanded position.

With reference to FIGS. 2 and 10-11, in an exemplary embodiment, the translation member 18 is sized to be received within the central opening 42 of the body portion 12 and includes at least a first expansion portion 60. In another embodiment, the translation member 18 includes a first expansion portion 60 and a second expansion portion 62, the expansion portions 60, 62 being connected together via a bridge portion 68. It is also contemplated that there may be more than two expansion portions where each of the expansion portions is connected by a bridge portion. The expansion portions 60, 62 each have angled surfaces 64, 66 configured and dimensioned to engage the ramp surfaces 54, 56 of the first and second endplates 14, 16. In an exemplary embodiment, the translation member 18 also includes recesses 70, 72, the recesses 70, 72 are sized to receive and retain pins 20. In one embodiment, the expansion portion 60 includes an opening 74, which is sized to receive a portion of the actuation member 22, and the expansion portion 62 includes a nose 76, which is received within an opening 78 in the first end 26 to stabilize the translation member 18 in the central opening 42 of the body member 12.

In an exemplary embodiment, the actuation member 22 has a first end 80, a second end 82 and threading 84 extending along at least a portion thereof from the first end 80 to the second end 82. The threading 84 threadingly engages the threading extending along a portion of opening 40 in the body portion 12. In another exemplary embodiment, the actuation member 22 includes ratchet teeth instead of threading. The ratchet teeth engage corresponding ratchet teeth in the opening 40 in the body portion 12. The first end 80 includes a recess 86 dimensioned to receive an instrument (not shown) that is capable of advancing the actuation member 22 with respect to the body portion 12 of the fusion device 10. The second end 82 of the actuation member 22 includes an extension 88 that is received within the opening 74 of the expansion portion 60. In one embodiment, the extension 88 may include a plurality of slits and a lip portion. The plurality of slits allows the extension portion 88 to flex inwardly reducing its diameter when received in the opening 74. Once the lip portion of the extension portion 88 is advanced beyond the end of the opening 74, the extension portion 88 will return back to its original diameter and the lip portion will engage the expansion portion 60. It is further contemplated that a pin member 90 can be included to prevent the extension portion from flexing inwardly thereby preventing the actuation member 22 from disengaging from the translation member 18.

In an exemplary embodiment, the fusion device 10 can further include a locking mechanism 24. The mechanism 24 is designed to resist rotation of the actuation member 22 rather than prevent rotation of the actuation member 22. In an exemplary embodiment, either deformable threading can be included on actuation member 22 or a disruption of the threading may be included where a deformable material is included in the threading disruption. It is contemplated that the deformable member or deformable threading can be made from a deformable or elastic, biocompatible material such as nitinol or PEEK.

Turning now to FIGS. 1-8 and 10-11, a method of installing the expandable fusion device 10 is now discussed. Prior to insertion of the fusion device 10, the intervertebral space is prepared. In one method of installation, a diskectomy is performed where the intervertebral disc, in its entirety, is removed. Alternatively, only a portion of the intervertebral disc can be removed. The endplates of the adjacent vertebral bodies 2, 3 are then scraped to create an exposed end surface for facilitating bone growth across the invertebral space. The expandable fusion device 10 is then introduced into the intervertebral space, with the first end 26 being inserted first into the disc space followed by the second end 28. In an exemplary method, the fusion device 10 is in the unexpanded position when introduced into the intervertebral space. The wedged shaped first end 26 will assist in distracting the adjacent vertebral bodies 2, 3 if necessary. This allows for the option of having little to no distraction of the intervertebral space prior to the insertion of the fusion device 10. In another exemplary method, the intervertebral space may be distracted prior to insertion of the fusion device 10. The distraction provide some benefits by providing greater access to the surgical site making removal of the intervertebral disc easier and making scraping of the endplates of the vertebral bodies 2, 3 easier.

With the fusion device 10 inserted into and seated in the appropriate position in the intervertebral disc space, the fusion device can then expanded into the expanded position, as best seen in FIGS. 1, 4, 6, 8, and 11. To expand the fusion device 10, an instrument is engaged with recess 86 in the actuation member 22. The instrument is used to rotate actuation member 22. As discussed above, actuation member 22 is threadingly engaged body portion 12 and is engaged with translation member 18; thus, as the actuation member 22 is rotated in a first direction, the actuation member 22 and the translation member 18 move with respect to the body portion 12 toward the first end 26 of the body portion 12. In another exemplary embodiment, the actuation member 22 is moved in a linear direction with the ratchet teeth engaging as means for controlling the movement of the actuation member 22 and the translation member 18. As the translation member 18 moves, the ramped surface 64, 66 of the expansion portions 60, 62 push against the ramped surfaces 54, 56 of the endplates 14, 16 pushing endplates 14, 16 outwardly into the expanded position. This can best be seen in FIGS. 10 and 11. Since the expansion of the fusion device 10 is actuated by a rotational input, the expansion of the fusion device 10 is infinite. In other words, the endplates 14, 16 can be expanded to an infinite number of heights dependent on the rotational advancement of the actuation member 22. As discussed above, the fusion device 10 includes a locking mechanism 24 which assists in retaining the endplates 14, 16 at the desired height.

Figure 13:
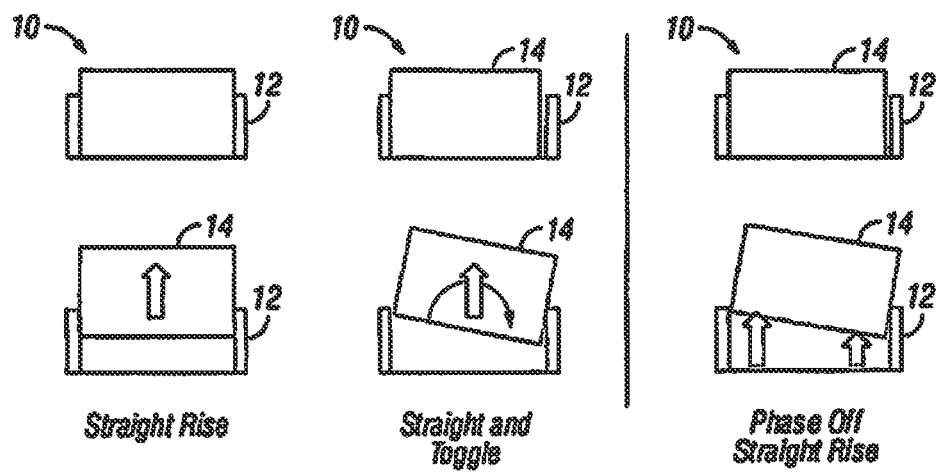
FIG. 13 is a partial side schematic view of the expandable fusion device of FIG. 1 showing different modes of endplate expansion.

It should also be noted that the expansion of the endplates 14, 16 can be varied based on the differences in the dimensions of the ramped surfaces 54, 56, 64, 66. As best seen in FIG. 13, the endplates 14, 16 can be expanded in any of the following ways: straight rise expansion, straight rise expansion followed by a toggle into a lordotic expanded configuration, or a phase off straight rise into a lordotic expanded configuration.

Turning back to FIGS. 1-8 and 10-11, in the event the fusion device 10 needs to be repositioned or revised after being installed and expanded, the fusion device 10 can be contracted back to the unexpanded configuration, repositioned, and expanded again once the desired positioning is achieved. To contract the fusion device 10, the instrument is engaged with recess 86 in the actuation member 22. The instrument is used to rotate actuation member 22. As discussed above, actuation member 22 is threadingly engaged body portion 12 and is engaged with translation member 18; thus, as the actuation member 22 is rotated in a second direction, opposite the first direction, the actuation member 22 and translation member 18 move with respect to the body portion 12 toward the second end 28 of the body portion 12. As the translation member 18 moves, the pins 20, a portion of which are located within the slots 52, ride along the slots 52 pulling the endplates 14, 16 inwardly into the unexpanded position.

Figure 14:
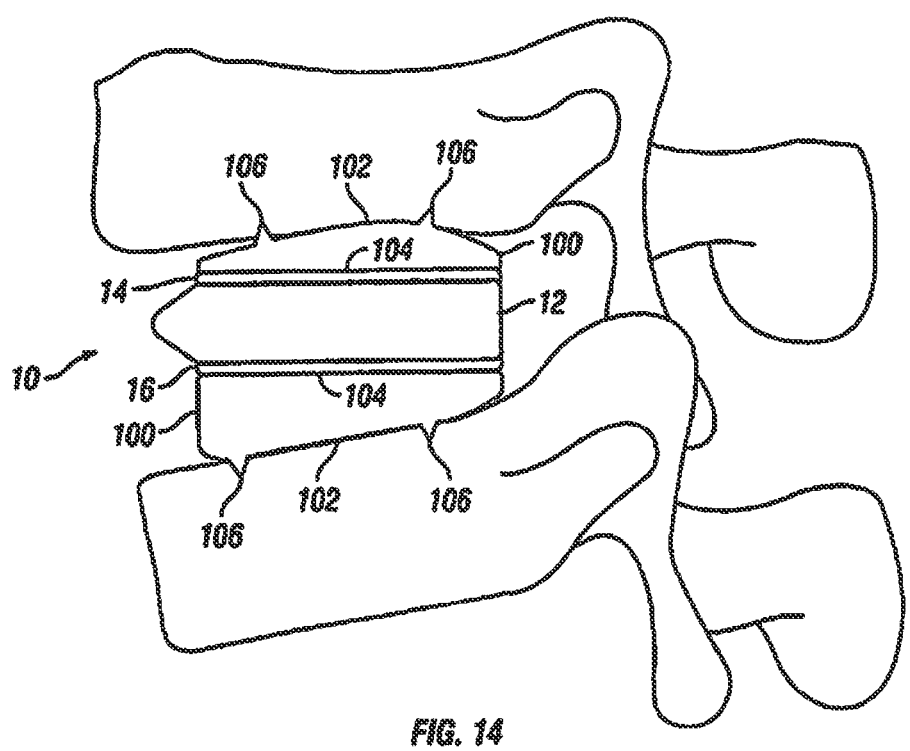
FIG. 14 is a side schematic view of the expandable fusion device of FIG. 1 with artificial endplates shown between adjacent vertebrae.

With reference now to FIG. 14, fusion device 10 is shown with an exemplary embodiment of artificial endplates 100. Artificial endplates 100 allows the introduction of lordosis even when the endplates 14 and 16 of the fusion device 10 are generally planar. In one embodiment, the artificial endplates 100 have an upper surface 102 and a lower surface 104. The upper surfaces 102 of the artificial endplates 100 have at least one spike 106 to engage the adjacent vertebral bodies. The lower surfaces 104 have complementary texturing or engagement features on their surfaces to engage with the texturing or engagement features on the upper endplate 14 and the lower endplate 16 of the fusion device 10. In an exemplary embodiment, the upper surface 102 of the artificial endplates 100 have a generally convex profile and the lower surfaces 104 have a generally parallel profile to achieve lordosis. In another exemplary embodiment, fusion device 10 can be used with only one artificial endplate 100 to introduce lordosis even when the endplates 14 and 16 of the fusion device 10 are generally planar. The artificial endplate 100 can either engage endplate 14 or engage endplate 16 and function in the same manner as described above with respect to two artificial endplates 100.

Although the preceding discussion only discussed having a single fusion device 10 in the intervertebral space, it is contemplated that more than one fusion device 10 can be inserted in the intervertebral space. It is further contemplated that each fusion device 10 does not have to be finally installed in the fully expanded state. Rather, depending on the location of the fusion device 10 in the intervertebral disc space, the height of the fusion device 10 may vary from unexpanded to fully expanded.

Figure 16:
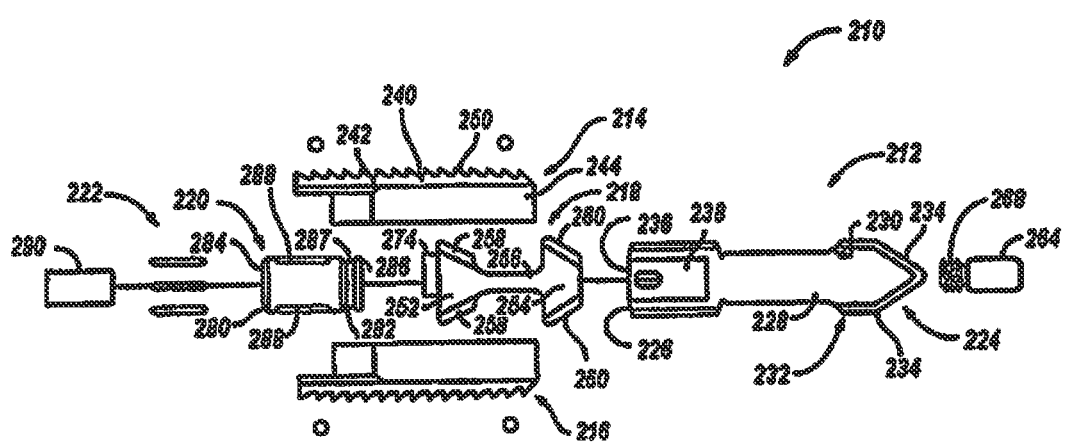
FIG. 16 is an exploded view of the expandable fusion device of FIG. 15.

With reference to FIG. 16, an exploded perspective view of one embodiment of the fusion device 210 is shown. In an exemplary embodiment, the fusion device 210 includes a body portion 212, a first endplate 214, a second endplate 216, a translation member 218, an actuation member 220, and an insert 222.

With additional reference to FIGS. 17-20, in an exemplary embodiment, the body portion 212 has a first end 224, a second end 226, a first side portion 228 connecting the first end 224 and the second end 226, and a second side portion 229 on the opposing side of the body portion 212 connecting the first end 224 and the second end 226. The body portion 212 further includes an upper end 230, which is sized to receive at least a portion of the first endplate 214, and a lower end 232, which is sized to receive at least a portion of the second endplate 216.

The first end 224 of the body portion 212, in an exemplary embodiment, includes at least one angled surface 234, but can include multiple angled surfaces. The angled surface 234 can serve to distract the adjacent vertebral bodies when the fusion device 210 is inserted into an intervertebral space. In another preferred embodiment, it is contemplated that there are at least two opposing angled surfaces forming a generally wedge shaped to distract the adjacent vertebral bodies when the fusion device 210 is inserted into an intervertebral space.

The second end 226 of the body portion 212, in an exemplary embodiment, includes an opening 236 which may include threading. In another exemplary embodiment, the opening 236 may include ratchet teeth instead of threading. The opening 236 extends from the second end 226 of the body portion 212 into a central opening (not illustrated) in the body portion 212. In one embodiment, the central opening is sized to receive the translation member 218, and the opening 236 is sized to threadingly receive the actuation member 220. In another exemplary embodiment, the opening 236 is sized to receive the actuation member 220 in a ratcheting fashion. In yet another exemplary embodiment, first side portion 228 and second side portion 229 each include a recess 238 located towards the second end 226 of the body portion 212. The recess 238 is configured and dimensioned to receive an insertion instrument (not shown) that assists in the insertion of the fusion device 210 into an intervertebral space.

Although the following discussion relates to the first endplate 214, it should be understood that it also equally applies to the second endplate 216 as the second endplate 216 is substantially identical to the first endplate 214 in embodiments of the present invention. Turning now to FIGS. 16-20, in an exemplary embodiment, the first endplate 214 has an upper surface 240, a lower surface 242, and a through opening 243. The through opening 243, in an exemplary embodiment, is sized to receive bone graft or similar bone growth inducing material and further allow the bone graft or similar bone growth inducing material to be packed in the central opening in the body portion 212.

Figure 17:
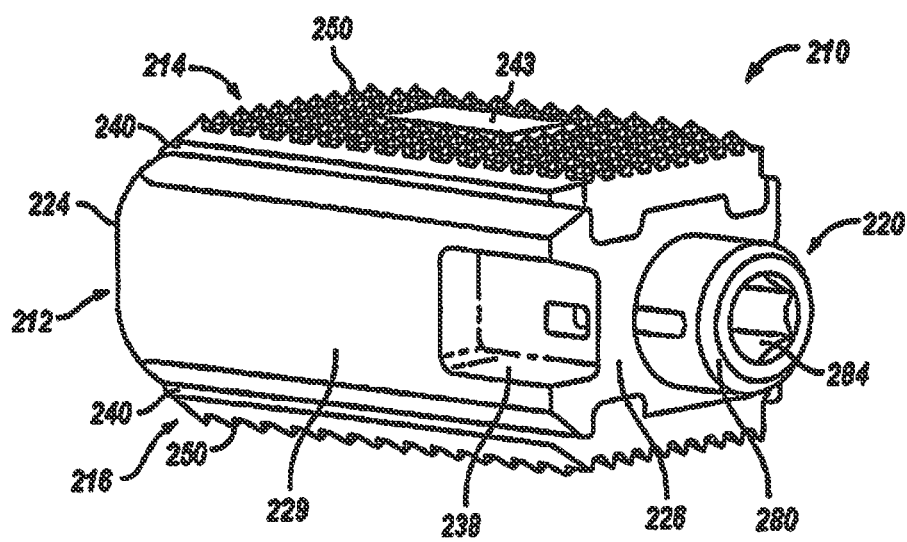
FIG. 17 is a rear perspective view of the expandable fusion device of FIG. 15 shown in an unexpanded position.
Figure 18:
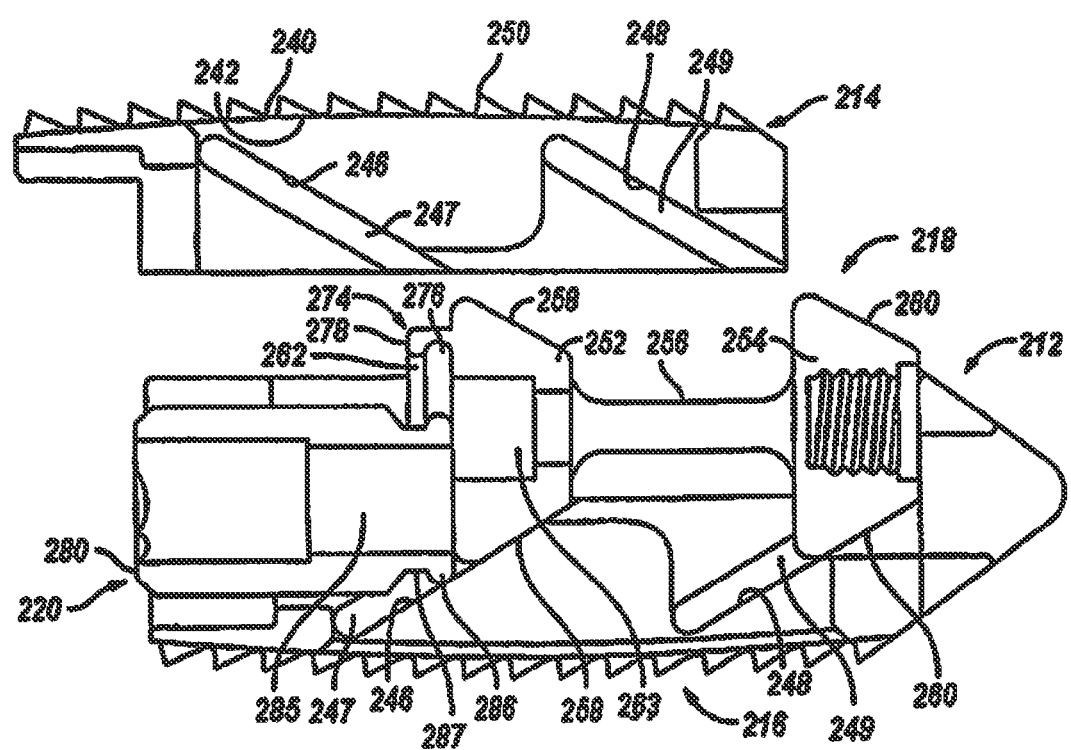
FIG. 18 is a side cross-sectional view of the expandable fusion device of FIG. 15 shown with one of the endplates removed.

In one embodiment, the lower surface 242 includes at least one extension 244 extending along at least a portion of the lower surface 242. As best seen in FIGS. 17 and 18, in an exemplary embodiment, the extension 244 can extend along a substantial portion of the lower surface 242, including, along each side of the endplate 214 and along the front end of the endplate 214. In another exemplary embodiment, the extension 244 includes at least one ramped portion 246, but can include any number of ramped portions, including two spaced ramped portions 246, 248 in the extension 244 that extend between each side of the endplate 214, as best seen in FIG. 18. It is contemplated that the slope of the ramped portions 246, 248 can be equal or can differ from each other. The effect of varying the slopes of the ramped portions 246, 248 is discussed below.

In an exemplary embodiment, the ramped portions 246, 248 further include grooved portions 247, 249 that are configured and dimensioned to receive angled surfaces 258, 260 of the translation member 218 and are oriented in an oblique fashion. In a preferred embodiment, the grooved portions 246, 248 are dovetail grooves configured and dimensioned to hold the angled surfaces 258, 260 of the translation member 218 while allowing the angles surfaces 258, 260 to slide against the ramped portions 246, 248.

Referring now to FIGS. 17-20, in one embodiment, the upper surface 240 of the first endplate 214 is flat and generally planar to allow the upper surface 240 of the endplate 214 to engage with the adjacent vertebral body 202. Alternatively, as shown in FIG. 21, the upper surface 240 can be curved convexly or concavely to allow for a greater or lesser degree of engagement with the adjacent vertebral body 202. It is also contemplated that the upper surface 240 can be generally planar but includes a generally straight ramped surface or a curved ramped surface. The ramped surface allows for engagement with the adjacent vertebral body 202 in a lordotic fashion. Turning back to FIGS. 16-20, in an exemplary embodiment, the upper surface 240 includes texturing 250 to aid in gripping the adjacent vertebral bodies. Although not limited to the following, the texturing can include teeth, ridges, friction increasing elements, keels, or gripping or purchasing projections.

Figure 19:
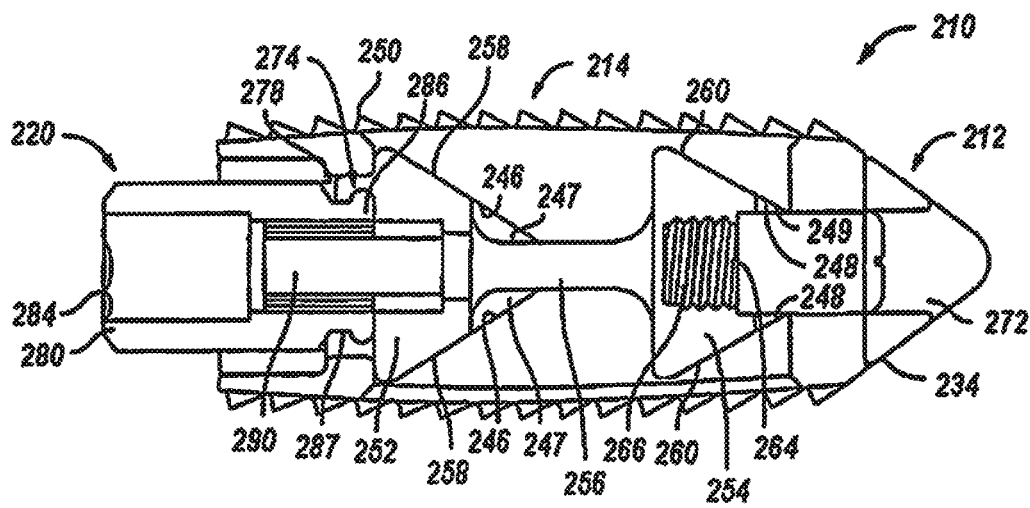
FIG. 19 is a side partial cross-sectional view of the expandable fusion device of FIG. 15 shown in an unexpanded position.
Figure 20:
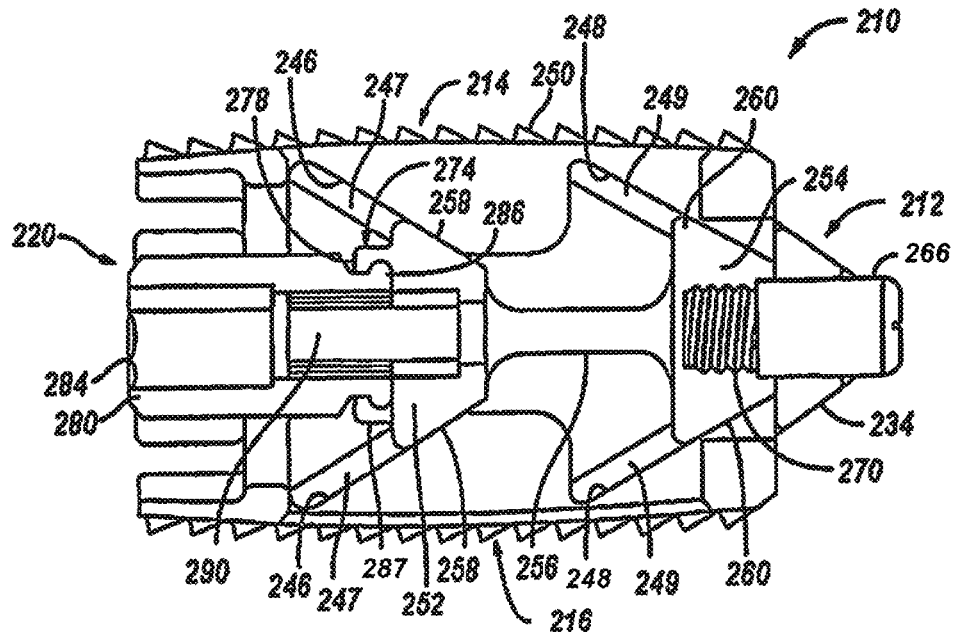
FIG. 20 is a side partial cross-sectional view of the expandable fusion device of FIG. 15 shown in an expanded position.
Figure 21:
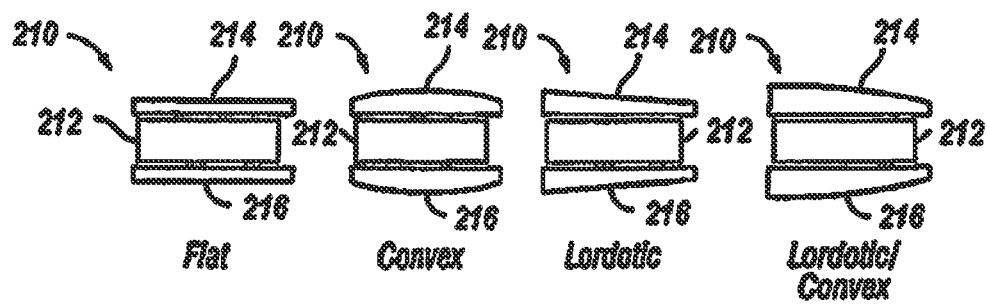
FIG. 21 is a side schematic view of the expandable fusion device of FIG. 15 having different endplates.

With reference to FIGS. 16 and 18-20, in an exemplary embodiment, the translation member 218 is sized to be received within the central opening of the body portion 212 and includes at least a first expansion portion 252. In another embodiment, the translation member 218 includes a first expansion portion 252 and a second expansion portion 254, the expansion portions 252, 254 being connected together via a bridge portion 256. It is also contemplated that there may be more than two expansion portions where each of the expansion portions is connected by a bridge portion. The expansion portions 252, 254 each have angled surfaces 258, 260 configured and dimensioned to engage the grooved portions 246, 248 of the first and second endplates 214, 216. In one embodiment, the translation member 218 includes an opening 262 in the first expansion portion 252, which is sized to receive a portion of the actuation member 220, as best seen in FIG. 18. In an exemplary embodiment, the first expansion portion 252 includes a central bore 263 that extends from the opening 262 and through the first expansion portion 252. In one embodiment, the translation member 218 includes a hole 264 in the second expansion portion 254, which is sized to receive nose 266, as best seen in FIGS. 19 and 20. In an exemplary embodiment, the hole 264 includes threading 268 for threadedly receiving a threaded end 270 of the nose 266, as shown on FIG. 20. The nose 266 is received in an opening 272 in the first end 234 of the body portion 212 to stabilize the translation member 218 in the central opening of the body portion 212.

In one embodiment, the translation member 218 includes a locking mechanism 274, which is configured and adapted to engage the actuation member 220. As illustrated, the locking mechanism 274 may extend from the first expansion portion 252. The locking mechanism 274 includes a slot 276 configured and adapted to receive extension 287 of the actuation member 220. In an exemplary embodiment, the locking mechanism 274 further includes a stop 278 (e.g., a rim, a lip, etc.) that engages the actuation member 220 when it is disposed in the slot 276.

Referring now to FIGS. 16-20, in an exemplary embodiment, the actuation member 220 has a first end 280, a second end 282, and threading (not illustrated) extending along at least a portion thereof from the first end 280 to the second end 282. The threading threadingly engages the threading that extends along a portion of opening 236 in the body portion 212. In another exemplary embodiment, the actuation member 220 includes ratchet teeth instead of threading. The ratchet teeth engage corresponding ratchet teeth in the opening 236 in the body portion 212. The first end 280 includes a recess 284 dimensioned to receive an instrument (not shown) that is capable of advancing the actuation member 220 with respect to the body portion 212 of the fusion device 210. In an embodiment, the actuation member 220 includes a bore 285, as best seen by FIG. 18, that extends from the recess 284 in the first end to the second 282. The second end 282 of the actuation member 220 includes an extension 286 that is received within the opening 262 in the first expansion portion 252. In one embodiment, the extension 288 may include a lip portion 286 and a plurality of slits 288. The plurality of slits 288 are configured to receive inserts 222. Inserts 222 are provided to limit motion of the actuation member 220. Once the lip portion 286 is placed into the slot 276 of the locking mechanism 274, the lip portion 286 will engage the stop 278 preventing longitudinal movement of the actuation member 220 with respect to the translation member 218. It is further contemplated that a pin member 290 can be included to further secure the actuation member 220 in the translation member 219. In an embodiment, the pin member 290 can be pressed into the central bore 285 of the actuation member 220 and the central bore 263 of the translation member, thereby preventing the actuation member 220 from disengaging from the translation member 218. Additionally, in an exemplary embodiment, the fusion device 210 can further include a chamfered tip 224 for distraction of adjacent vertebrae.

Turning now to FIGS. 15-20, a method of installing the expandable fusion device 210 is now discussed. Prior to insertion of the fusion device 210, the intervertebral space is prepared. In one method of installation, a discectomy is performed where the intervertebral disc, in its entirety, is removed. Alternatively, only a portion of the intervertebral disc can be removed. The endplates of the adjacent vertebral bodies 202, 203 are then scraped to create an exposed end surface for facilitating bone growth across the invertebral space. The expandable fusion device 210 is then introduced into the intervertebral space, with the first end 222 of the body portion 212 being inserted first into the disc space followed by the second end 224. In an exemplary method, the fusion device 210 is in the unexpanded position when introduced into the intervertebral space. The wedged-shaped first end 222 should assist in distracting the adjacent vertebral bodies 202, 203, if necessary. This allows for the option of having little to no distraction of the intervertebral space prior to the insertion of the fusion device 210. In another exemplary method, the intervertebral space may be distracted prior to insertion of the fusion device 210. The distraction provide some benefits by providing greater access to the surgical site making removal of the intervertebral disc easier and making scraping of the endplates of the vertebral bodies 202, 203 easier.

Figure 15:
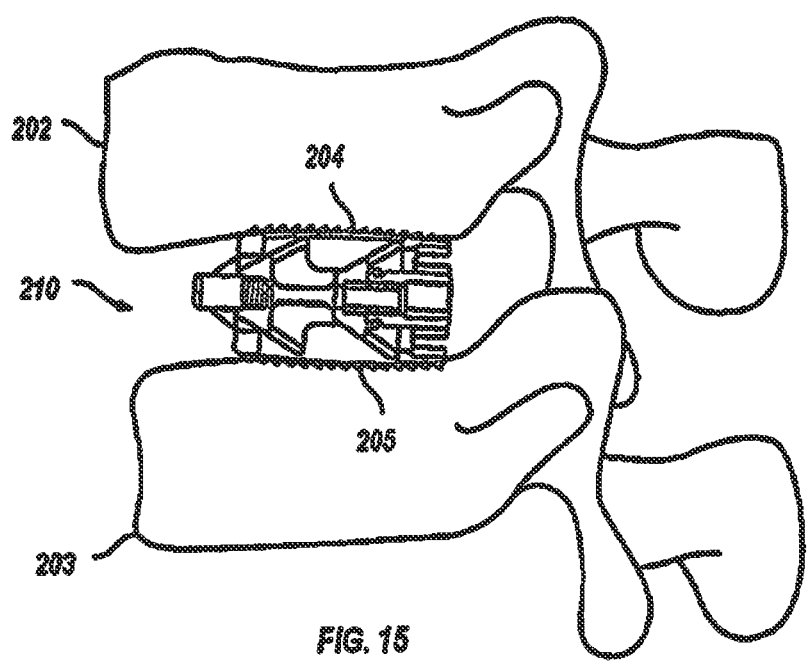
FIG. 15 is a side view of an embodiment of an expandable fusion device shown between adjacent vertebrae according to the present invention.

With the fusion device 210 inserted into and seated in the appropriate position in the intervertebral disc space, the fusion device can then expanded into the expanded position, as best seen in FIGS. 15, 19, and 20. To expand the fusion device 210, an instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a first direction, the actuation member 220 and the translation member 218 move with respect to the body portion 212 toward the first end 222 of the body portion 212. In another exemplary embodiment, the actuation member 220 is moved in a linear direction with the ratchet teeth engaging as means for controlling the movement of the actuation member 220 and the translation member 218. As the translation member 218 moves, the angled surfaces 258, 260 of the expansion portions 252, 254 push against the ramped portions 246, 248 of the endplates 214, 216 pushing endplates 214, 216 outwardly into the expanded position with the angled surfaces 258, 260 riding along the grooved portions 247, 248 of the ramped portions 246, 248. This can best be seen in FIGS. 19 and 20. Since the expansion of the fusion device 210 is actuated by a rotational input, the expansion of the fusion device 210 is infinite. In other words, the endplates 214, 216 can be expanded to an infinite number of heights dependent on the rotational advancement of the actuation member 220. As discussed above, the fusion device 210 includes a locking mechanism 222 which assists in retaining the endplates 14, 16 at the desired height.

Figure 22:
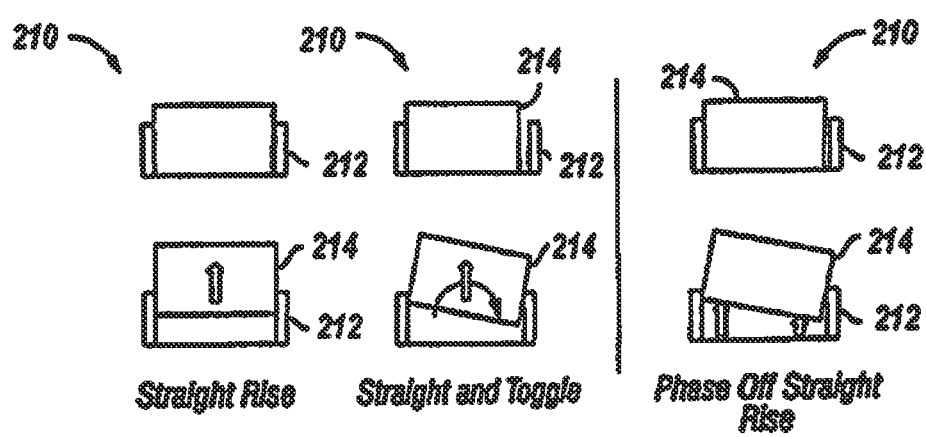
FIG. 22 is a partial side schematic view of the expandable fusion device of FIG. 15 showing different modes of endplate expansion.

It should also be noted that the expansion of the endplates 214, 216 can be varied based on the differences in the dimensions of the ramped portions 246, 248 and the angled surfaces 258, 260. As best seen in FIG. 22, the endplates 214, 216 can be expanded in any of the following ways: straight rise expansion, straight rise expansion followed by a toggle into a lordotic expanded configuration, or a phase off straight rise into a lordotic expanded configuration.

Turning back to FIGS. 15-20, in the event the fusion device 210 needs to be repositioned or revised after being installed and expanded, the fusion device 210 can be contracted back to the unexpanded configuration, repositioned, and expanded again once the desired positioning is achieved. To contract the fusion device 210, the instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a second direction, opposite the first direction, the actuation member 220 and translation member 218 move with respect to the body portion 212 toward the second end 226 of the body portion 212. As the translation member 218 moves, the angled surfaces 258, 260 of the translation member 218 ride along the grooved portions 247, 249 pulling the endplates 214, 216 inwardly into the unexpanded position.

Figure 23:
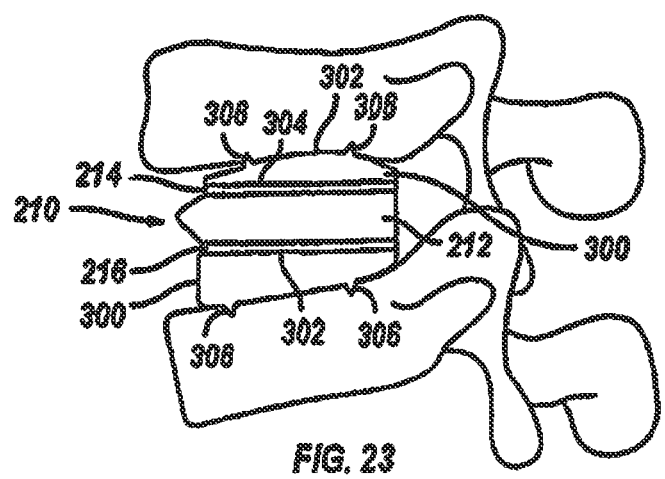
FIG. 23 is a side schematic view of the expandable fusion device of FIG. 15 with artificial endplates shown between adjacent vertebrae.

With reference now to FIG. 23, fusion device 210 is shown with an exemplary embodiment of artificial endplates 300. Artificial endplates 300 allows the introduction of lordosis even when the endplates 214 and 216 of the fusion device 210 are generally planar. In one embodiment, the artificial endplates 300 have an upper surface 302 and a lower surface 304. The upper surfaces 302 of the artificial endplates 300 have at least one spike 306 to engage the adjacent vertebral bodies. The lower surfaces 304 have complementary texturing or engagement features on their surfaces to engage with the texturing or engagement features on the upper endplate 214 and the lower endplate 216 of the fusion device 210. In an exemplary embodiment, the upper surface 302 of the artificial endplates 300 have a generally convex profile and the lower surfaces 304 have a generally parallel profile to achieve lordosis. In another exemplary embodiment, fusion device 210 can be used with only one artificial endplate 300 to introduce lordosis even when the endplates 214 and 216 of the fusion device 210 are generally planar. The artificial endplate 300 can either engage endplate 214 or engage endplate 216 and function in the same manner as described above with respect to two artificial endplates 300.

Figure 24:
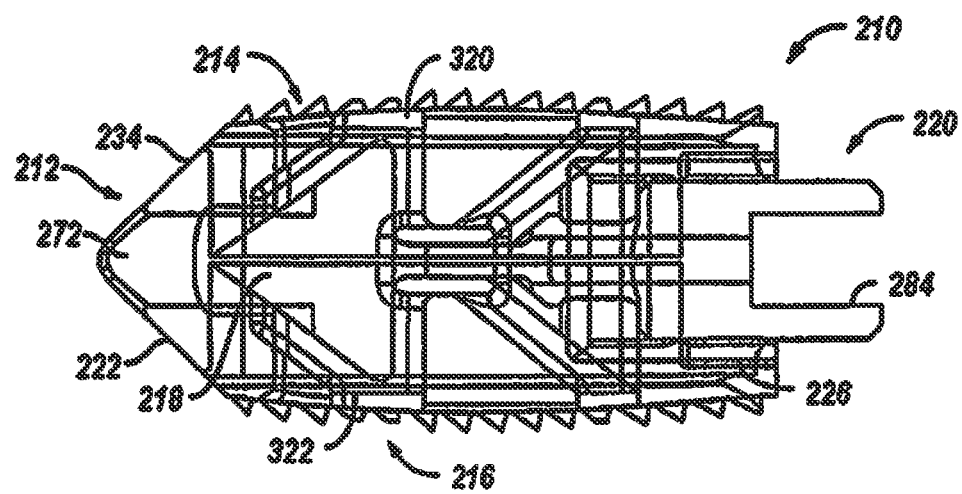
FIG. 24 is a side view cross-sectional view of another embodiment of an expandable fusion device shown in an unexpanded position.
Figure 25:
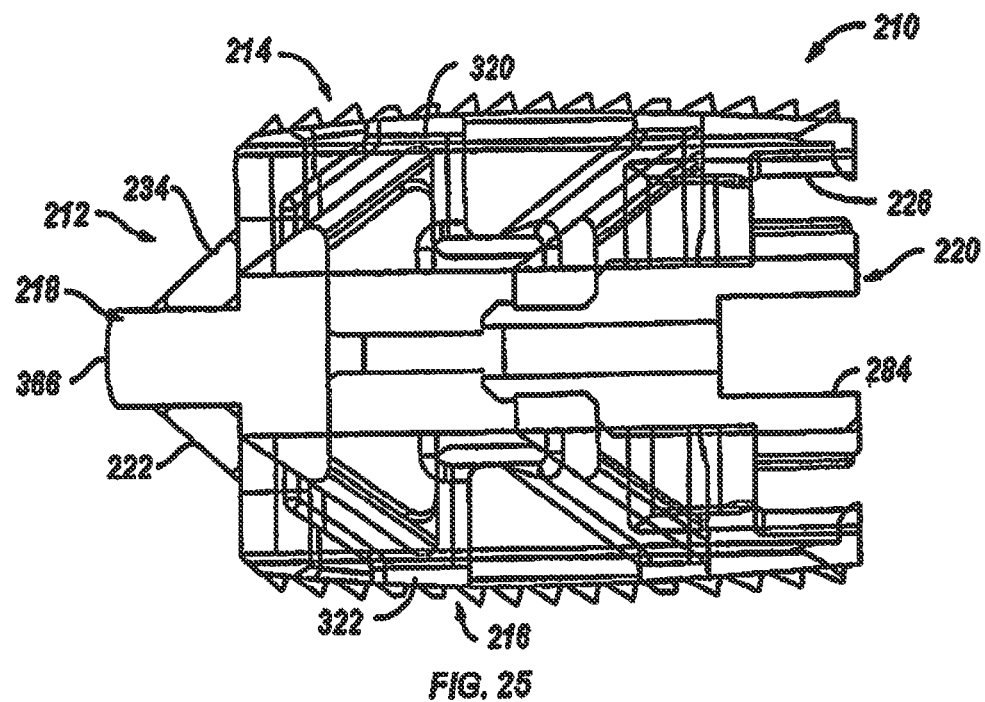
FIG. 25 is a side view cross-sectional view of the expandable fusion device of FIG. 24 shown in an expanded position.
Figure 26:
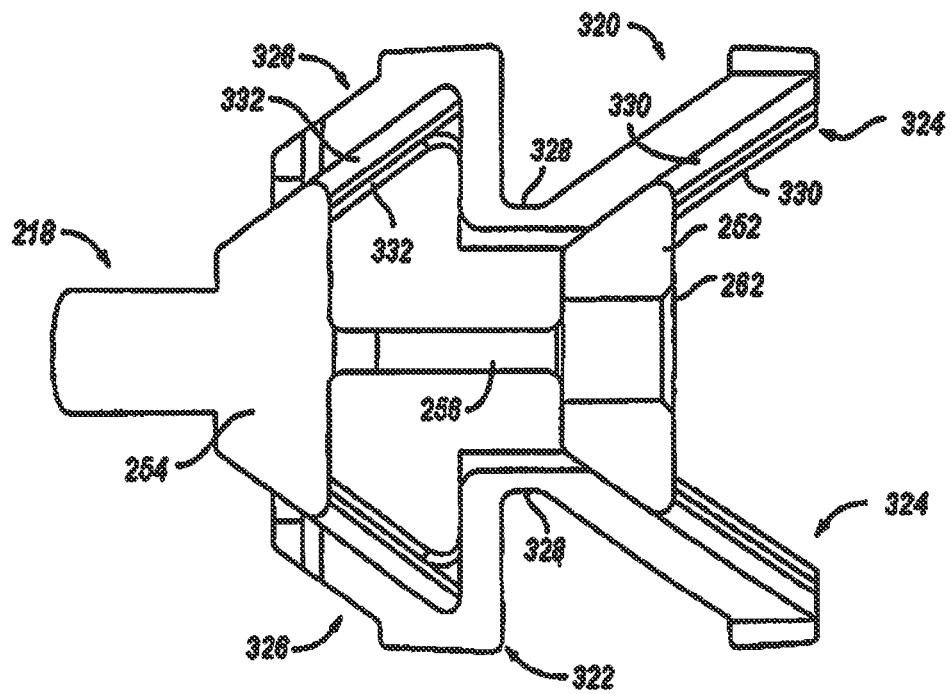
FIG. 26 is a side view of the expandable fusion device of FIG. 24 showing the translation member and the ramped insert.

Referring now to FIGS. 24 and 25, an alternative embodiment of the fusion device 210 is shown. In an exemplary embodiment, the fusion device 210 includes a body portion 212, a first endplate 214, a second endplate 216, a translation member 218, and an actuation member 220. In the illustrated embodiment, the fusion device further includes a first ramped insert 320 and a second ramped insert 322.

Although the following discussion relates to the first ramped insert 320, it should be understood that it also equally applies to the second ramped insert 322 as the second ramped insert 322 is substantially identical to the first ramped insert 320 in embodiments of the present invention. Turning now to FIGS. 24-27, in an exemplary embodiment, the first ramped insert 320 includes a first ramped portion 324 and a second ramped portion 326, the first and second ramped portions 324, 326 being connected by a bridge portion 328. The ramped portions 324, 326 each have grooved portions 330, 332 configured and dimensioned to receive angled surfaces 258, 260 of the translation member. The ramped portions 324, 326 can be oriented in an oblique fashion, as illustrated. In a preferred embodiment, the grooved portions 330, 332 are dovetail grooves configured and dimensioned to hold the angled surfaces 258, 260 of the translation member 218 while allowing the angles surfaces 258, 260 to slide against the ramped portions 324, 326.

In an exemplary embodiment, the first ramped insert 320 should be configured and dimensioned to be engaged with the first endplate 214. In an embodiment, the first and second ramped portions 324, 326 include snap connectors 334, 336 for securing the first ramped insert 320 to the first endplate. It should be understood that the snap connectors 334, 336 are merely illustrative and that other suitable mechanisms for securing the first ramped inserted 320 with the first endplate 214 may be used.

Figure 27:
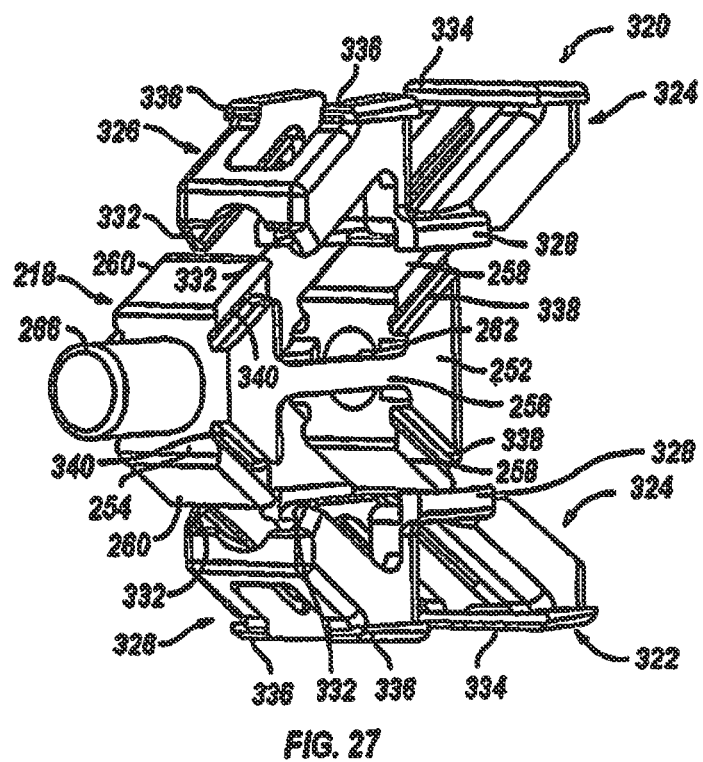
FIG. 27 is a front perspective view of the expandable fusion device of FIG. 24 showing the translation member and the ramped insert.

Referring to FIGS. 24-27, in an exemplary embodiment, the translation member 218 is sized to be received within the central opening of the body portion 212 and includes at least a first expansion portion 252. In another embodiment, the translation member 218 includes a first expansion portion 252 and a second expansion portion 254, the expansion portions 252, 254 being connected together via a bridge portion 256. It is also contemplated that there may be more than two expansion portions where each of the expansion portions is connected by a bridge portion. The expansion portions 252, 254 each have angled surfaces 258, 260 configured and dimensioned to engage the grooved portions 330, 332 of the first and second ramped inserts 320, 322. In one embodiment, the angled surfaces 258, 260 include corresponding grooved portions 338, 340, as best seen in FIG. 27, that slidingly engaged the grooved portions 330, 332 of the first and second ramped inserts 320, 322.

In one embodiment, the expansion portion 252 includes an opening 262, which is sized to receive a portion of the actuation member 220, and the expansion portion 262 includes a nose 266, which is received within an opening 272 in the first end 234 of the body portion 212 to stabilize the translation member 218 in the central opening of the body portion 212. In an embodiment, the nose 266 is integral with the expansion portion 262. In an embodiment (shown on FIGS. 16 and 18-20), the nose 266 is threadingly engaged with the expansion portion 262. In an embodiment, the translation member 218 includes a locking mechanism 274 to engage the actuation member 220, as illustrated in FIGS. 16-20. However, it should be understood that other suitable mechanisms may be used to secure the actuation member 220 within the translation member 218. For example, the actuation member 220 may include an extension 287 having a lip portion 286 (shown on FIGS. 16 and 18-20) that engages the expansion portion 262. The extension 287 may, for example, be configured to flex inwardly reducing its diameter when received in the opening 262. Once the lip portion 286 of the extension 287 is advanced beyond the end of the opening 262, the extension portion 287 will return back to its original diameter and the lip portion 286 will engage the expansion portion 260.

The expandable fusion device 210 of FIGS. 24-27 can be inserted into the intervertebral space in a manner similar to that the previously described with respect to FIGS. 15-20. After insertion, the expandable fusion device 210 of FIGS. 24-27 can be expanded into the expanded position, as best seen in FIGS. 24 and 25. To expand the fusion device 210, an instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a first direction, the actuation member 220 and the translation member 218 move with respect to the body portion 212 toward the first end 222 of the body portion 212. In another exemplary embodiment, the actuation member 220 is moved in a linear direction with the ratchet teeth engaging as means for controlling the movement of the actuation member 220 and the translation member 218. As the translation member 218 moves, the angled surfaces 258, 260 of the expansion portions 252, 254 push against the ramped portions 324, 326 of the first and second ramped inserts 320, 322 while riding along the grooved portions 330, 332, thus pushing first and second ramped inserts 320, 322 outwardly. Because the first and second ramped inserts 320, 322 are engaged with the endplates 214, 216, the endplates 214, 216 are also pushed outwardly into the expanded position.

After expansion, the expandable fusion device 210 can be contracted back to the unexpanded configuration. To contract the fusion device 210, the instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a second direction, opposite the first direction, the actuation member 220 and translation member 218 move with respect to the body portion 212 toward the second end 226 of the body portion 212. As the translation member 218 moves, the angled surfaces 258, 260 of the translation member 218 ride along the grooved portions 330, 332 pulling the first and second ramped inserts 320, 322 and thus, the endplates 214, 216 inwardly into the unexpanded position.

Figure 28:
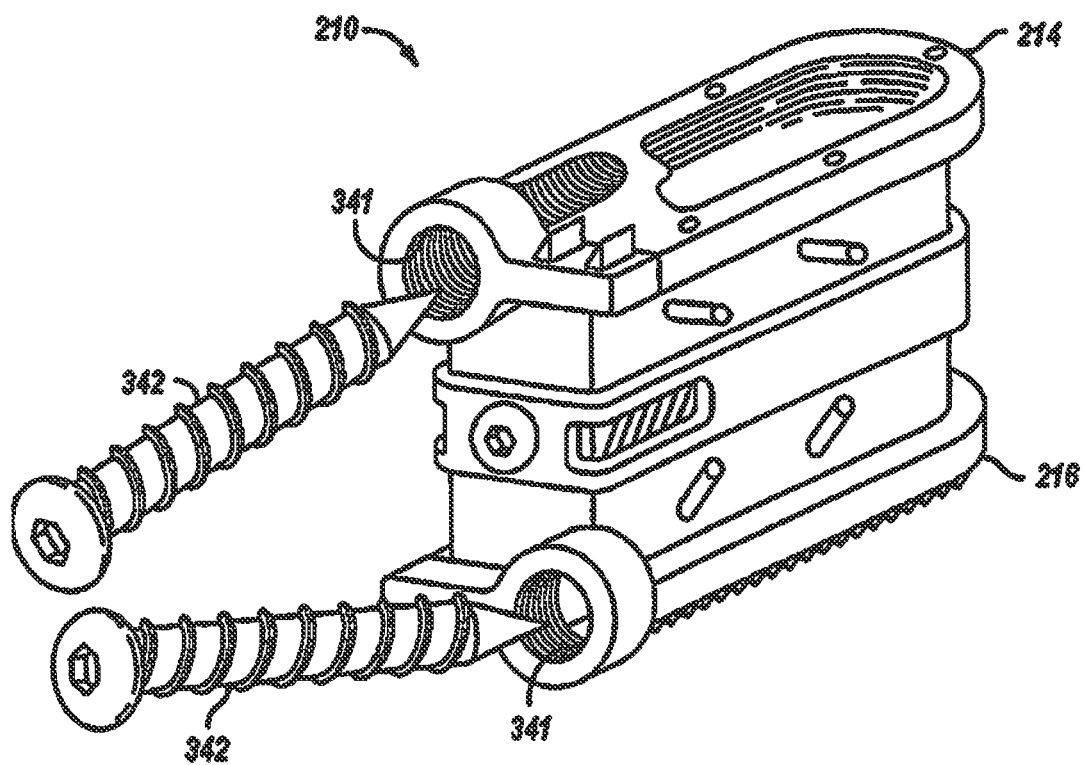
FIG. 28 is a rear perspective of another embodiment of an expandable fusion device with the endplates having a threaded hole.

Referring now to FIG. 28, an alternative embodiment of the fusion device 210 is shown. In an exemplary embodiment, the first endplate 214 and the second endplate 216 each include additional geometry to help securely hold the endplates 214, 216 in place. In an embodiment, the first endplate 214 and/or the second endplate 216 include threaded holes 341 through which the fasteners, such as screws 342, may be inserted. In an embodiment, the threaded holes 341 penetrate through the first endplate 214 and/or the second endplate 216 in an oblique fashion. It is contemplated that the screws 342 may inserted through the threaded holes 341 and into adjacent vertebral bodies 202, 203, to further secure the first endplate 214 and the second endplate 216 to the vertebral bodies 202, 203. In some embodiments, these fasteners may be removed once a more long-term interface has been established, or alternatively the fasteners may remain in place indefinitely or until the fusion device 210 needs adjustment and/or replacement.

Figure 29:
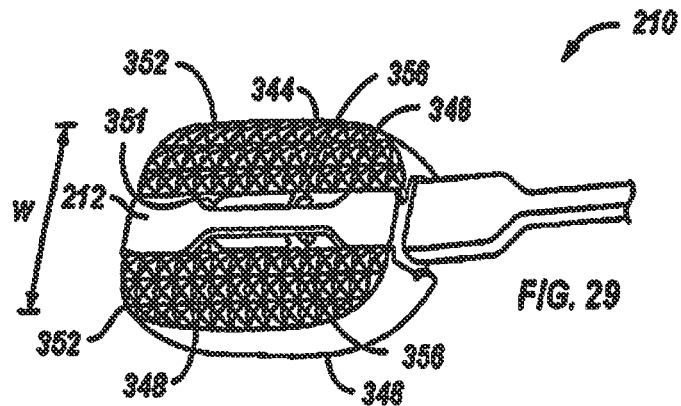
FIG. 29 is a top view of another embodiment of an expandable fusion device shown in an unexpanded position.
Figure 30:
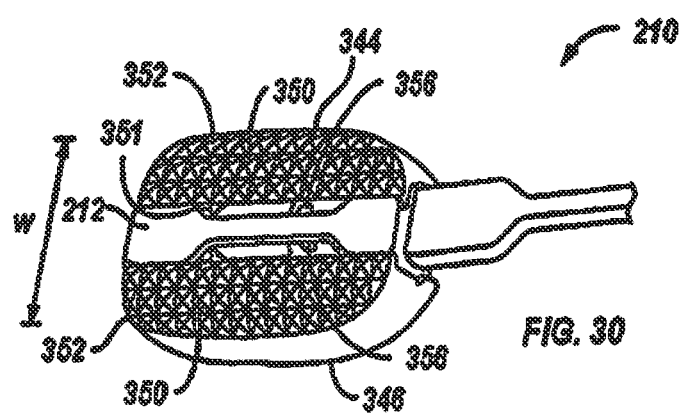
FIG. 30 is a bottom view of the expandable fusion device of FIG. 29.
Figure 31:
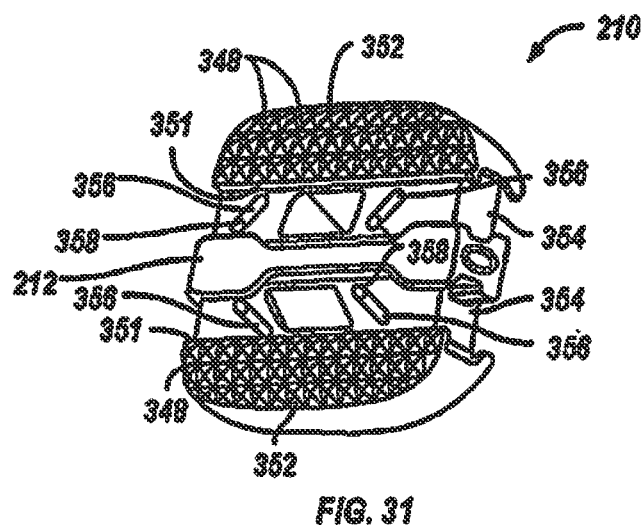
FIG. 31 is top view of the expandable fusion device of FIG. 29 shown in an expanded position.

With reference now FIGS. 29-31, an alternative embodiment of the fusion device 210 is shown that expands laterally. Lateral expansion maximizes coverage of the intravertebral disc space for wider load distribution and stability providing a rigid foundation for fusion. In one embodiment, the fusion device 210 includes body portion 212, first endplate 344, and second endplate 346.

Figure 32:
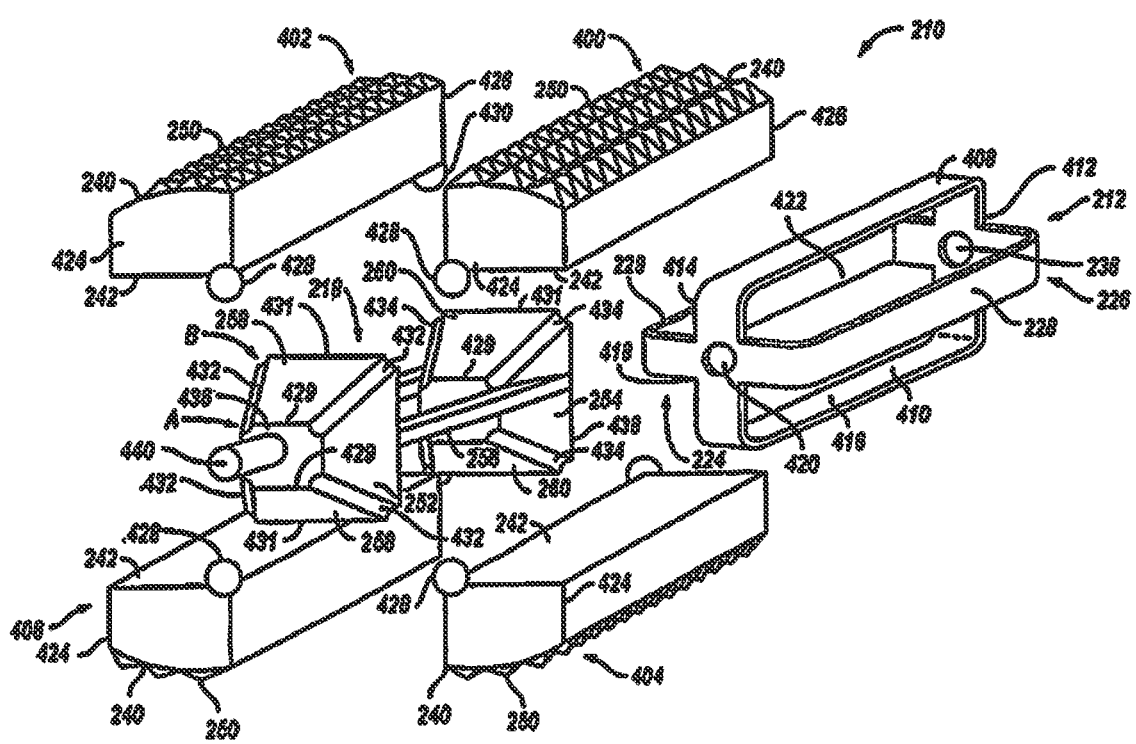
FIG. 32 is an exploded perspective view of another embodiment of an expandable fusion device.
Figure 33:
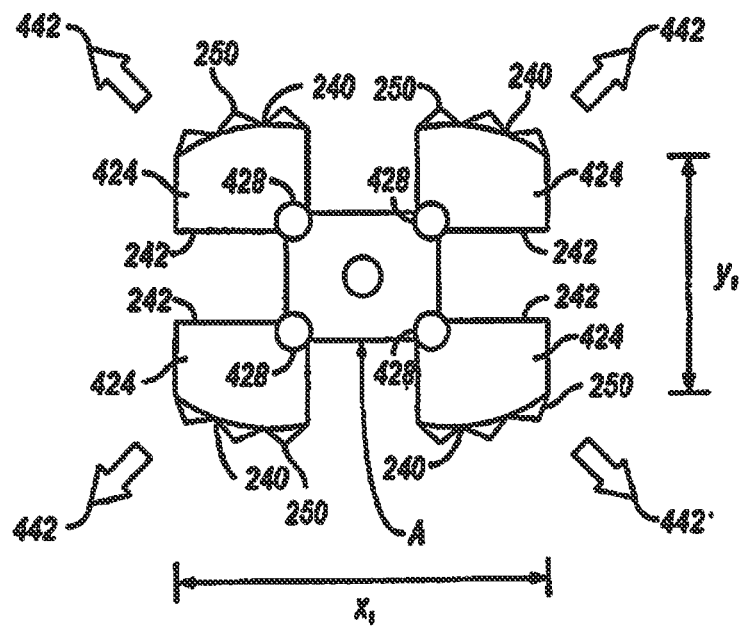
FIG. 33 is an end view of the expandable fusion device of FIG. 32 in an unexpanded position.

Although the following discussion relates to the first endplate 344, it should be understood that it also equally applies to the second endplate 346 as the second endplate 346 is substantially identical to the first endplate 344 in embodiments of the present invention. Turning now to FIGS. 31-33, in an exemplary embodiment, the first endplate 344 has an upper surface 348, a lower surface 350, and an inner surface 351 facing the body portion 212. It is contemplated that the upper surface 348 will engage adjacent vertebral body 202 (seen on FIG. 15) and the lower surface 350 will engage adjacent vertebral body 203 (seen on FIG. 15). In one embodiment, the upper surface 348 and the lower surface 350 are each flat and generally planar to allow the upper surface 348 to engage with the adjacent vertebral body 203. Alternatively, the upper surface 348 and/or the lower surface 350 can be curved convexly or concavely to allow for a greater or lesser degree of engagement with the adjacent vertebral bodies 202, 203. It is also contemplated that the upper surface 348 and/or the lower surface 350 can be generally planar but includes a generally straight ramped surface or a curved ramped surface. The ramped surface allows for engagement with the adjacent vertebral body 202 and/or the adjacent vertebral body 203 in a lordotic fashion. In an exemplary embodiment, the upper surface 348 and/or lower surface 350 includes textures 352 to aid in gripping the adjacent vertebral bodies. Although not limited to the following, the texturing can include teeth, ridges, friction increasing elements, keels, or gripping or purchasing projections.

In one embodiment, the inner surface 351 includes at least one extension 354 extending along at least a portion of the inner surface 351. In an exemplary embodiment, the extension 354 can extend along a substantial portion of the inner surface 354, including, along each side of the endplate 344 and along the front end of the endplate 214. While not illustrated, the inner surface may include ramped surfaces and grooved portions in an exemplary embodiment. It is contemplated that the ramped surfaces and/or grooved portions may be similar to the ramped surfaces 246, 248 and grooved portion 247, 249 in extension 244 shown on FIGS. 18-20. In an embodiment, the extension 354 may include slots 356 oriented in an oblique fashion through which pins 358 may be inserted.

While not illustrated, the fusion device 210 further includes features to effectuate the lateral expansion of the first and second endplates 344, 346. In one embodiment, the fusion device 210 using a ramping system—similar to the system illustrated in FIGS. 16 and 18-20—for expanding the first and second endplates 344, 346. In an exemplary embodiment, the fusion device 210 further includes a translation member and actuation member, such as translation member 218 and actuation member 220 shown on FIGS. 16 and 18-20. It is contemplated that the translation member may include angled surfaces that push against ramped surfaces in the extension 354, expanding the first and second endplates 344, 346 outwardly and away from the body portion 212. In an embodiment, pins 356 disposed through the slots 354 may be retained in the translation member. In an alternative embodiment, dovetailing may be used for engagement of the angled surfaces and ramped surfaces. It should be understood that the translation member and actuation member in this embodiment may be similar to the translation member 218 and actuation member 220 described above with respect FIGS. 15-20. In another embodiment, the fusion device 210 further includes first and second ramped inserts that are secured within the first and second endplates 344, 346. The first and second ramped inserts may be similar to the first and second ramped inserts 320, 322 described above with respect to FIGS. 24-27. It is contemplated that angled surfaces in the translation member may push against ramped surfaces in the ramped inserts pushing the ramped inserts outwardly. Because of their engagement with the first and second endplates 344, 346, the first and second endplates 344, 346 may thus be expanded outwardly. In this manner, the first and second endplates 344, 346 may be laterally expanded away from the body portion 212. It should be understood that other suitable techniques may also be used to effectuate this lateral expansion.

With reference to FIG. 32, an exploded perspective view of another embodiment of fusion device 210 is shown. In an exemplary embodiment, the fusion device 210 includes a body portion 212, a first endplate 400, a second endplate 402, a third endplate 404, a fourth endplate 406, and a translation member 218. In this embodiment, the fusion device 210 is configured to expand both vertically and laterally.

In an exemplary embodiment, the body portion 212 has a first end 224, a second end 226, a first side portion 228 connecting the first end 224 and the second end 226, and a second side portion 229 on the opposing side of the body portion 212 connecting the first end 224 and the second end 226. The body portion 212 further includes a top side portion 408 connecting the first end 224 and the second end 226, and a bottom side portion 410 on the opposing side of the body portion 212 connecting the first end 224 and the second end 226. The body portion 212 further includes first gap 412 between the top side portion 408 and the first side portion 228, which is sized to receive at least a portion of the first endplate 400. The body portion 212 further includes second gap 414 between the top side portion 408 and the second side portion 229, which is sized to receive at least a portion of the second endplate 402. The body portion 212 further includes third gap 416 between the bottom side portion 410 and the first side portion 228, which is sized to receive at least a portion of the third endplate 404. The body portion 212 further includes fourth gap 418 between the bottom side portion 410 and the second side portion 229, which is sized to receive at least a portion of the fourth endplate 406.

The first end 224 of the body portion 212, in an exemplary embodiment, includes an opening 420. The opening 420 extends from the first end 224 of the body portion 212 into a central opening 422. In one embodiment, the central opening 422 is sized to receive the translation member 218. The second end 226 of the body portion 212, in an exemplary embodiment, includes an opening 236, which extends from the second end 226 of the body portion 212 into the central opening 422.

Figure 34:
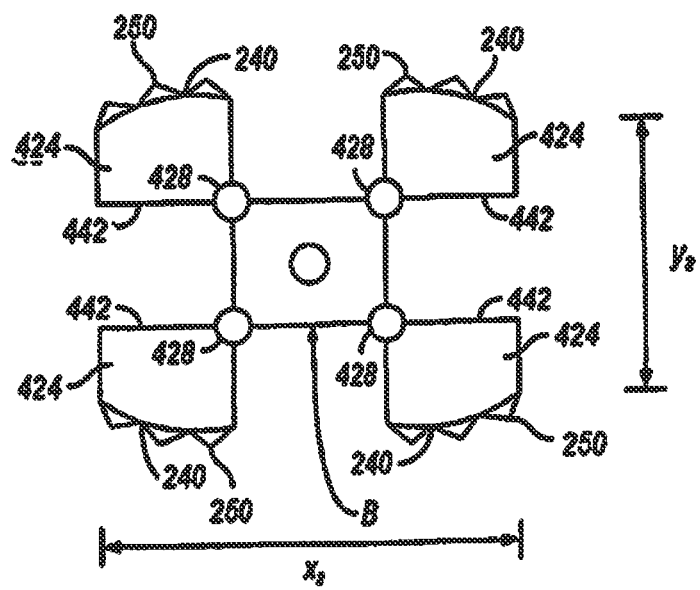
FIG. 34 is an end view of the expandable fusion device of FIG. 32 in an expanded position.

Although the following discussion relates to the first endplate 400, it should be understood that it also equally applies to the second endplate 402, the third endplate 404, and the fourth endplate 406, as these endplates 402, 404, 406 are substantially identical to the first endplate 400 in embodiments of the present invention. Turning now to FIGS. 32-34, in an exemplary embodiment, the first endplate 214 has a first end 424 and a second end 426. The first endplate further includes an upper surface 240 connecting the first end 424 and the second end 426 and a lower surface 442 on an opposing side of the endplate 400 connecting the first end 424 and the second end 426. While not illustrated, the first endplate 214 may include a through opening sized to receive bone graft or similar bone growth inducing material and further allow the bone graft or similar bone growth inducing material to be packed in the central opening 422 in the body portion 212.

In one embodiment, the lower surface 242 includes at least one first retaining socket 428 on the lower surface 242. In an exemplary embodiment, the lower surface 242 includes a first retaining socket 428 at the interior corner of the intersection of the first end 424 and the lower surface 242, and a second retaining socket 430 at the interior corner of the intersection of the first end 424 and the lower surface 242.

Referring now to FIGS. 32-34, in one embodiment, the upper surface 240 of the first endplate 400 is curved convexly. Alternatively, the upper surface 240 is flat or curved concavely to allow for a greater or lesser degree of engagement with the adjacent vertebral body 202. It is also contemplated that the upper surface 240 can be generally planar but includes a generally straight ramped surface or a curved ramped surface. The ramped surface allows for engagement with the adjacent vertebral body 202 in a lordotic fashion. In an exemplary embodiment, the upper surface 240 includes texturing 250 to aid in gripping the adjacent vertebral bodies. Although not limited to the following, the texturing can include teeth, ridges, friction increasing elements, keels, or gripping or purchasing projections.

With reference to FIG. 32, in an exemplary embodiment, the translation member 218 is sized to be received within the central opening 422 of the body portion 212. The translation member 218 should be sized to allow longitudinal translation within the central opening 422. In an embodiment, the translation member 218 includes at least a first expansion portion 252. In another embodiment, the translation member 218 includes a first expansion portion 252 and a second expansion portion 254, the expansion portions 252, 254 being connected together via a bridge portion 256. It is also contemplated that there may be more than two expansion portions where each of the expansion portions is connected by a bridge portion. The expansion portions 252, 254 each have angled surfaces 258, 260. In an embodiment, the angles surfaces 258, 260 each comprise first end 429 and second end 431 with second end 431 being wider than the first end 429. In an exemplary embodiment, the expansion portions 252, 254 include grooved portions 432, 434 on the edges of at least two sides (e.g., the lateral sides) of the angled surfaces 258, 260. The grooved portions 432, 434 are configured and dimensioned to engage the first and second retaining sockets 428, 430 on the endplates 400, 402, 404, 406. In an exemplary embodiment, the grooved portions 432, 434 retain the first and second retaining sockets 428, 430 in sliding engagement.

In one embodiment, the translation member 218 includes a first end 436 and a second end 438. The first end 436 of the translation member includes an extension 440 sized to be received within the opening 420 in the first end 224 of the body portion 212. While not illustrated, the second end 438 also can include a similar extension sized to be received within opening 232 in the second end 226 of the body portion 212.

The expandable fusion device 210 of FIGS. 32-34 can be inserted into the intervertebral space in a manner similar to that the previously described with respect to FIGS. 15-20. After insertion, the expandable fusion device 210 of FIGS. 32-34 can be expanded into the expanded position. As previously mentioned, the fusion device 210 shown on FIGS. 32-34 expands both vertically and laterally. To expand the fusion device 210, the translation member 218 can be moved with respect to the body portion 212 toward the first end 224 of the body portion. An instrument can be used, in an exemplary embodiment. As the translation member 218 moves, the first retaining socket 428 and the second retaining socket 430 ride along the grooved portions 432, 434 of the expansion portions 252, 254 pushing the endplates 400, 402, 404, 406 outwardly in the direction indicated by arrows 442. In an embodiment, the endplates 400, 402, 404, 406 move outwardly in an oblique fashion to expand the fusion device 210 both vertically and laterally. The expanded configuration of the expansion device 210 is best seen in FIG. 34.

After expansion, the expandable fusion device 210 can be contracted back to the unexpanded configuration. The unexpanded configuration of the fusion device 210 is best seen in FIG. 34. To contract the fusion device 210, the translation member 218 is moved with respect to the body portion 212 toward the second end 226 of the body portion 212. As the translation member 218 moves, the first retaining socket 428 and the second retaining socket 430 ride along the grooved portions 432, 434 of the expansion portions 252, 254 pulling the endplates 400, 402, 404, 406 inwardly in a direction opposite that indicated by arrows 442. In an embodiment, the endplates 400, 402, 404, 406 move inwardly in an oblique fashion to contract the fusion device 210 both vertically and laterally. The unexpanded configuration of the expansion device 210 is best seen in FIG. 33.

Figure 35:
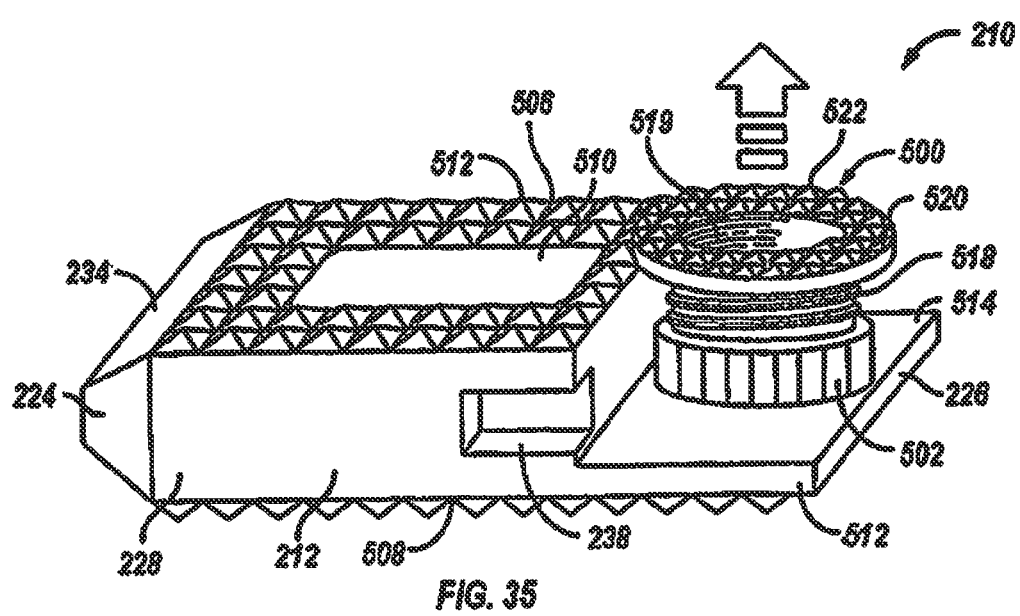
FIG. 35 is a perspective view of another embodiment of an expandable fusion device.
Figure 36:
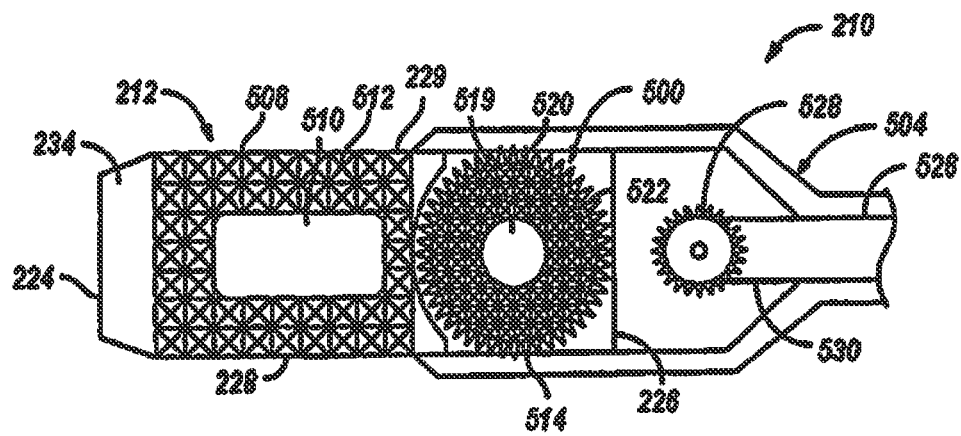
FIG. 36 is a top view of the expandable fusion device of FIG. 35.

With reference to FIGS. 35-36, another embodiment of expandable fusion device 210 is shown. In an exemplary embodiment, the fusion device 210 includes a body portion 212, a vertically expanding plate 500, and a gear 502. In this embodiment, a portion of the fusion device 210 is configured to expand vertically in at least one direction. In an exemplary embodiment, the vertically expanding plate 500 is configured to expand outwardly from the body portion 212. It is contemplated that an expandable fusion device 210 may be used to correct spinal curvature due to, for example, scoliosis, lordosis, and the like.

In an exemplary embodiment, the body portion 212 has a first end 224, a second end 226, a first side portion 228 connecting the first end 224 and the second end 226, and a second side portion 229 on the opposing side of the body portion 212 connecting the first end 224 and the second end 226. The first end 224 of the body portion 212, in an exemplary embodiment, includes at least one angled surface 234, but can include multiple angled surfaces. The angled surface 234 can serve to distract the adjacent vertebral bodies when the fusion device 210 is inserted into an intervertebral space. In another preferred embodiment, it is contemplated that there are at least two opposing angled surfaces forming a generally wedge shaped to distract the adjacent vertebral bodies when the fusion device 210 is inserted into an intervertebral space. In yet another preferred embodiment, first side portion 228 and second side portion 229 each include a recess 238 located towards the second end 226 of the body portion 212. The recess 238 is configured and dimensioned to receive an insertion instrument 504 that assists in the insertion of the fusion device 210 into an intervertebral space.

In an exemplary embodiment, the body portion 212 includes an upper engagement surface 506 extending from the first end 224 towards the second end 226, and a lower engagement surface 508 extending between the first end 224 and the second end 226. In an embodiment, the upper engagement surface 506 has a through opening 510. Although not illustrated, the lower engagement surface 508 may have a through opening that is similar to through opening 510. The through opening 510, in an exemplary embodiment, is sized to receive bone graft or similar bone growth inducing material and further allow the bone graft or similar bone growth inducing material to be packed in the central opening in the body portion 212. In an embodiment, at least a portion of the body portion 212 is removed to form a landing 512 in the body portion 212. In an exemplary embodiment, a portion of the upper engagement surface 506 and the second end 226 are removed to form the landing 512 having an upper surface 514. While not illustrated, a portion of the lower engagement surface 508 and the second end 226 may be cut away, in an alternative embodiment, to form the landing 512.

In one embodiment, the upper engagement surface 506 and the lower engagement surface 508 are flat and generally planar to allow engagement surfaces 506 to engage with the adjacent vertebral body 202 and the lower engagement surface 508 to engage with the adjacent vertebral body 203. Alternatively, the upper engagement surface 506 and/or the lower engagement surface 508 can be curved convexly or concavely to allow for a greater or lesser degree of engagement with the adjacent vertebral bodies 202, 203. In an exemplary embodiment, the upper engagement surface 506 and/or the lower engagement surface includes texturing 512 to aid in gripping the adjacent vertebral bodies. Although not limited to the following, the texturing can include teeth, ridges, friction increasing elements, keels, or gripping or purchasing projections.

In an exemplary embodiment, vertically expanding plate 500 is coupled to an end of threaded bolt 518, which is coupled to the gear 502. In one embodiment, the threaded bolt 518 is in threaded engagement with the gear 502. In an alternative embodiment, a bolt having ratchet teeth may be used instead of threaded bolt 518. In an embodiment, the gear 502 is coupled to the landing 512. In one embodiment, the gear 502 is rotatably coupled to the landing 512.

Figure 37:
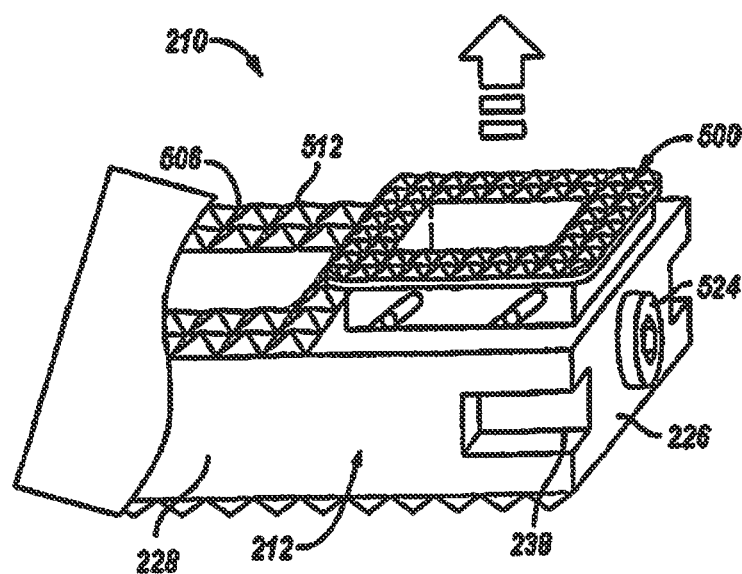
FIG. 37 is a perspective view of the expandable fusion device of FIG. 35 with a closed end.

The vertically expanding plate 500 includes a throughbore 519 and an upper surface 520. In one embodiment, the vertically expanding plate 500 is generally circular in shape. Other suitable configurations of the expanding plate 500 may also be suitable. In an embodiment, the vertically expanding plate may be generally rectangular in shape with rounded corners, as best seen in FIG. 37. In one embodiment, the vertically expanding plate 500 is flat and generally planar to allow upper surface 520 to engage with the adjacent vertebral body 202. Alternatively, the upper surface 520 can be curved convexly or concavely to allow for a greater or lesser degree of engagement with the adjacent vertebral bodies. In an exemplary embodiment, the upper surface 520 includes texturing 522 to aid in gripping the adjacent vertebral bodies. Although not limited to the following, the texturing can include teeth, ridges, friction increasing elements, keels, or gripping or purchasing projections.

With reference to FIG. 37, an alternative embodiment of the expandable fusion device 210 of FIGS. 35-36 is shown. In this embodiment, the gear 502 is enclosed within the body portion 212 towards the second end 226 of the body portion 212 with the vertically expanding plate 500 disposed at or above the upper engagement surface 506 of the body portion 212. In an embodiment, the vertically expanding plate 500 is positioned towards the second end 226 of the body portion 212. While not illustrated, the threaded bolt 518 extends through the upper engagement surface 506 and couples the vertically expanding plate 500 and the gear 502. An actuator screw 524 extends through the first end 224 of the body portion 212 to engage the gear 502.

Figure 38:
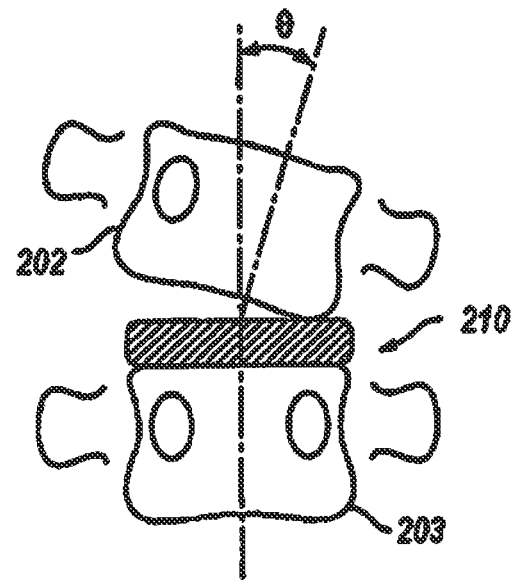
FIG. 38 is a front view of the expandable fusion device of FIG. 37 shown between adjacent vertebrae in an unexpanded position.
Figure 39:
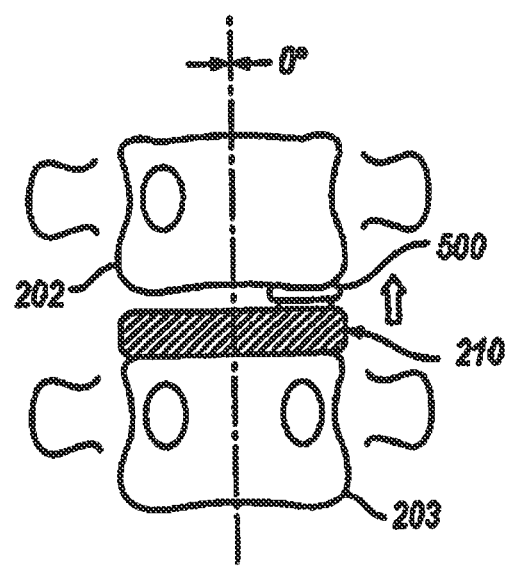
FIG. 39 is a front view of the expandable fusion device of FIG. 37 shown between adjacent vertebrae in an expanded position.

The expandable fusion device 210 of FIGS. 35-37 can be inserted in the intervertebral space in a manner similar to that the previously described with respect to FIGS. 15-20. FIG. 38 illustrates the expandable fusion device 210 of FIG. 37 between adjacent vertebral bodies 202, 203 in an unexpanded position. After insertion, the expandable fusion device 210 of FIGS. 35-37 can be expanded into the expanded position. As previously mentioned, a portion of the fusion device shown on FIGS. 35-37 expands vertically in at least one direction. To partially expand the fusion device 210, the gear 502 can be rotated in a first direction. An instrument 526 having a gear 528 disposed on a distal end 530 of the instrument may be used to rotate the gear 502, as best seen on FIG. 36. In another embodiment, an instrument (not illustrated) may be used to rotate actuation member 524 in a first direction. As discussed above, the actuation member 524 is engaged with gear 502; thus, as the actuation member 524 is rotated in first direction, the gear 502 rotated in a first direction. The embodiment with the actuation member 524 is best seen in FIG. 37. As the gear 502 rotates, the threaded bolt 518 extends outward from the gear 502, thus extending the laterally expanding plate 500 outward from the body portion 212. FIG. 39 illustrates the expandable fusion device 210 of FIG. 37 in an expanded position.

After expansion, the expandable fusion device 210 can be contracted back to the unexpanded position. The unexpanded position of the fusion device 210 is best seen in FIG. 38. To contract the fusion device 210, the gear 502 is rotated in a second direction that is opposite the first direction. The instrument 526 with the gear 528 may be used to rotate the gear 502. Alternatively, an instrument may be used to rotate the actuation member 524 to turn the gear 502 in the second direction. As the gear 502 rotates in the second direction, the threaded bolt 518 retracts pulling the laterally expanding plate 500 inward into the unexpanded position.

In some embodiments, the fusion devices 210 can include additional features that provide additional benefits such as preventing screw loosening and added stability. These embodiments are discussed below.

Figure 40:
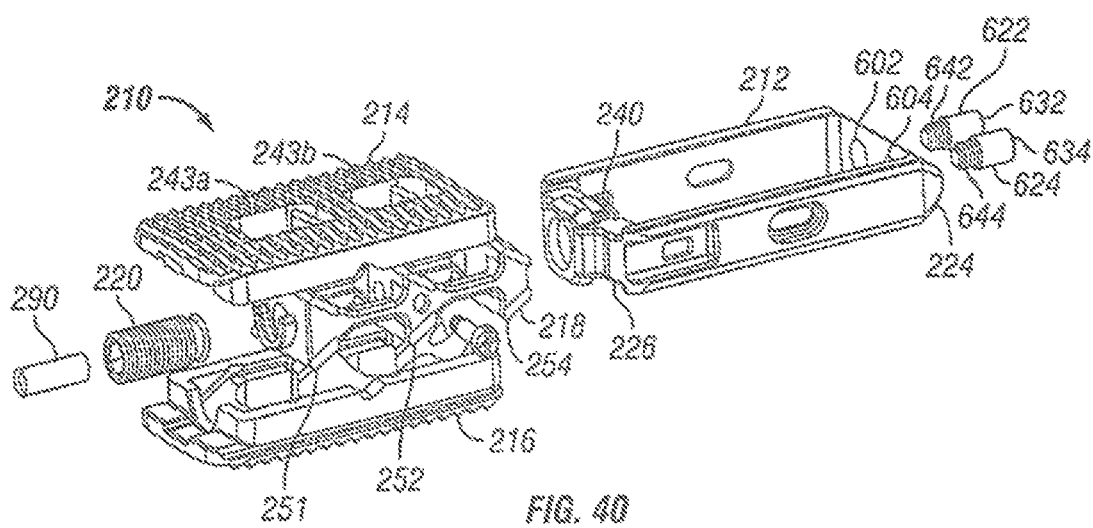
FIG. 40 is an exploded view of an alternative fusion device.
Figure 41:
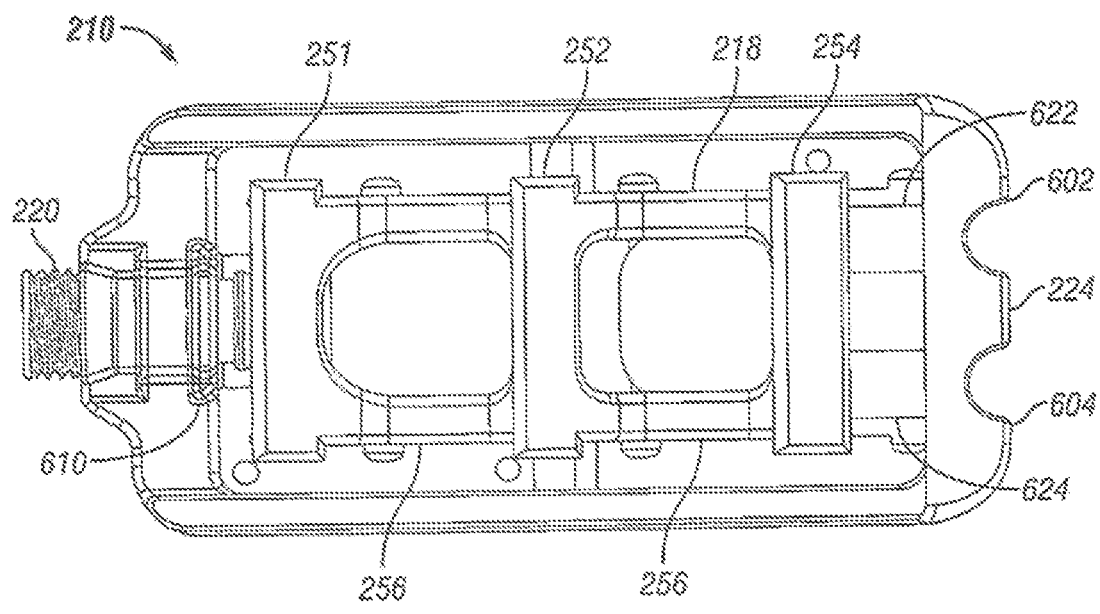
FIG. 41 is a top view of the device in FIG. 40 with a first endplate removed.

FIGS. 40 and 41 show different views of a fusion device 210 including an advantageous interference nut 610 and stabilization members 622, 624 according to some embodiments. The fusion device 210 includes many features similar to the above-described devices, including a body portion 212, a first endplate 214, a second endplate 216, a translation member 218, and an actuation member 220. The first endplate 214 can include a pair of openings 243a and 243b through which bone graft material can be received or deposited. Likewise, the second endplate 16 can have similar openings, although they are not shown from the illustrated viewpoints. In addition to these features, the fusion device 210 includes a novel interference nut 610 that is operably attached to a rear section of the body portion 212, as well as a pair of stabilization members 622, 624.

FIG. 40 illustrates an exploded view of the alternative fusion device 210, while FIG. 41 shows a top view of the same device with the first endplate 214 removed. As shown in both views, the translation member 218 includes three expansion portions 251, 252, and 254, which are connected via bridge portions 256. The expansion portions 251, 252, and 254 each have angled surfaces that are configured to engage grooved portions of the first and second endplates 214 and 216. In some embodiments, the angled surfaces are of similar angles, while in other embodiments, the angled surfaces are of different angles. Advantageously, by providing at least three expansion portions 251, 252 and 254, this allows for an even expansion along a majority of the length of the body portion 212 of the fusion device 210.

The translation member 218 is received in the central opening of the body portion 212. The body portion 212 can include a first end 224 and a second end 226. In some embodiments, the first end 224 includes one or more apertures 602, 604 as shown in FIGS. 40 and 41. These apertures 602, 604 advantageously receive one or more stabilization members 622, 624.

In some embodiments, the stabilization members 622, 624 each include a first substantially smooth portion 632, 634 and a second threaded portion 634, 644. The stabilization members 622, 624 can be inserted through the apertures 602, 604 of the body portion 212, with the threaded portions 634, 644 serving as the leading end that enters the apertures. After passing through the apertures 602, 604 of the body portion 212, the stabilization members 622, 624 can come into contact with a side of the translation member 218. In some embodiments, the threaded portions 634, 644 of the stabilization members 622, 624 can be threaded into mateable threaded surfaces of the translation member 218. Advantageously, by using a pair of stabilization members 622, 624 as shown in FIGS. 40 and 41 on a first end of the body portion 212, this serves to prevent rocking of the body portion 212 during expansion and contraction of the device 210.

While the illustrated embodiment in FIGS. 40 and 41 show a pair of stabilization members 622, 624, in other embodiments, a single stabilization member or more than two stabilization members can be used to assist in preventing rocking of the body portion 212. In addition, while the stabilization members 622, 624 are illustrated as having a substantially cylindrical surface section, in other embodiments, the stabilization members 622, 624 can assume other shapes and geometries. For example, in other embodiments, the stabilization members 622, 624 can have a surface that includes at least one edge or corner.

As shown in FIGS. 40 and 41, the body portion 212 also includes an interference nut 610 that is positioned within a rear section of the body portion 212. In some embodiments, the interference nut 610 is separate and removable from the body portion 212, while in other embodiments, the interference nut 610 is not removable from the body portion 212. In some embodiments, the interference nut 610 comprises a square nut that is operably connected to a rear section of the body portion 212. The interference nut 610 can be mateably connected to a rear of the body portion 212, for example, via a dove-tail type cut that encapsulates the interference nut. The interference nut 610 can be advantageously formed of a biocompatible material. In some embodiments, the interference nut 610 is formed of PEEK.

The interference nut 610 can include a hole (not shown) that is capable of receiving the actuation member 220 therethrough. The actuation member 220, which can comprise a threaded set screw, passes through the interference nut 610 and into contact with the translation member 218, as best shown in FIG. 41. Advantageously, the interference nut 610 serves to add drag to the actuation member 220 as it passes therethrough, thereby establishing an interference fit. By providing an interference fit, the risk of the actuation member 220 being loosened prior to or during use is minimized.

Figure 42:
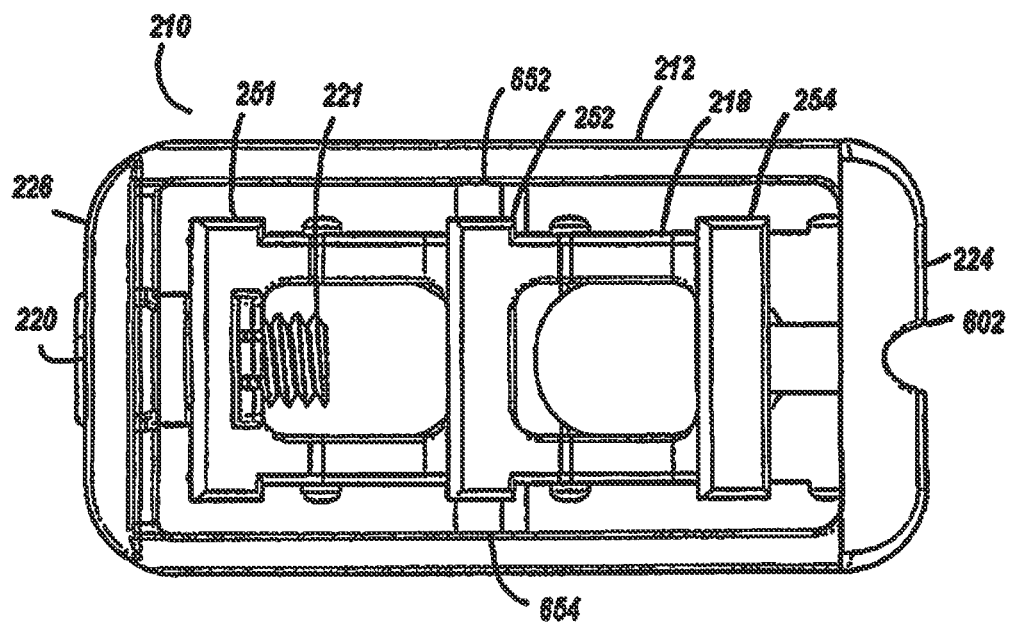
FIG. 42 is a top view of the alternative fusion device having side stabilization members.
Figure 43:
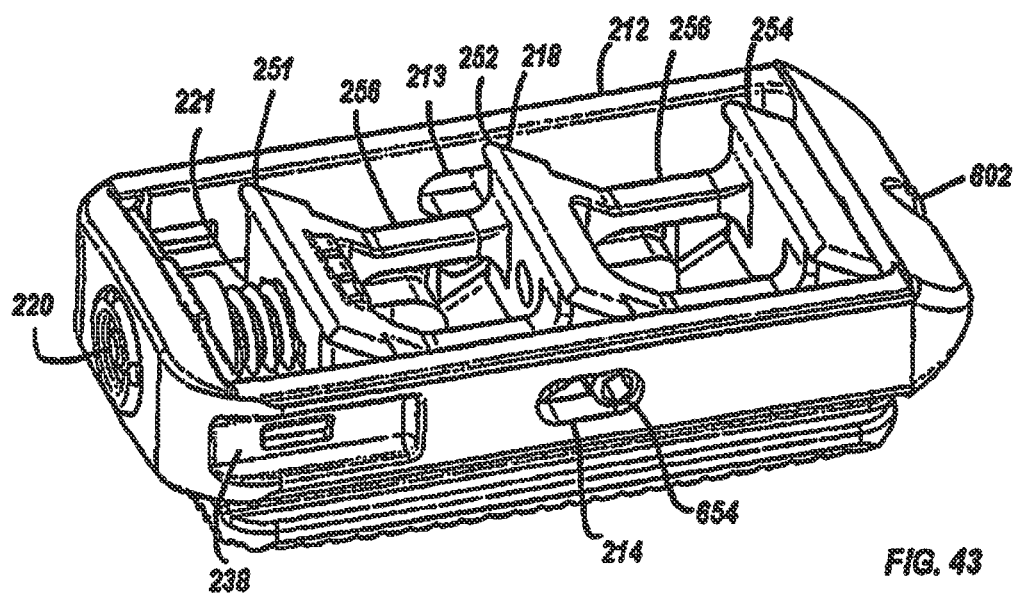
FIG. 43 is a perspective view of the device in FIG. 42.
Figure 44:
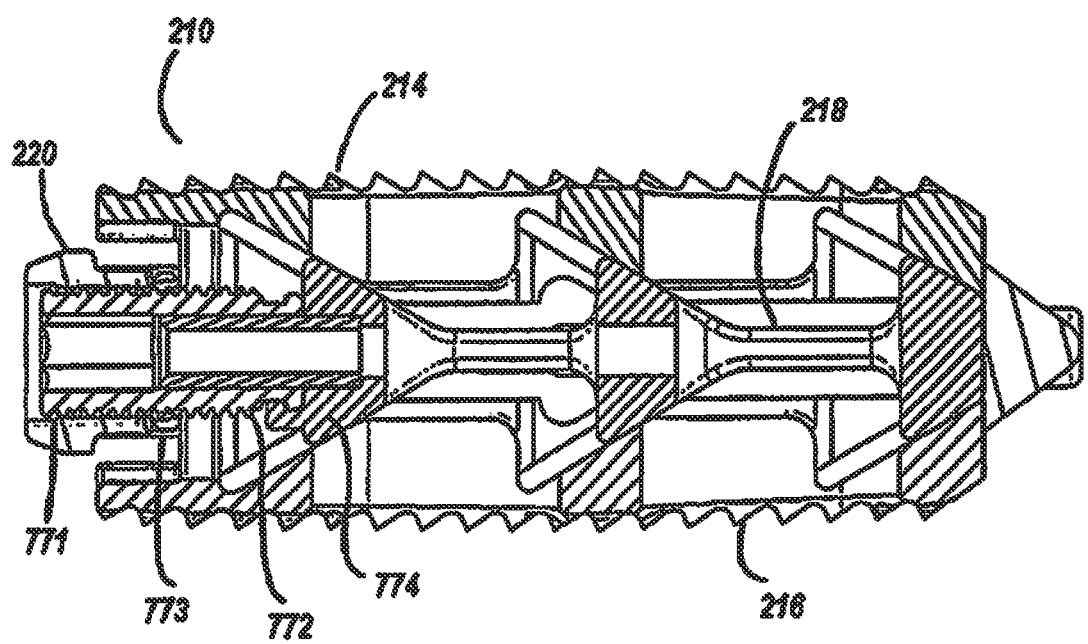
FIG. 44 is a side cross-sectional view of the device in FIG. 42.

FIGS. 42-44 show different views of an alternative fusion device 210 including novel side stabilization members 652, 654 and a low profile actuation member 220. The fusion device 210 includes many features similar to the above-described devices, including a body portion 212, a translation member 218, and an actuation member 220. The fusion device 210 can also include a first endplate 214 and a second endplate 216 for contacting vertebral surfaces, as best shown in FIG. 44. Both the first endplate 214 and second endplate 216 can include a pair of openings through which bone graft material can be received or deposited. In addition to these features, the fusion device 210 includes novel side stabilization members 652, 654 that are introduced through side slots 213 and 214 of the body portion 212. The fusion device 210 also includes a configuration that allows the actuation member 220 to be of low profile, as shown in FIG. 42.

FIG. 42 illustrates a top view of the alternative fusion device 210 having side stabilization members with the first endplate 214 removed, while FIG. 43 illustrates a perspective view of the same device. FIG. 44 illustrates a side cross-sectional view of the alternative fusion device 210 having side stabilization members. As shown in all three views, the translation member 218 includes three expansion portions 251, 252, and 254, which are connected via bridge portions 256. The expansion portions 251, 252, and 254 each have angled surfaces that are configured to engage grooved portions of the first and second endplates 214 and 216. In some embodiments, the angled surfaces are of similar angles, while in other embodiments, the angled surfaces can be of different angles. Advantageously, by providing at least three expansion portions 251, 252 and 254, this allows for an even expansion along a majority of the length of the body portion 212 of the fusion device 210.

The translation member 218 is received in the central opening of the body portion 212. The body portion 212 can include sidewalls that extend between the first end 224 and a second end 226. As shown in FIG. 43, each of the sidewalls can include side slots 213, 214 for receiving one or more side stabilization members 652, 654.

In some embodiments, the side stabilization members 652, 654 are similar to the stabilization members 622, 624 (shown in FIG. 40). That is, the side stabilization members 652, 654 can include a threaded portion and a substantially smooth portion. The side stabilization members 652 can be inserted through the side slots 213, 214 of the body portion 212 and can operably attach (e.g., via threads) to the translation member 218. Advantageously, the side slots 213, 214 help to provide rotational stability to the translation member 218 relative to the body portion 212 prior to or during use of the fusion device 210.

In addition to providing side stabilization members, the fusion device 210 provides a configuration that includes a low profile actuation member 220. Advantageously, as shown in FIG. 42, the actuation member 220 (which can comprise a screw) can have a head portion that is substantially flush against the surface of the body portion 212, while a distal portion 221 of the actuation member 220 can extend through a wall of the translation member 218.

As shown in FIG. 44, in some embodiments, the actuation member 220 can comprise a set screw 772 accompanied by a flange 773 and an actuation element 774. The set screw 772 and actuation element 774 can both be threaded. Upon rotation of the set screw 772, the actuation element 774 is threaded forward, thereby pushing the first endplate 214 upwardly and the second endplate 216 downwardly to cause expansion of the actuation member 220. The flange 773, which can be cylindrical, advantageously resists the opposing forces as the actuation element 774 is threaded forward, thereby helping to keep the fusion device 210 in an expanded configuration. Upon reverse rotation of the set screw 772, the fusion device 210 can collapse. As shown in FIG. 44, a blocking nut 771 can be provided that is threaded onto the back side of the set screw 772 to secure the set screw into place when the device 210 is collapsed.

Figure 49:
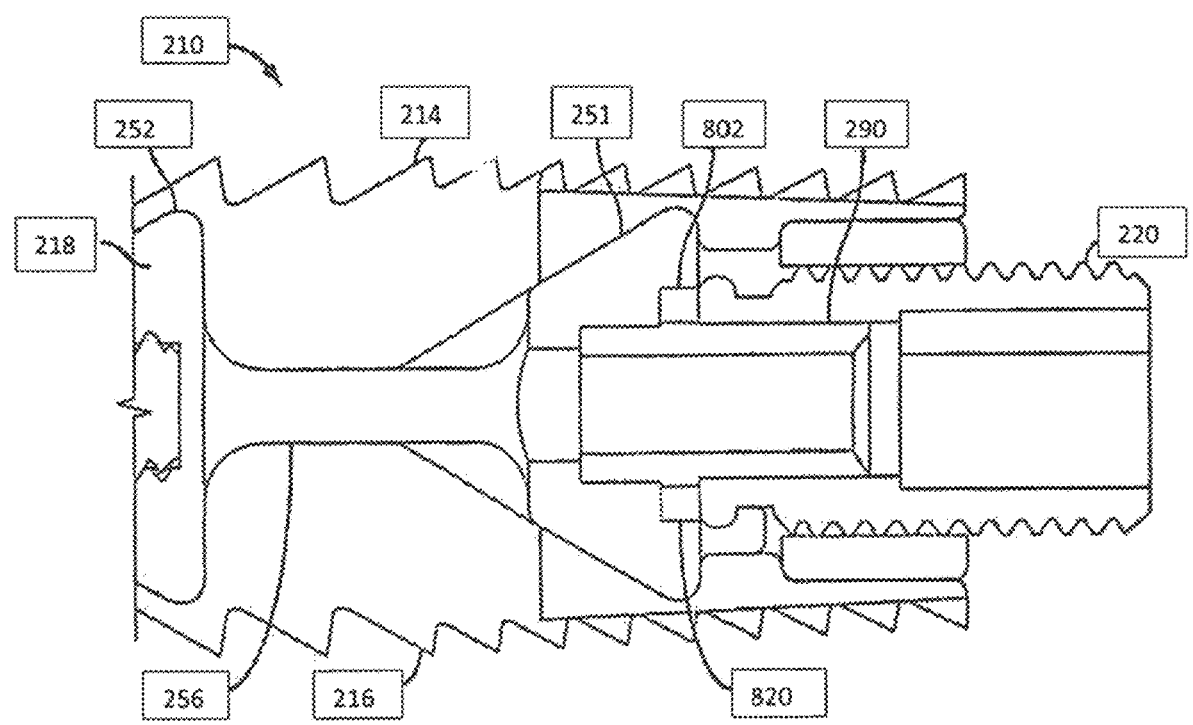
FIG. 49 is a side cross-sectional view of a portion of an alternative fusion device incorporating a ring member therein.
Figure 50:
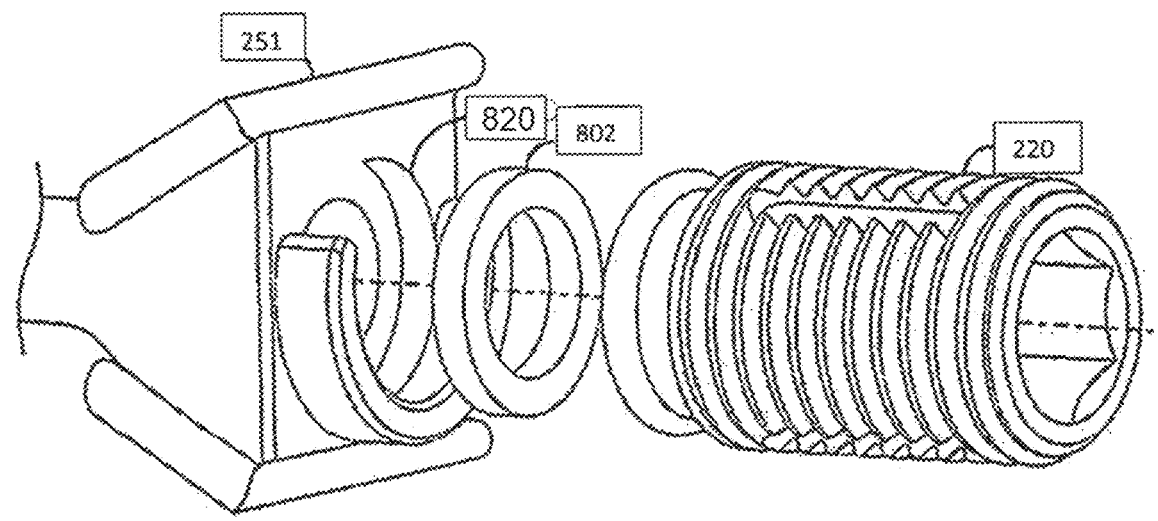
FIG. 50 is a perspective view of a portion of the alternative fusion device of FIG. 49.

Additional embodiments of an expandable fusion device 210 are shown in FIGS. 49 and 50. This fusion device 210 incorporates a ring member 802 into a pocket 820 formed in the translation member 218.

The fusion device 210 in FIGS. 49 and 50 include many features similar to the above-described devices, including a body portion 212, a first endplate 214, a second endplate 216, a translation member 218, an actuation member 220, and a pin member 290. The first endplate 214 can include one or more openings through which bone graft material can be received or deposited. Likewise, the second endplate 216 can have similar openings, although they are not shown from the illustrated viewpoints. The translation member 218 can be comprised of one or more ramped expansion portions, such as expansion portions 251 and 252, which are configured to assist in expansion and contraction of the fusion device 210, as discussed above.

In addition to these features, the fusion device 210 incorporates a ring member 802 that is positioned between the actuation member 220 and the translation member 218. In some embodiments, the ring member 802 is received in a pocket 820 that is formed in one of the expansion portions (such as expansion portion 251) of the translation member 218. As shown in FIG. 50, the ring member 802 can comprise a closed annular body that can be received in a similarly shaped recess 820 formed in the body of an expansion portion 251 of the translation member 218. Each of expansion portion 251, ring member 802 and actuation member 220 can be placed over a pin member 290.

In some embodiments, the ring member 802 can be formed of a material that is different from the translation member 218 and/or actuation member 220. For example, while in some embodiments the translation member 18 and/or actuation member 220 are comprised of a metal, such as a biocompatible stainless steel, titanium or metal alloy, the ring member 802 can be formed of a polymer such as polyether ether ketone (PEEK). The advantage of providing a PEEK ring member 802 is that a more lubricious material is positioned between the face of the actuation member 220 and the surface of the translation member 218, thereby reducing the friction between the two parts. With the PEEK ring member's 802 reduced coefficient of friction, this increases the amount of force transmitted when the actuation member 220 is screwed into the translation member 218, thereby increasing the amount of expansion force provided to the ramped translation member 218. In some embodiments, the use of a PEEK ring member between the interface of the actuation member 220 and translation member 218 increases the expansion force of the ramped translation member 218 while using the same force as would be applied if the PEEK ring member was not in place. In some embodiments, the use of a PEEK ring member between the translation member 218 and actuation member 220 provides a buffer that can prevent galling that would occur due to metal-on-metal contact between the translation member and actuation member.

In some embodiments, rather than receive an insert in the shape of ring member 802, the translation member 218 can receive an insert having a different shape. For example, the translation member 218 can include one or more recesses that accommodate a wedge-shaped PEEK member between the translation member 218 and the actuation member 220. Like the ring member 802, the wedge-shaped PEEK member can also serve as a lubricious material that reduces the friction between the translation member 218 and the actuation member 220.

In addition, in some embodiments, an insert can be placed between the translation member 218 and actuation member 220 without having to form a recess in the translation member. For example, a PEEK washer can be provided between the interface of the translation member 218 and actuation member 220.

Although the preceding discussions only discussed having a single fusion device 210 in the intervertebral space, it is contemplated that more than one fusion device 210 can be inserted in the intervertebral space. It is further contemplated that each fusion device 210 does not have to be finally installed in the fully expanded state. Rather, depending on the location of the fusion device 210 in the intervertebral disc space, the height of the fusion device 210 may vary from unexpanded to fully expanded.

In some embodiments, the fusion devices 210 can be put into place with the assistance of a novel expandable trial member. The expandable trial member can be used prior to inserting an expandable fusion device in between vertebral bodies to obtain an accurate size measurement for the fusion device. The expandable trial member can help a user determine a fusion device of an appropriate size to use in a vertebra. Advantageously, the novel expandable trial member disclosed herein is configured such that the amount of distraction force applied to the trial member is linear and constant over its entire expansion range.

Figure 45:
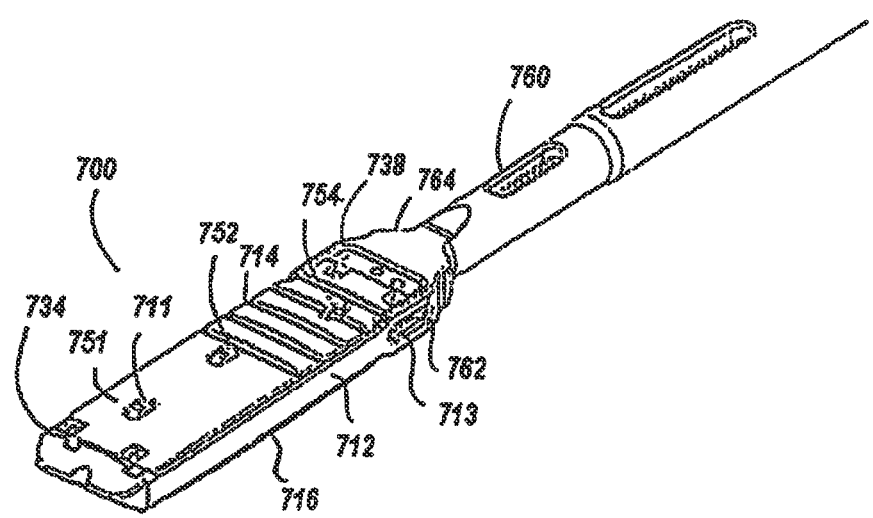
FIG. 45 is a perspective view of a trial member in a non-expanded configuration.
Figure 46:
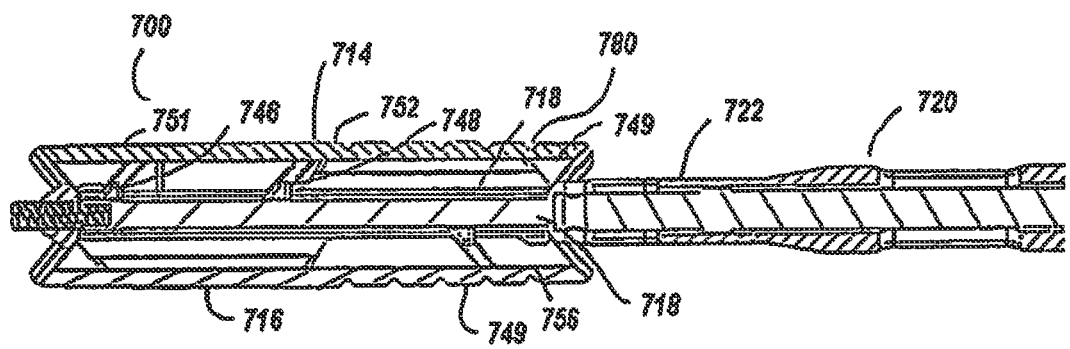
FIG. 46 is a side cross-sectional view of the trial member of FIG. 45 in an expanded configuration.
Figure 47:
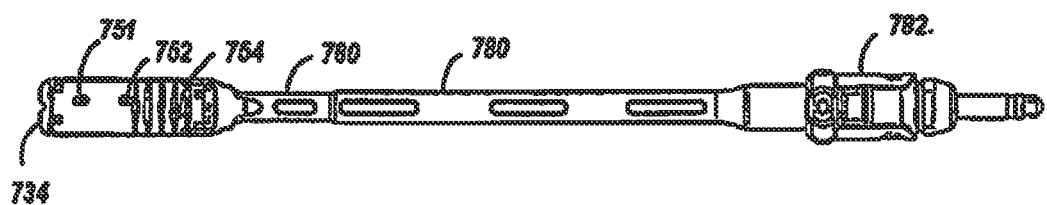
FIG. 47 is a top view of the trial member.
Figure 48:
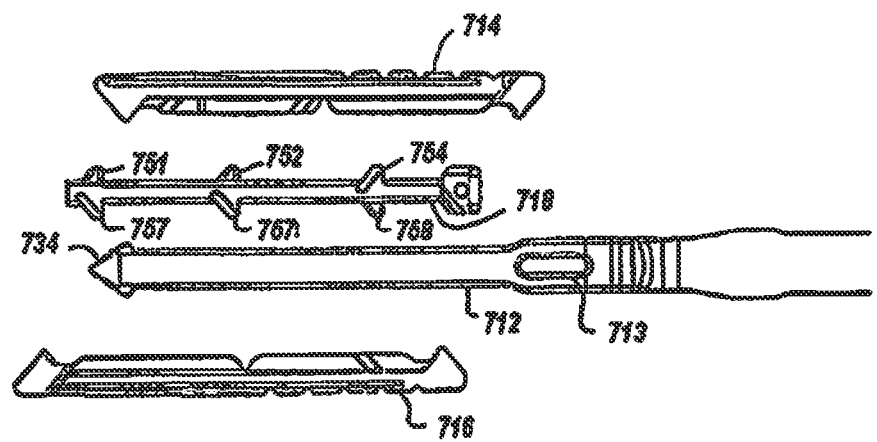
FIG. 48 is an exploded view of the trial member.

FIGS. 45-48 show different perspectives of an expandable trial member according to some embodiments. FIG. 45 illustrates a perspective view of the trial member in a non-expanded configuration. FIG. 46 illustrates a side cross-sectional view of the trial member in an expanded configuration. FIG. 47 illustrates a top view of the trial member. FIG. 48 shows an exploded view of the trial member.

As shown in the figures, the expandable trial member 700 comprises a body portion 712, an upper endplate 714, a lower endplate 716, a translation member 718 and an actuation member 720. The trial member 700 is configured such that when the actuation member 720 (shown in FIG. 46) is pulled in a backward or proximal direction toward a handle portion 782 (shown in FIG. 47), inner shaft or rod member 722 (shown in FIG. 46) will push forward and cause inner ramped surfaces of the translation member 718 to translate relative to inner angled grooves cut into the upper endplate 714 and/or lower endplate 716, thereby causing expansion of the trial member 700. When the actuation member 720 is pushed in a forward or distal direction away from the handle portion 782, the trial member 700 can collapse. In other embodiments, distal movement of the actuation member 720 can result in expansion of the expandable trial member, while proximal movement of the actuation member 720 can result in collapse of the trial member. The configuration of the trial member 700 thus allows pushing and pulling of the actuation member 720 to actuate the shaft or inner rod 722, thereby causing expansion or contraction of the trial member 700. Advantageously, because movement along the ramped surfaces of the upper endplate 714 and lower endplate 716 cause expansion or contraction, the amount of distraction force is linear over the entire expansion range of the trial member 700.

The expandable trial member 700 includes an upper endplate 714 and a lower endplate 716. As shown best in FIG. 46, both the upper endplate 714 and lower endplate 716 can include one or more surface grooves 780. While the trial member 700 need not remain over an extended period of time within a vertebra, the surface grooves 780 advantageously help to retain the trial member 700 within a vertebra during its operational use.

A body portion 712 can be placed in between the upper endplate 714 and lower endplate 716. The body portion 712 can include a sloped or chamfered anterior portion 734 (shown in FIG. 45) that assists in distraction of vertebral bodies.

Within the body portion 712, the translation member 718 can be received therein. As shown best in FIG. 48, the translation member 718 includes a plurality of upper ramped surfaces 751, 752 and 754 and a plurality of lower ramped surfaces 756, 757 and 758. As shown in FIG. 45, the upper and lower endplates 714 and 716 can include one or more holes 711 that accommodate the upper and lower ramped surfaces when the trial member 700 is in a closed configuration. The upper ramped surfaces and lower ramped surfaces are configured to slidably mate with corresponding grooves (such as upper grooves 746 and 748 and lower groove 749 shown in FIG. 46). When the actuation member 720 is pulled distally, the upper ramped surfaces slide downwardly through the grooves and the lower ramped surfaces slide upwardly through the grooves, thereby causing the expandable trial member 700 to expand from its closed configuration, shown in FIG. 45, to an expanded configuration, shown in FIG. 46.

In some embodiments, the body portion 712 can include a pair of side slots 713, as shown in FIG. 45. The side slots 713 are configured to each receive a side stabilization member 762. In some embodiments, the stabilization members 762 comprise stabilizer screws that contact the translation member 718. Advantageously, the stabilization members 762 help keep the translation member 718 centered inside the body portion 712 to prevent twisting as it translates forward and backwards.

In some embodiments, the trial member 700 is configured to expand to have a trial height that is at least fifty percent higher than a height of the trial member 700 in its closed configuration. In other embodiments, the trial member 700 is configured to expand to have a trial height that is at least two times the height of the trial member 700 in its closed configuration. By having a trial member 700 with a wide variety of expansion configurations, a user can advantageously choose a properly sized fusion implant to accommodate a number of different patients of different sizes.

FIGS. 51-55 show different views of some embodiments of a proximal portion 750 of a trial member 700. In some embodiments, the trial member 700 can be a single piece that extends from a proximal end to a distal end. In other embodiments, which are reflected in FIGS. 51-55, the proximal portion 750 can comprise a removable handle portion 782 that is configured to operably attach to a body of the trial member 700. Advantageously, by providing a removable handle portion 782, this helps to facilitate easier cleaning of the trial member 700. The proximal portion 750 is configured to assist in movement of the inner shaft 722 of the trial member, thereby causing expansion and contraction of the trial member upper and lower endplates. In addition, the proximal portion 750 can comprise a novel locking member that operably mates the proximal portion 750 to the inner shaft 722, thereby allowing the inner shaft 722 to be pulled back. Once the upper and lower endplates of the trial member are separated a desired distance, the trial member 700 can be removed, and an appropriately sized expandable implant can be inserted based on the separation distance between the upper and lower endplates.

Figure 51:
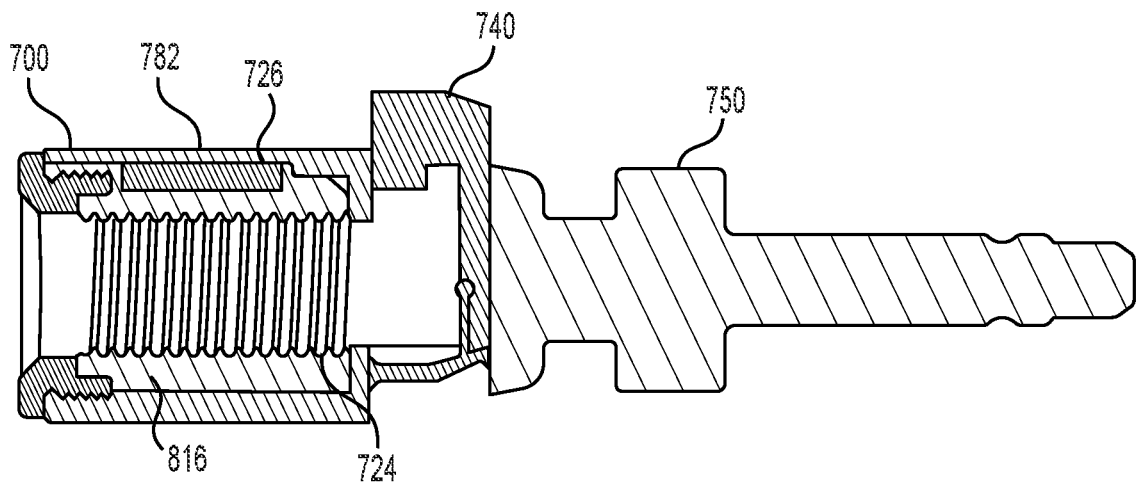
FIG. 51 is a side cross-sectional view of a proximal portion of a trial member in an unlocked configuration.

In the trial member 700 shown in FIG. 51, the removable proximal portion 750 is configured to operably attach to a body of the trial member (such as shown in FIG. 47). The proximal portion 750 is comprised of a handle 782 in the form of a housing member, a removable engagement insert 816, and a slidable locking member 740. The interior of the proximal portion 750 is configured to have a threaded insert 816 that mates with an exterior threaded surface 724 along the body of the trial member 700. As the proximal portion 750 is rotatably threaded onto the body portion, a surface of the slidable locking member 740 pushes against the inner shaft 722 (shown in FIG. 53 as within the exterior threaded surface 724), thereby causing expansion of the trial member endplates.

Figure 54:
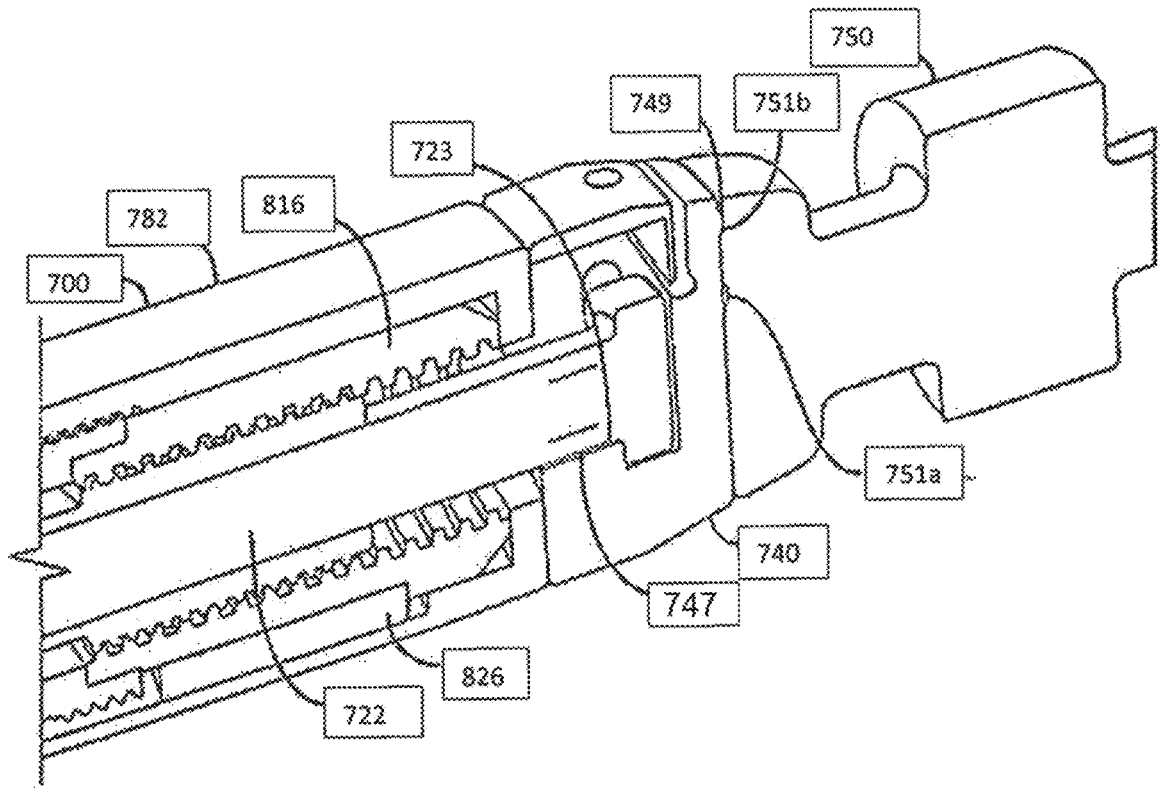
FIG. 54 is a perspective cross-sectional view of a proximal portion of a trial member in a locked configuration.
Figure 55:
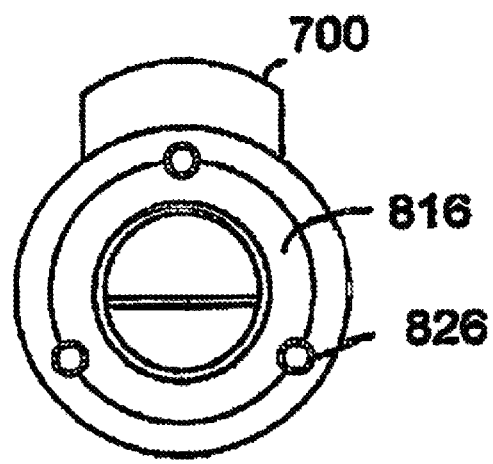
FIG. 55 is a front cross-sectional view of a proximal portion of a trial member.

The body of the handle portion 782 is configured to receive a threaded insert 816 therein. While in some embodiments, the threaded insert 816 is comprised of the same material as the exterior threaded surface 724 of the body, in other embodiments, the threaded insert 816 and threaded surface 724 are of different materials. For example, in some embodiments, the threaded insert 816 can be a polymer, such as PEEK, while the exterior threaded surface 724 can be a metal, such as stainless steel. One skilled in the art will appreciate that other materials can also be used. By providing a PEEK insert 816 that threads onto the metal threads, this advantageously reduces the friction between the two components, thereby reducing the amount of work that is absorbed by the two components and increasing the expansion forces transmitted to the endplates. In addition, the use of a threaded PEEK insert 816 on metal prevents thread galling over multiple uses under high loading. To prevent rotation of the insert 816, pin members 826 can be provided to contact the surface of the insert 816 along with the inner wall of the handle portion 782 (as shown in FIG. 54). As shown in FIG. 55, a plurality of pin members 826 can be provided that align with the longitudinal axis of the insert 816 to prevent rotation of the insert 816.

As the insert 816 of the removable proximal portion 750 is rotatably threaded onto the exterior threads of the body of the trial member, a surface of the slidable locking member 740 pushes against the inner shaft 722 of trial member, thereby causing expansion of the endplates. Reverse rotation of the threads of the insert 816 will result in contraction of the endplates. In some embodiments, the slidable locking member 740 can be moved from an unlocked to a locked configuration such that the inner shaft 722 is operably mated with the proximal portion 750 via the locking member 740. More details regarding the slidable locking member 740 are discussed below.

FIG. 39 illustrates the proximal portion 750 of the trial member with the slidable locking member 740 in an unlocked configuration, while FIG. 54 illustrates the proximal portion 750 of the trial member with the slidable locking member 740 in a locked configuration. In the unlocked configuration, the proximal portion 750 is able to translate along the body of the trial member, thereby pushing on the inner shaft 722 and causing expansion of the trial member endplates. In the locked configuration, the proximal portion 750 is operably mated to the inner shaft 722, thereby allowing the inner shaft 722 to be pulled back via the proximal portion 750 in situ.

Figure 52:
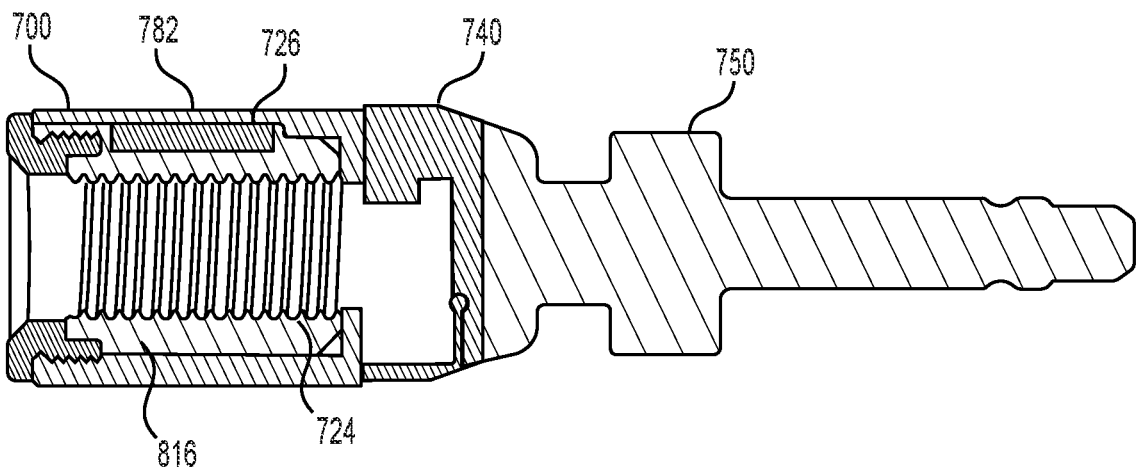
FIG. 52 is a side cross-sectional view of a proximal portion of a trial member in a locked configuration.
Figure 53:
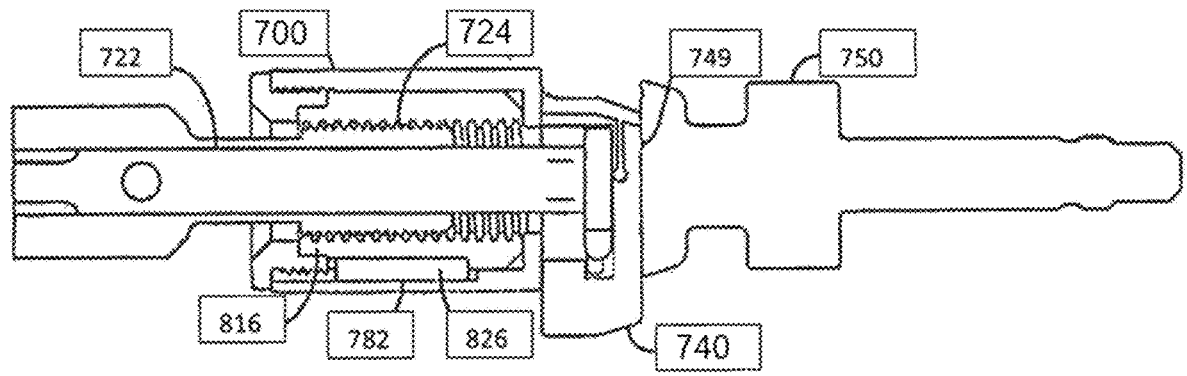
FIG. 53 is an alternate side cross-sectional view of a proximal portion of a trial member in a locked configuration.

The slidable locking member 7540 comprises an insert attached to the proximal portion 750 of the trial member. In some embodiments, the locking member 740 comprises a J-shaped or hook-shaped body that is configured to slide up and down in order to provide unlocked and locked configurations, as shown in FIGS. 51 and 52 respectively. The body of the locking member 740 can include a nub 749 (identified in FIGS. 53 and 54) that can be received in a snap-fit into corresponding grooves 751a and 751b formed in the proximal portion 750. When the nub 749 is in groove 751a, the locking member 740 is in an unlocked configuration. When the nub 749 is in groove 751b, the locking member 740 is in a locked configuration.

As shown in FIG. 54, the hook-shaped body of the locking member 740 also includes a mating end 747 that can be received in a complementary mating portion 723 of the inner shaft 722. When the mating end 747 is received in the mating portion 723 of the inner shaft 722, this advantageously mates the proximal portion 750 to the inner shaft 722, thereby allowing the inner shaft 722 to be pulled back in situ if desired.

In some embodiments, the locking member 740 is of the same material as surfaces of the proximal portion 750 and/or the inner shaft 722. In other embodiments, the locking member 740 is of a different material from surfaces of the proximal portion 750 and/or the inner shaft 722. For example, the locking member 740 can be formed of a polymer such as PEEK, while an adjacent surface of the proximal portion 750 is a metal such as stainless steel. By providing a locking member 740 that is of a lubricious material such as PEEK, this advantageously reduces the friction between the locking member 740 and adjacent surfaces, thereby resulting in less galling between adjacent surfaces.

Various methods are provided for utilizing fusion devices and trial members are provided. In some embodiments, a cavity is formed in a vertebral space between two vertebrae. An expandable trial member including a first endplate, a second endplate, a translation member with ramped surfaces, a body portion and an actuation member can be provided. In an unexpanded form, the trial member can be introduced into the vertebral space. Once in the vertebral space, the actuation member can be rotated, thereby causing expansion of the first endplate and second endplate via motion of the translation member. With the trial member in the vertebral space, an assessment can be made as to the proper size of an expandable fusion device.

Once the trial member is removed, an expandable fusion device comprising a first endplate, a second endplate, a translation member with ramped surfaces, a body portion and an actuation member can be provided. Optionally, the trial member can include an interference nut that is attached to a rear section of the body portion, one or more front or side stabilization members, a flange, a blocking nut, or combinations thereof. The expandable fusion device can be inserted into the vertebral space in an unexpanded form. Once in the vertebral space, the actuation member of the fusion device can be rotated, thereby causing expansion of the first endplate and second endplate via motion of the translation member. Once in its expanded form, the fusion device is kept in place and can remain in the vertebral space for an extended period of time.

In some embodiments, an instrument can be provided to deliver and actuate a fusion device as described above. Advantageously, the instrument can hold or grasp the fusion device to assist in inserting the fusion device in a desired location within a vertebral space. In addition, the instrument can advantageously be cannulated to provide a space for a driver to actuate or expand the fusion device. While the instrument is described with respect to any of the fusion devices described above, one skilled in the art will appreciate that the instrument should not be limited to these specific devices, and that the benefits of any instrument described herein can be used with respect to other implants as well.

Figure 56:
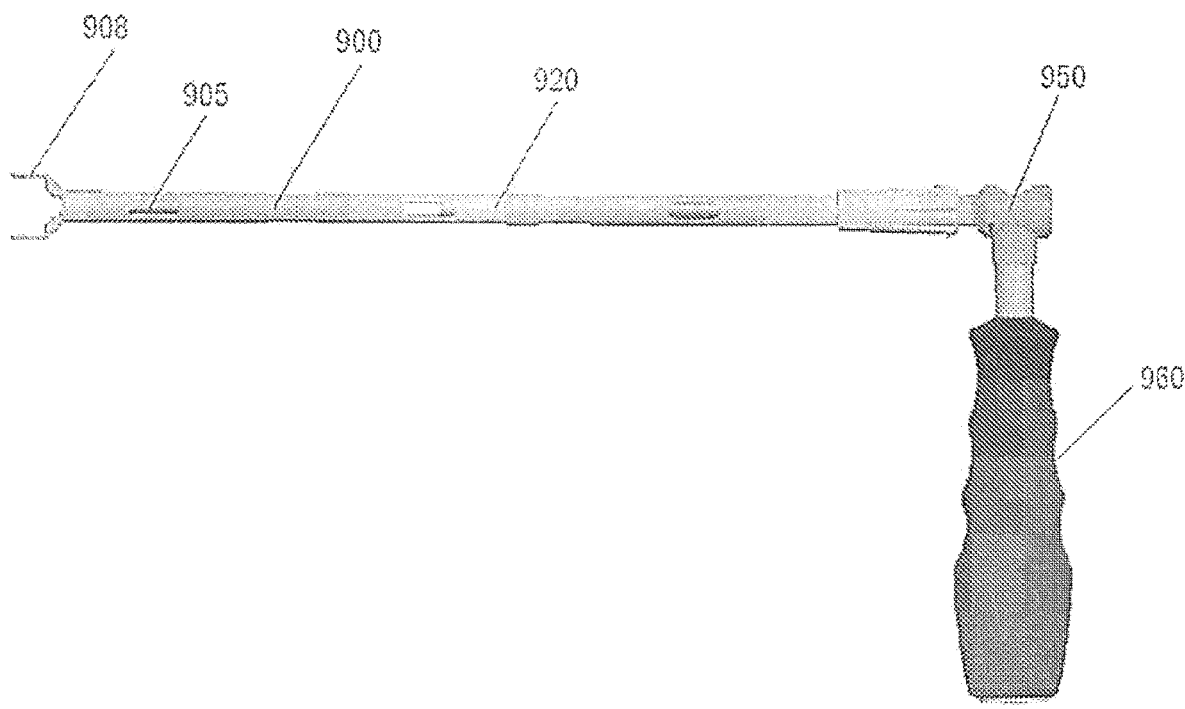
FIG. 56 is a side view of an instrument for engaging a fusion device.

FIG. 56 illustrates an instrument for delivering and actuating a fusion device. In some embodiments, the instrument 900 includes an inserter tube 920, an inserter fork 905 having gripping fingers 908 that is slidable relative to the inserter tube 920, a coupler 950 and a handle 960. The instrument 900 is advantageously capable of both gripping a fusion device for insertion, and providing a driver therethrough to actuate (e.g., expand or contract) the fusion device. In addition, each of the components—the inserter fork, inserter tube, coupler and handle—can be removed from another in order to facilitate easy cleaning. More details regarding the components of the instrument 900 are discussed below.

Figure 57A:
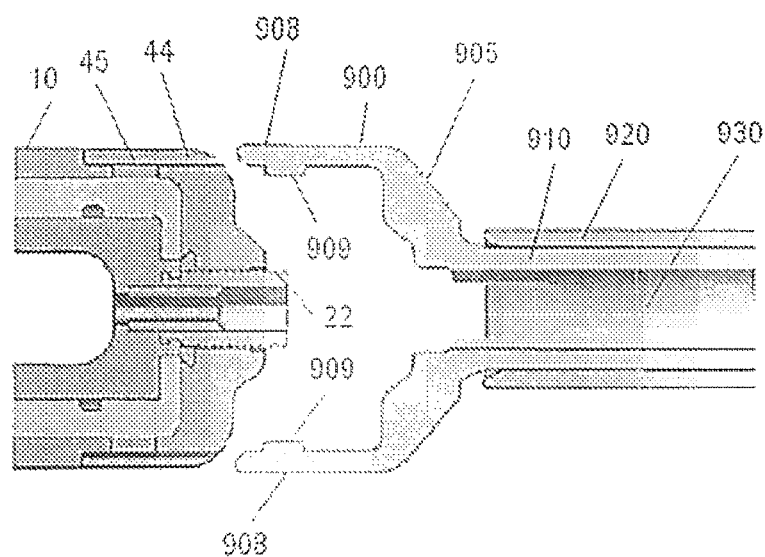
FIGS. 57A-57C illustrate a distal portion of an instrument in the process of engaging a fusion device for delivery and actuation.
Figure 57B:
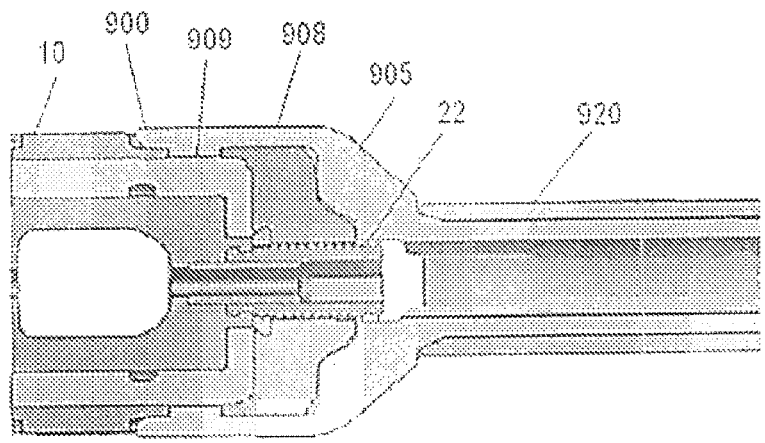
Figure 57C:
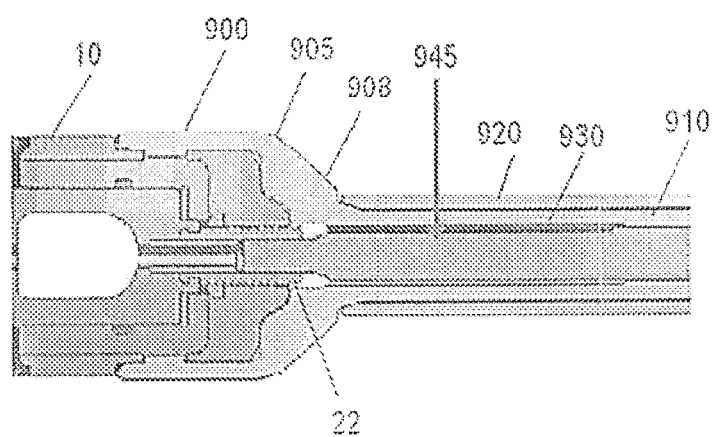

FIGS. 57A-57C illustrate a distal portion of an instrument in the process of engaging a fusion device for delivery and actuation. The instrument 900 comprises an inserter fork 905 having tines or fingers 908 that can hold or grasp a portion of the fusion device 10. The inserter fork 905 slides relative to an inserter tube 920, thereby causing the fingers 908 to close or open to either grip or release the fusion device 10.

As shown in FIGS. 57A-57C, the instrument 900 comprises an inserter fork 905 for engaging and gripping recessed surfaces 44 on the fusion device 10. The inserter fork 905 comprises fingers 908 for holding the fusion device 10. In some embodiments, the fingers 908 can include additional protrusions 909 that can be fitted into scalloped or deepened recessed surfaces 45 formed on the sides of the fusion device. The added protrusions 909 can advantageously help to further secure the fingers 908 to the fusion device 10. In other embodiments, the additional protrusions 909 on the fingers 908 are absent. The fingers 908 on the inserter fork 905 are formed on a distal portion of the instrument 900.

In some embodiments, the fingers 908 extend distally from a shaft portion 910 of the inserter fork 905. The shaft portion 910 surrounds and encloses an inner space or lumen 930, through which a driver can be inserted to expand and contract the fusion device 10. As discussed in more detail below, the instrument 900 can thus hold the fusion device 10 in place and deliver a driver to expand the fusion device 10 in a convenient fashion.

The inserter fork 905 can slide distally and proximally relative to an inserter tube 920, thereby causing the fingers 908 to open and close. FIG. 57A illustrates the fingers 908 of the inserter fork in an "open" configuration, in which the fingers 908 are capable of receiving the fusion device 10 therebetween. FIG. 57B illustrates the fingers 908 of the inserter fork in a "closed" configuration, in which the fingers 908 have clamped down on the fusion device 10. To move the inserter fork 905 from the open to closed configuration, the inserter fork 905 can slide proximally relative to the inserter tube 920, such that a distal portion of the inserter tube 920 is positioned over a proximal portion of the fingers 908. This causes the fingers 908 to close and contract on the fusion device 10 (as shown in FIG. 57B). To release the fusion device 10 from the fingers 908, the inserter fork 905 can slide in an opposite direction relative to the inserter tube 920.

Figure 59:
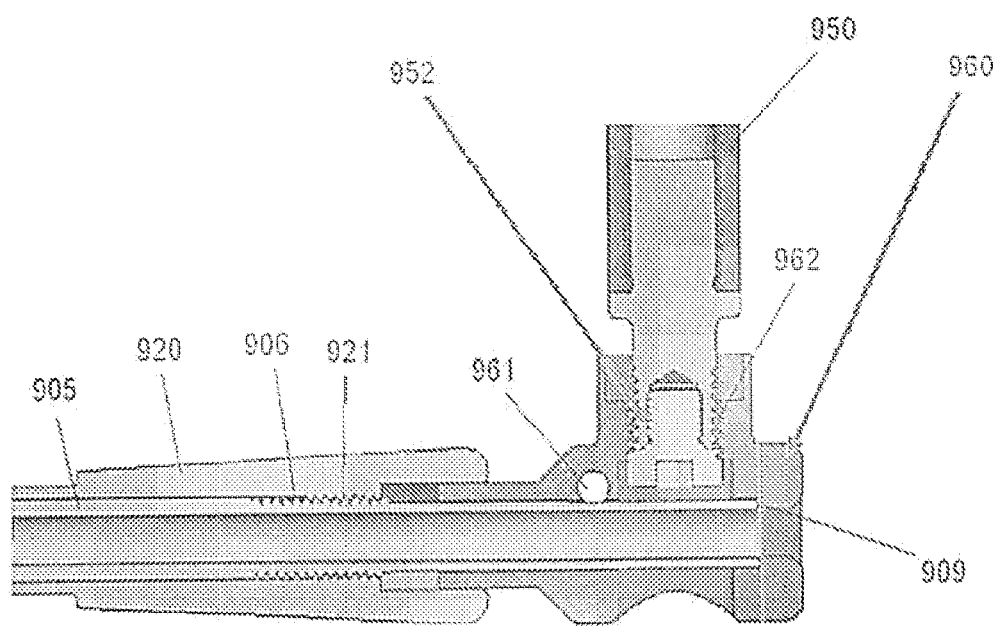
FIG. 59 is a side cross-sectional view of a proximal portion of an instrument including a handle.

In some embodiments, the relative movement between the inserter fork 905 and the inserter tube 920 is controlled by threads on both components. Inserter fork 905 can have threads 906 that engage corresponding threads 921 on the inserter tube 920 (as shown in FIG. 59). The inserter tube 920 can be threadingly rotated in a proximal or distal direction relative to the inserter fork 905, thereby causing opening and closing of the fingers 908 as desired.

Once the fingers 908 of the inserter fork 905 are secured to the fusion device (as shown in FIG. 57B), a driver, such as a hex driver, can be inserted through the lumen 930 that extends between the inserter fork 905 and the inserter tube 920. FIG. 57C illustrates a driver 945 inserted through the lumen 930. The driver 945 is configured to engage and actuate the actuation member 22. Rotation of the driver 945, and thus, the actuation member 22, in one direction causes the fusion device 10 to expand, while rotation in the opposite direction causes the fusion device 10 to contract. The instrument 900 thus advantageously provides a convenient means to both hold and secure the fusion device 10 (e.g., via the fingers 905) while simultaneously delivering a driver 945 therethrough to expand or contract the fusion device 10. In addition, by providing an inner lumen 930 for the driver 945, this provides a clean pathway for the driver 945 with little to no tissue interference.

Figures 58A, 58B:
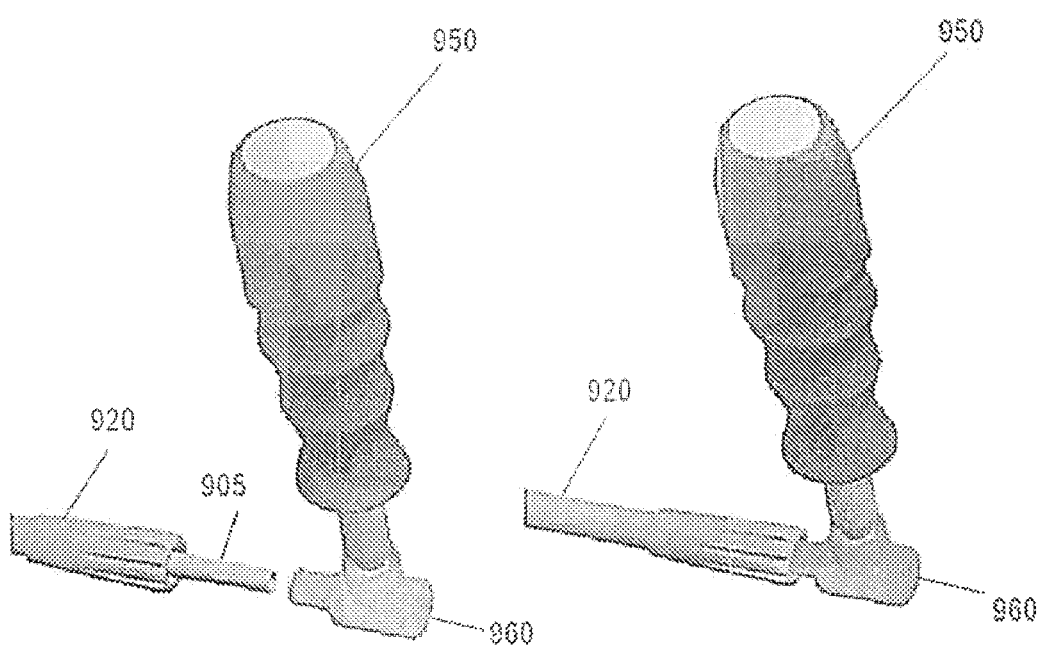
FIGS. 58A and 58B illustrate a proximal portion of an instrument including a handle for delivering and actuating a fusion device.

In addition to having a novel cooperating inserter fork 905 and inserter tube 920, the instrument 900 can also include a novel handle 950, as shown in FIGS. 58A and 58B. A surgeon can hold the handle 950 to advantageously stabilize and maintain control of the instrument in or outside of the body.

As shown in FIGS. 58A and 58B, the handle 950 can be accompanied by a coupler 960 which is configured to receive a portion of the inserter fork 905 therein. FIG. 58A illustrates the inserter fork 905 outside of the coupler 960, while FIG. 58B illustrates the inserter fork 905 received within the coupler 960. Once the inserter fork 905 is received in the coupler 960, a set screw within the handle (shown in FIG. 59 and discussed below) can be downwardly threaded to secure the handle 950 to the inserter fork 905. Thus, the inserter fork 905, inserter tube 920 and handle 950 can all be viewed as separate components that are capable of assembly or disassembly, thereby advantageously allowing easy cleaning of each of the components.

FIG. 59 is a side cross-sectional view of a proximal portion of an instrument including a handle 950, a coupler 960 and an inserter fork 905. From this view, one can see how the inserter fork 905 is received in the coupler 960. As shown in FIG. 59, in some embodiments, the inserter fork 905 can have one or more flats 909 (e.g., two, three, four or more) machined into its surface. The flats 909 are advantageously provided to direct the orientation of the coupler 960 (and thus the handle 950) relative to the fusion device 10. In some embodiments, the coupler 960 can be positioned over the flats 909 such that the handle 950 can be oriented in two directions—either parallel to the implant or perpendicular to the implant. In other embodiments, the inserter fork 905 is provided with even more flats 909 such that the handle 950 can be oriented in more than two directions. By providing the handle with the ability to have multiple orientations, this advantageously provides a surgeon with more options when using the instrument. In some embodiments, the coupler can include an orientation pin 961 that can glide over the flats 909 (and not on other surfaces), thereby helping to further orient the coupler and handle relative to the fusion device 10.

As shown in FIG. 59, a threaded set screw 952 is provided within the handle 950. The set screw 952 is configured to have outer threads that engage with complementary threads 962 of the coupler 962, thereby allowing upward and downward movement of the handle 950 relative to the coupler 962. As the handle 950 is moved downwardly, a distal portion of the set screw 952 contacts and engages a surface (e.g., the flats) of the inserter fork 905, thereby securing the handle 950 to the inserter fork 905.

Figure 60A:
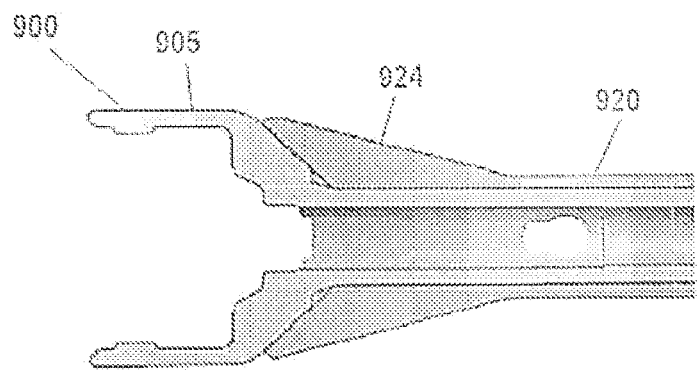
FIGS. 60A-60C illustrate an alternative embodiment of an inserter tube of an instrument.
Figure 60B:
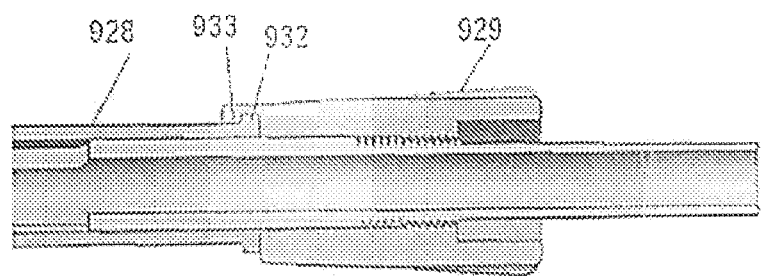
Figure 60C:
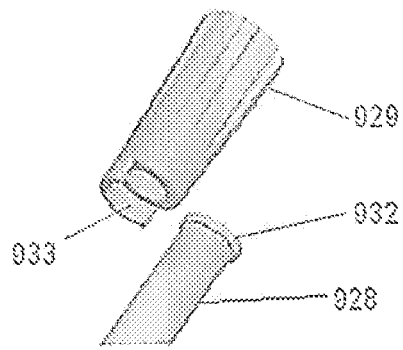

FIGS. 60A-60C illustrate an alternative embodiment of an inserter tube of an instrument according to some embodiments. As shown in FIG. 60A, the alternate inserter tube 920 includes a flared distal portion 924. The advantage of the flared distal portion 924 is that it provides for more surface engagement over the inserter fork 905, thereby preventing the inserting fork 905 from accidental splaying and disengagement from the fusion device 10.

FIGS. 60B and 60C illustrate a proximal portion of the alternate inserter tube 920. From these views, one can see that the alternate inserter tube 920 can be formed of a first sleeve portion 928 and a second sleeve portion 929 that is mateable to the first sleeve portion 928. The first sleeve portion 928 can have a first mateable portion 932 and the second sleeve portion 929 can have a second mateable portion 933 that is coupled to the first mateable portion 932. As shown in FIG. 60C, the first mateable portion 932 and the second mateable portion 933 can comprise complementary flanges or lips.

As shown in FIG. 60B, the second sleeve portion 929 of the alternate inserter tube 920 can have inner threads that mate with threads on the inserter fork. When the first sleeve portion 928 and second sleeve portion 929 are mated on the inserter fork, rotation of the second sleeve portion 929 (e.g., via its threads) relative to the inserter fork can help translate the first sleeve portion 928 back and forth along the length of the inserter fork. Accordingly, the entire body of the alternate inserter tube 920, including the flared distal portion 924, can be translated along the length of the inserter fork.

Figure 61:
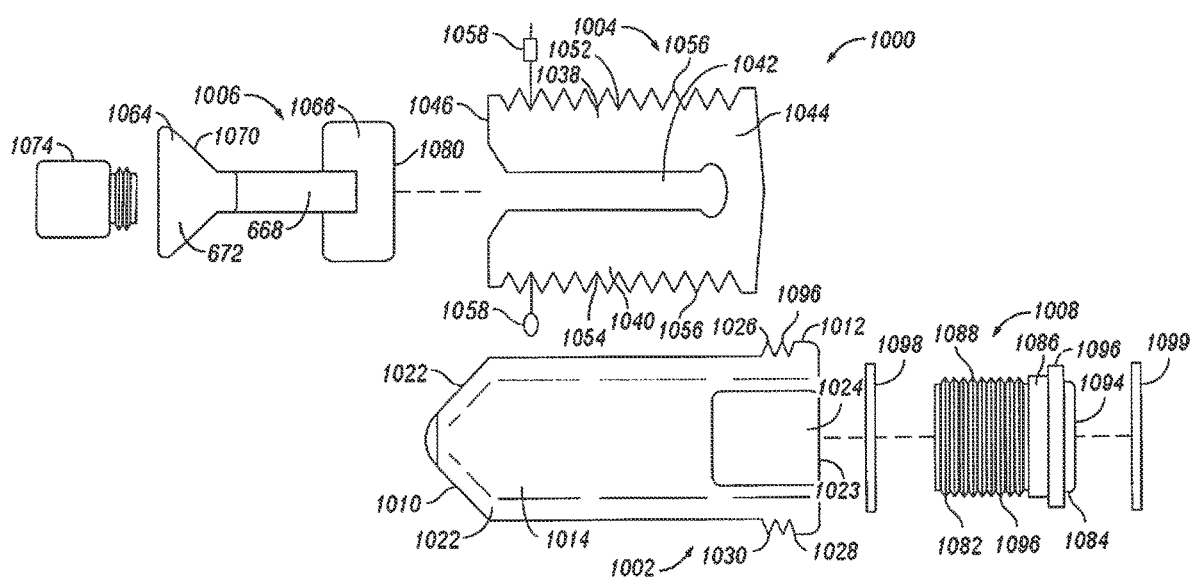
FIG. 61 is an exploded view of another embodiment of an expandable fusion device according to the present invention.
Figure 62:
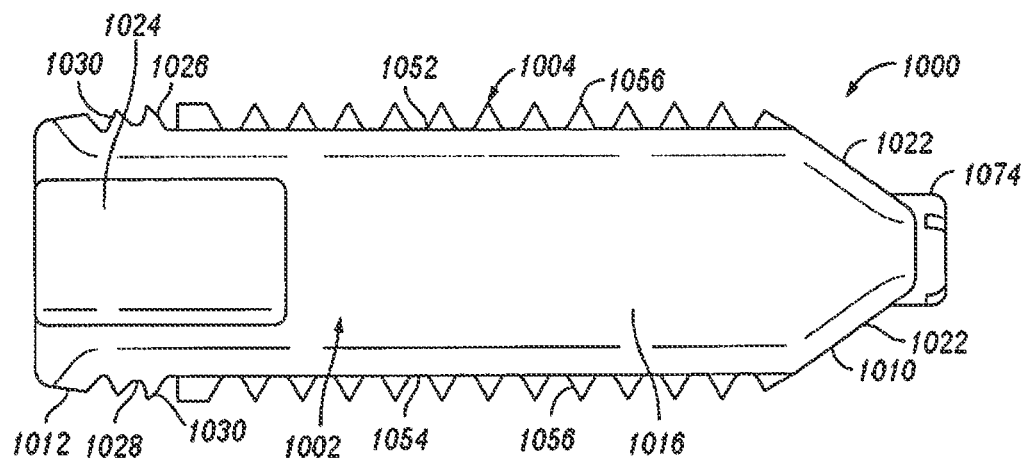
FIG. 62 is a side view of the expandable fusion device of FIG. 61 in an unexpanded configuration.
Figure 63:
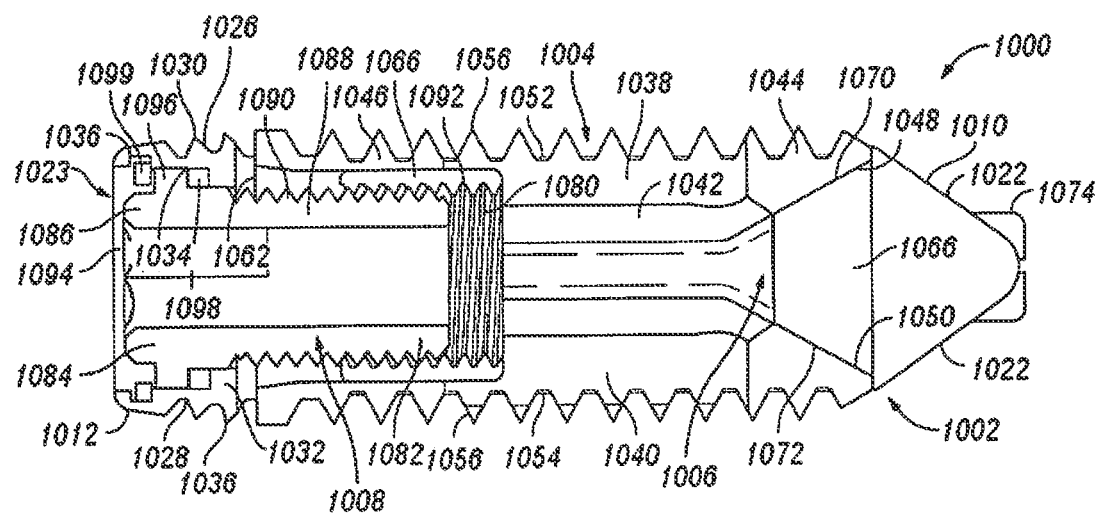
FIG. 63 is a cross-sectional side view of the expandable fusion device of FIG. 61 in an unexpanded configuration.
Figure 64:
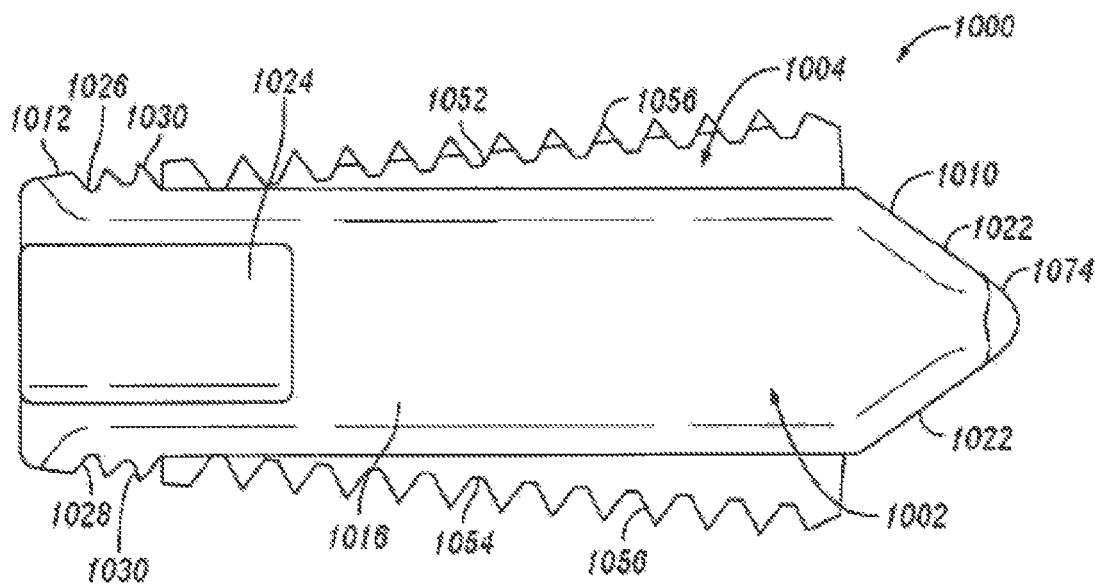
FIG. 64 is a side view of the expandable fusion device of FIG. 61 in an expanded configuration.
Figure 65:
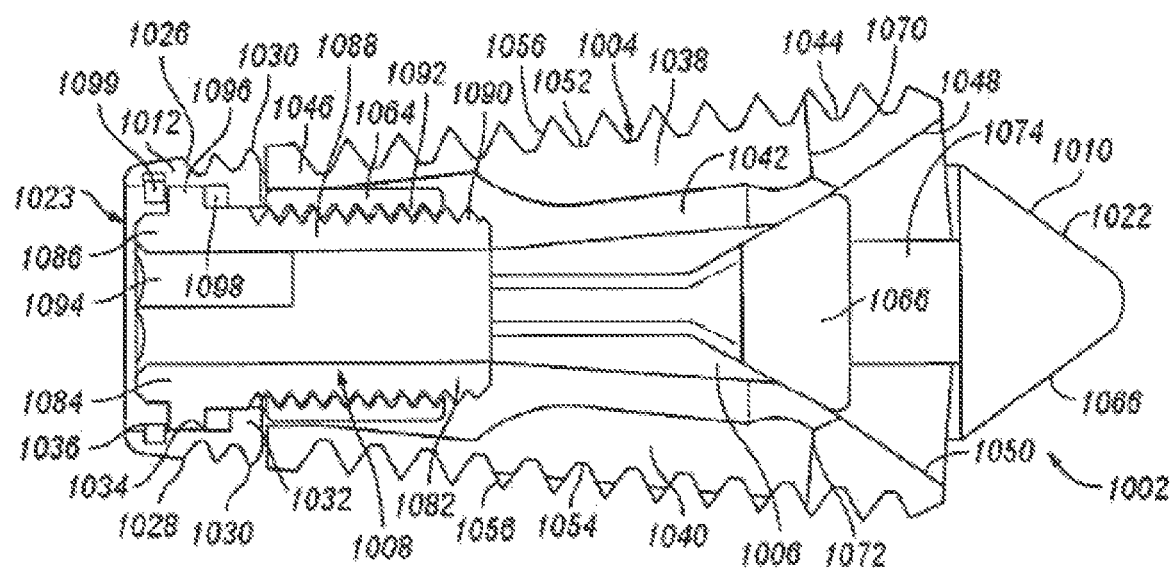
FIG. 65 is a cross-sectional side view of the expandable fusion device of FIG. 61 in an expanded configuration.

With reference now to FIGS. 61-66, the expandable member 1004 will now be described in more detail in accordance with example embodiments. It is contemplated that the expandable member 1004 can be made from a flexible material, such as PEEK, or any other biocompatible material such as stainless steel or titanium. However, other materials may also be used for the expandable member 1004 in accordance with embodiments of the present invention. As illustrated, the expandable member 1004 may include two or more arms, such as first arm 1038 and second arm 1040, separated by a channel 1042. The expandable member 1004 may further include a fixed end 1044 and an expandable end 1046 with the channel 1042 running between the first and second arms 1038, 1040 from the fixed end 1044 to the expandable end 1046. The first arm 1038 and the second arm 1040 may be connected at the fixed end 1044 which links the first and second arms 1038, 1040. The first and second arms 1038, 1040 may move substantially independent from one another at the expandable end 1046 while remaining connected at the fixed end 1044. As illustrated, the first and second arms 1038, 1040 may be separated by the channel 1042. In the illustrated embodiment, the channel 1042 ends at the fixed end 1044 in a slightly larger diameter which acts a hinge during expansion of the fusion device 1000. Markers 1058 (FIG. 61) may be seated in recesses (such as blind holes 1060 shown on FIG. 66) formed in each of the first and second arms 1038, 1040 to, for example, to assist in imaging of the device, such as fluoroscopy. In addition, the expandable member 1004 may also include a posterior opening 1062 in the fixed end 1044, such as a cylindrical bore, through which the actuation member 1008 can extend, as best seen in FIGS. 63 and 65.

Figure 66:
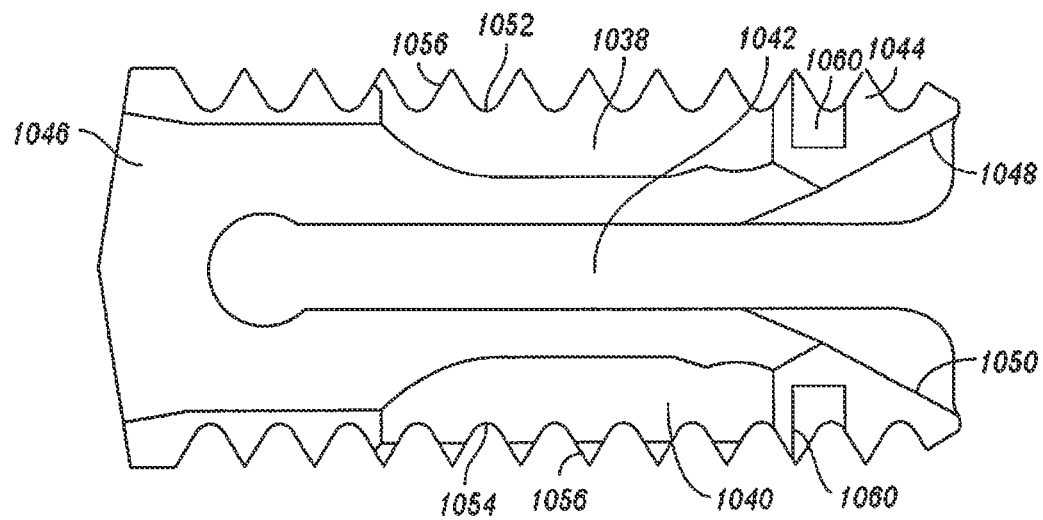
FIG. 66 is a cross-sectional side view of the expandable member of the expandable fusion device of FIG. 61.

As best seen in FIGS. 63, 65, and 66, the first and second arms 1038, 1040 of the expandable member 1004 each include ramped surfaces 1048, 1050, respectively. In the illustrated embodiment, the ramped surfaces 1048, 1050 are at or near the expandable end 1046. In the illustrated embodiment, the first and second arms 1038 each include one ramped surface (e.g., ramped surface 1048 and ramped surface 1050), but can include any number of ramped surfaces.

In the illustrated embodiment, the first and second arms 1038, 1040 each include bone engagement surfaces 1052, 1054, respectively, that face outward. As illustrated, the bone engagement surfaces 1052, 1054 may be flat and generally planar to allow for engagement of the first and second arms 1038 with the adjacent vertebral bodies 2, 3 (e.g., shown on FIG. 1). Alternatively (not illustrated), the bone engagement surfaces 1052, 1054 may be curved convexly or concavely to allow for a greater or less degree of engagement with the adjacent vertebral bodies 2, 3. It also contemplated that the bone engagement surfaces 1052, 1054 may be generally planar, but include a generally straight ramped or a curved ramped surface. The ramped surface may allow for an even greater degree of angled expansion. In some embodiments, the bone engagement surfaces 1052, 1054 may include texturing 1056 to aid in gripping the adjacent vertebral bodies 2, 3. Although not limited to the following, the texturing can include teeth, ridges, friction increasing elements, keels, or gripping or purchasing projections.

Figure 67:
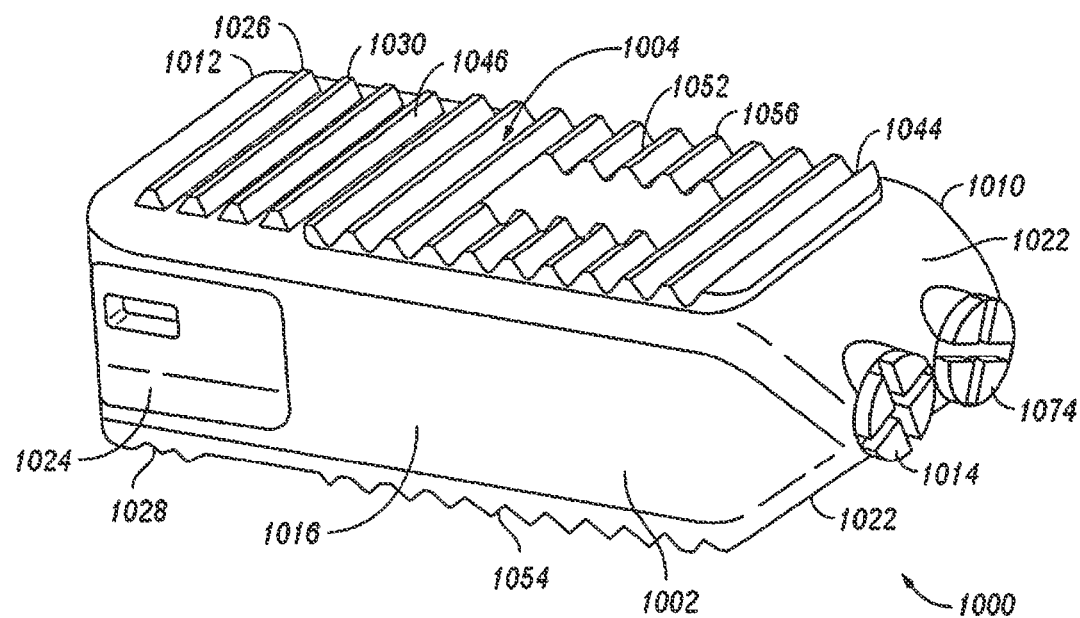
FIG. 67 is a front perspective of the expandable fusion device of FIG. 61.
Figure 68:
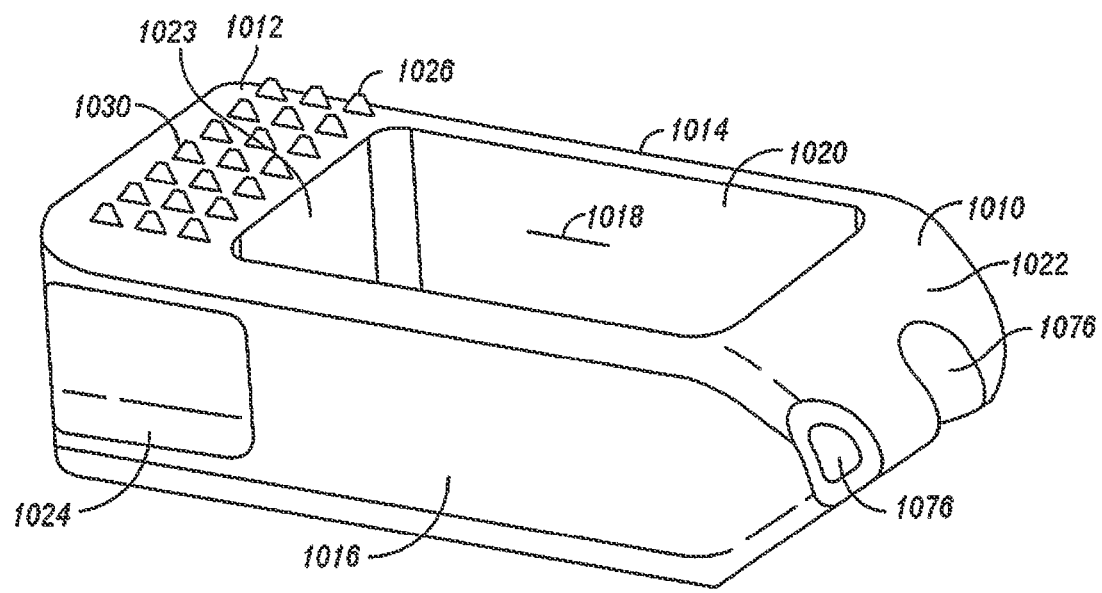
FIG. 68 is a front perspective of the body portion of the expandable fusion device of FIG. 61.

With reference now to FIGS. 61, 63, and 65, the ramped translation member 1006 will now be described in more detail in accordance with example embodiments. As illustrated, the ramped translation member 1006 includes a first expansion portion 1064 and a second expansion portion 1066, the first and second expansion portions 1064, 1066 being connected by one or more bridge portions 1068. It is also contemplated that there may be more than two expansion portions. The first expansion portion 1064 may have ramped surfaces 1070, 1072, which may be dimensioned and configured to engage the ramped surfaces 1048, 1050 in the expandable end 1046 of the expansion member 1004. In the illustrated embodiment, the first expansion portion 1064 includes two ramped surfaces 1070, 1072. In the illustrated embodiment, the ramped surfaces 1070, 1072 of the first expansion portion 1064 are rear facing. With additional reference to FIGS. 62 and 67, an embodiment further includes one or more screws 1074 that are received in the first expansion portion 1064 with the screws 1074 being threaded through openings 1076 in the posterior end 1012 of the body portion 1002 to stabilize the ramped translation member 1006 in the internal cavity 1018 of the body portion 1002. The ramped translation member 1006, in an exemplary embodiment, may further include an opening 1080, such as a cylindrical bore, sized to receive the actuation member 1008. In the illustrated embodiment, the opening 1080 is disposed in the second expansion portion 1066.

With reference to FIGS. 61, 63, and 65, the actuation member 1008 will now be described in more detail in accordance with example embodiments. In an exemplary embodiment, the actuation member 1008 has a first end 1082 and a second end 1084. As illustrated, the actuation member 1008 may include a head portion 1086 at the second end 1084 and a extension portion 1088 extending from the head portion. Threading 1090 disposed on the extension portion 1088 should threadingly engage corresponding threading 1092 along a portion of the opening 1080 of the ramped translation member 1006. In another embodiment (not shown), the actuation member 1008 may include ratchet teeth instead of the threading 1090 with the ratchet teach engaging corresponding ratchet teeth in the opening 1080 of the ramped translation member 1006. The second end 1084 includes a recess 1094 dimensioned to receive an instrument (not shown) that is capable of rotating or otherwise moving the actuation member 1008.

As illustrated, the head portion 1086 of the actuation member 1008 may further include a flange 1096 or other suitable projection. In some embodiments, the flange 1096 of the actuation member 608 may engage the mechanical stop 1032 projecting from the interior surface 1034 of the opening 1023 in the body portion 1002. Engagement of the flange 1096 with the mechanical stop 1032 may restrict forward movement of the actuation member 1008 into the opening 1023 in the body portion 1002. As illustrated, a ring 1098 (e.g., a PEEK ring) may be disposed between the mechanical stop 1032 and the flange 1096 to reduce friction between the actuation member 1008 and the body portion 1002, for example, when the fusion device 1000 is actuated, such as by rotation of the actuation member 1008, for example. As further illustrated, a retaining ring 1099 may be used to engage the head portion 1086 and hold the actuation member 1008 in the opening 1023 in the body portion 1002, for example, preventing threading out of the actuation member 608 when rotated. The retaining ring 1099 may be disposed in the internal groove 1036 in the opening 1023 of the body portion 1002, for example. In one embodiment, the retaining ring 1099 may be a snap ring.

Turning now to FIGS. 61, 62-65 and 67, an example method of installing the expandable fusion device 1000 is now discussed. Prior to insertion of the fusion device 1000, the intervertebral space is prepared. In one method of installation, a diskectomy is performed where the intervertebral disc, in its entirety, is removed. Alternatively, only a portion of the intervertebral disc can be removed. The endplates of the adjacent vertebral bodies 2, 3 (shown on FIG. 1, for example) are then scraped to create an exposed end surface for facilitating bone growth across the intervertebral space. The expandable fusion device 1000 is then introduced into the intervertebral space, with the anterior end 1010 of the body portion 1002 being inserted first into the disc space followed by the posterior end 1012. In an exemplary method, the fusion device 600 is in the unexpanded position when introduced into the intervertebral space. The wedged-shaped of the anterior end 1010 in the illustrated embodiment should assist in distracting the adjacent vertebral bodies 2, 3, if necessary. This allows for the option of having little to no distraction of the intervertebral space prior to the insertion of the fusion device 1000. In another exemplary method, the intervertebral space may be distracted prior to insertion of the fusion device 1000. The distraction provide some benefits by providing greater access to the surgical site making removal of the intervertebral disc easier and making scraping of the endplates of the vertebral bodies 2, 3 easier.

With the fusion device 1000 inserted into and seated in the appropriate position in the intervertebral disc space, the fusion device 1000 can then be expanded into the expanded position, as best seen in FIGS. 62-65. FIGS. 62 and 63 show the fusion device 1000 prior to expansion while FIGS. 64 and 65 show the fusion device 1000 in the expanded position. To expand the fusion device 1000, an instrument is engaged with the recess 1094 in the second end 1084 of the actuation member 1008. The instrument is used to rotate actuation member 1008. As discussed above, actuation member 1008 can be engaged (e.g., threadingly engaged) with the ramped translation member 1006; thus, as the actuation member 1008 is rotated in a first direction, the ramped translation member 1006 moves with respect to the body portion 1002 toward the posterior end 1012 of the body portion 1002. In another exemplary embodiment, the ramped translation member 1006 is moved in a linear direction with the ratchet teeth engaging as means for controlling the movement of the ramped translation member 1006. As the ramped translation member 1006 moves, the ramped surfaces 1070, 1072 of the first expansion portion 1064 push against the ramped surfaces 1048, 1050 in the expandable end 1046 of the expandable member 1004 pushing the first and second arms 1038, 1040 outwardly into the expanded position. This can best be seen in FIGS. 64 and 65. Since the expansion of the fusion device 1000 is actuated by a rotational input, the expansion of the fusion device 1000 is infinite. In other words, the first and second arms 1038, 1040 can be expanded to an infinite number of heights dependent on the rotational advancement of the actuation member 1008.

In the event the fusion device 1000 needs to be repositioned or revised after being installed and expanded, the fusion device 1000 can be contracted back to the unexpanded configuration, repositioned, and expanded again once the desired positioning is achieved. To contract the fusion device 1000, the instrument is engaged with the recess 1094 in the second end 1084 of the actuation member 1008. The instrument is used to rotate actuation member 1008. As discussed above, actuation member 1008 can be threadingly engaging the ramped translation member 1006; thus, as the actuation member 1008 is rotated in a second direction, opposite the first direction, the ramped translation member 1006 moves with respect to the body portion 1002 toward the anterior end 1010 of the body portion 1002. As the ramped translation member 1006 moves, the first and second arms 1038, 1040 should contract inwardly back into their unexpanded position, for example.

With continued reference to FIGS. 61, 62-65 and 67, an example method of assembly the expandable fusion device 1000 is now discussed. In accordance with present embodiments, the ramped translation member 1006 may be inserted into the expandable member 1004. By way of example, the second expansion portion 1066 may be inserted into the channel 1042 of the expandable member 1004 at the expandable end 646 and advanced to the fixed end 1044. After insertion of the ramped translation member 1006, the expandable member 1004 may then be placed into the internal cavity 1018 in the body portion 1002. For example, the expandable member 1004 may be inserted through window (e.g., upper window 1020) into the internal cavity 1018. As illustrated, the fixed end 1044 of the expandable member 1004 should be positioned near the posterior end 1012 of the body portion 1002. The one or more screws 1074 may then be inserted through the body portion 1002 and into the ramped translation member 1006 to, for example, stabilize the ramped translation member 1006 preventing rotation. The actuation member 1008 may also be inserted into the opening 1023 in the posterior end 1012 of the body portion and advanced until it is in engagement with the ramped translation member 1006. In one embodiment, the actuation member 1008 may be advanced into threaded engagement with the opening 1080 in the ramped translation member.

In an embodiment, the expandable fusion device 1000 can be configured and sized to be placed into an intervertebral disc space between the adjacent vertebral bodies 2 and 3 (shown on FIG. 1, for example) and expanded. In some embodiments, the expandable fusion device 1000 may have a width in a range of from about 8 mm to about 22 mm and a length in a range of from about 15 mm to about 65 mm. In further embodiments, the expandable fusion device 1000 may have a width in a range of from about 8 mm to about 12 mm and a length in a range of from about 20 mm to about 30 mm. In some embodiments, the expandable fusion device 10 may have an initial height in an unexpanded position in a range of from about 7 mm to about 20 mm and, alternatively from about 7 mm to about 15 mm. In some embodiments, the maximum expansion of the first and second arms 1038, 1040 at the anterior end 1010 of the body portion 1002 is about 4 mm or potentially even more.

Figure 69:
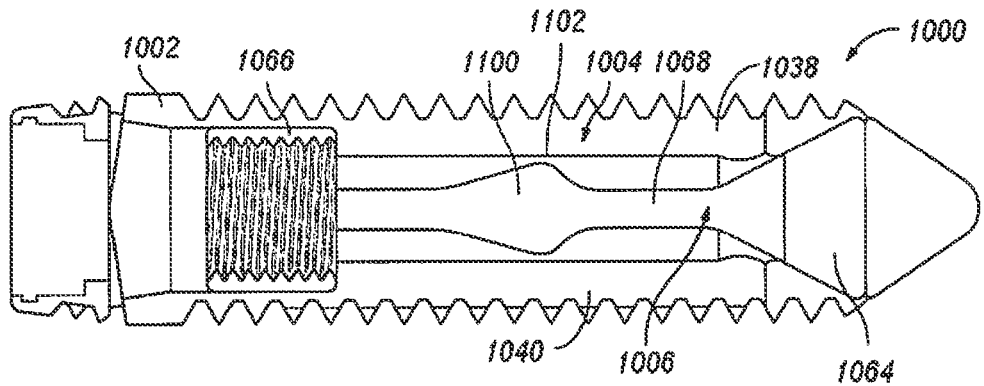
FIG. 69 is a cross-sectional side view of an alternative embodiment of the expandable fusion device of FIG. 61 in an unexpanded configuration.
Figure 70:
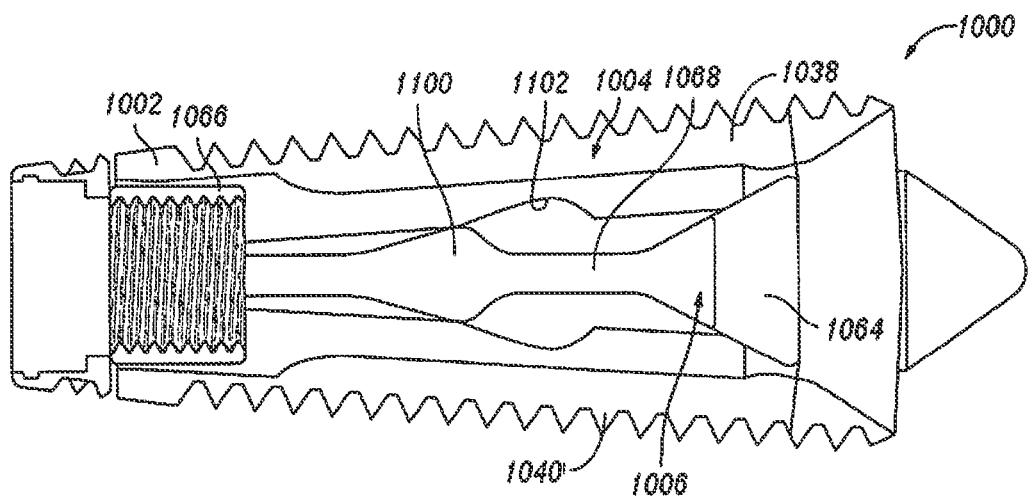
FIG. 70 is a cross-sectional side view of the alternative embodiment of the expandable fusion device shown on FIG. 69.

FIGS. 69 and 70 illustrate an alternative embodiment of the expandable fusion device 1000 according to the present invention. For longer configurations of the expandable fusion device 1000, the first and second arms 1038, 1040 may sag or flex, for example, when engaging the adjacent vertebral bodies 2, 3 (shown on FIG. 1, for example). Accordingly, embodiments shown on FIGS. 69 and 70 further include one or more protruding support members 1100 on the ramped translation member 1006. As illustrated, the protruding support members 1100 may be disposed on the one or more of the bridge portions 1068 between the first and second expansion portions 1064, 1066. The protruding support members 1100 may engage corresponding recesses 1102 in the first and second arms 1038, 1040. The protruding support members 1100 may act to support the first and second arms 1038, 1040 and prevent undesired flexing during expansion. In alternative embodiments (not shown), the actuation member 1008 may engage the expandable member 1004 (for example, with a slot and a groove) so that, as the first and second arms 1038, 1040 expands, the actuation member 1008 may engage the expandable member 1004 to cause convexity.

Figure 71:
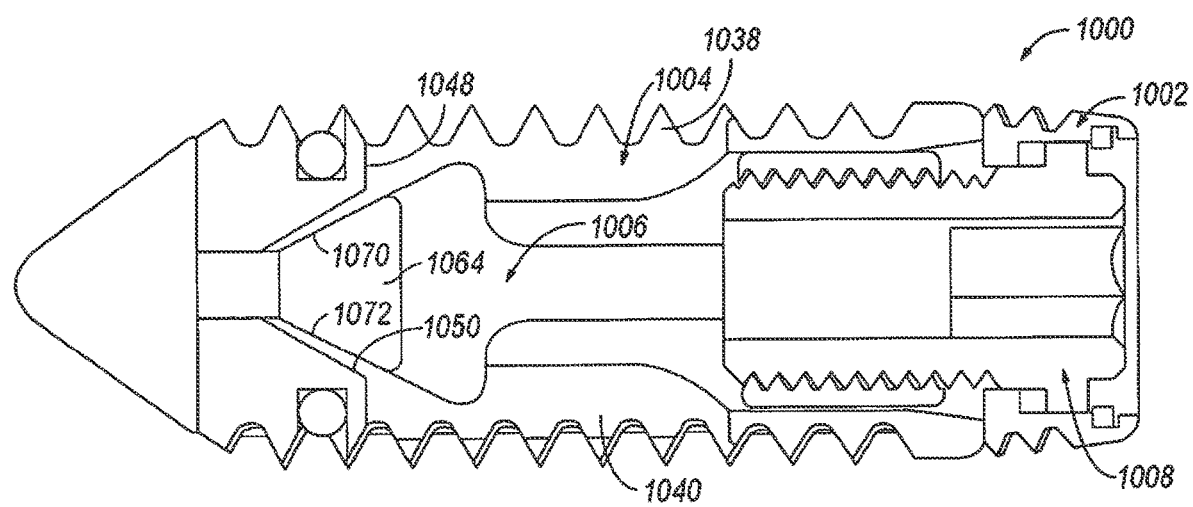
FIG. 71 is a cross-sectional side view of an alternative embodiment of the expandable fusion device of FIG. 61 in an unexpanded configuration.

FIG. 71 illustrates an alternative embodiment of the expandable fusion device 1000 according to the present invention. The embodiments illustrated on FIGS. 61, 62-65 and 67 illustrate the ramped surfaces 1070, 1072 on the first expansion portion 664 of the ramped translation member 1006 being rear facing. In the embodiment illustrated on FIG. 71, the ramps have been reversed with the ramped surfaces 1070, 1072 on the first expansion portion 1064 being forward facing. Accordingly, the corresponding ramped surfaces 1048, 1050 on the first and second arms 1038, 1040 of the expandable member 1004 have also been reversed and are shown on FIG. 71 as being rear facing. Accordingly, rotation of the actuation member 1008 should move the ramped translation member 1006 forward to the anterior end 1010 of the body portion 1002 such that the ramped surfaces 1070, 1072 of the ramped translation member 1006 push against the ramped surfaces 1048, 1050 of the first and second arms 1038, 1040 pushing the first and second arms 1038, 1040 outwardly into the expanded position.

Figure 72:
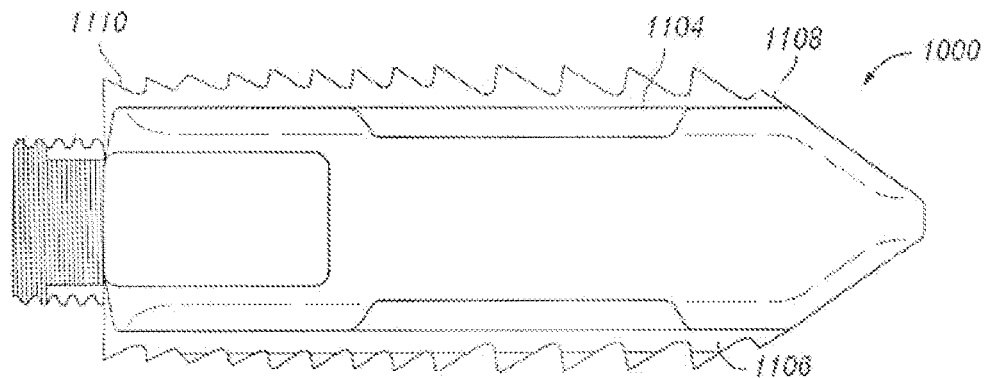
FIGS. 72-83 are side views of an expandable fusion device showing different modes of lordotic expansion.
Figure 73:
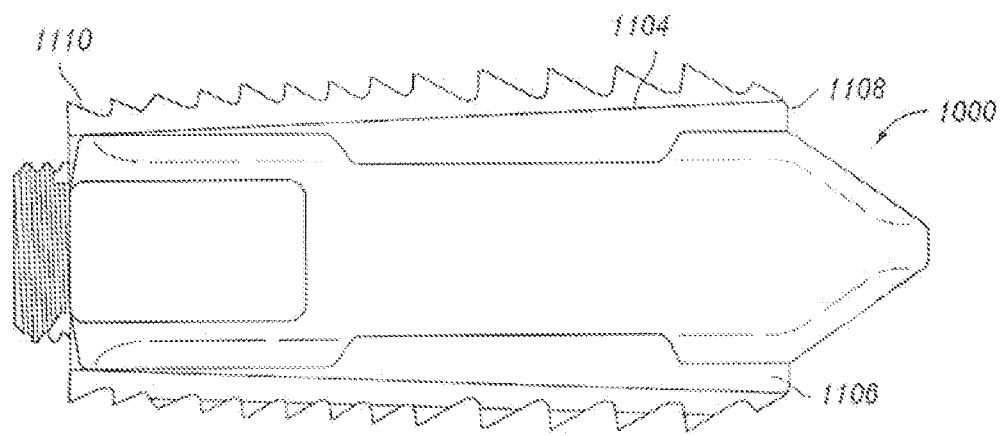
Figure 74:
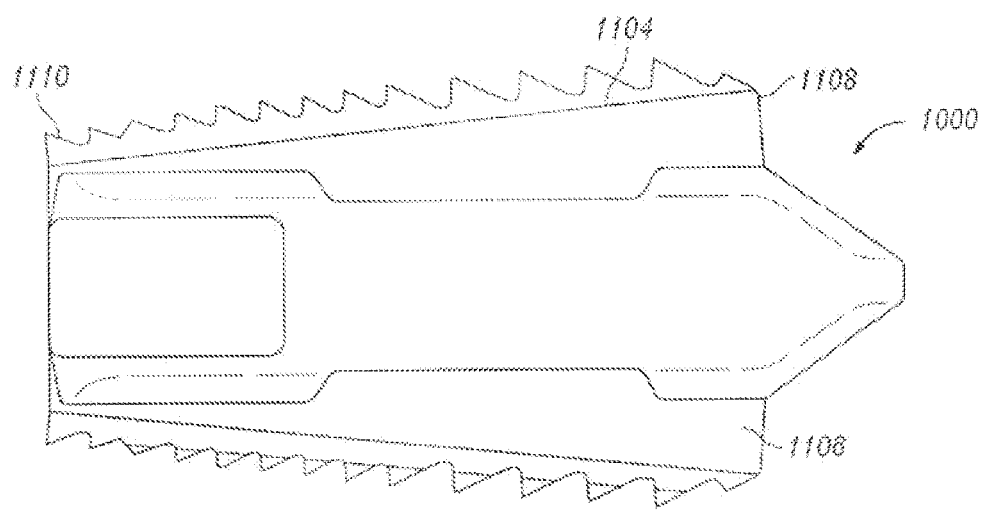
Figure 75:
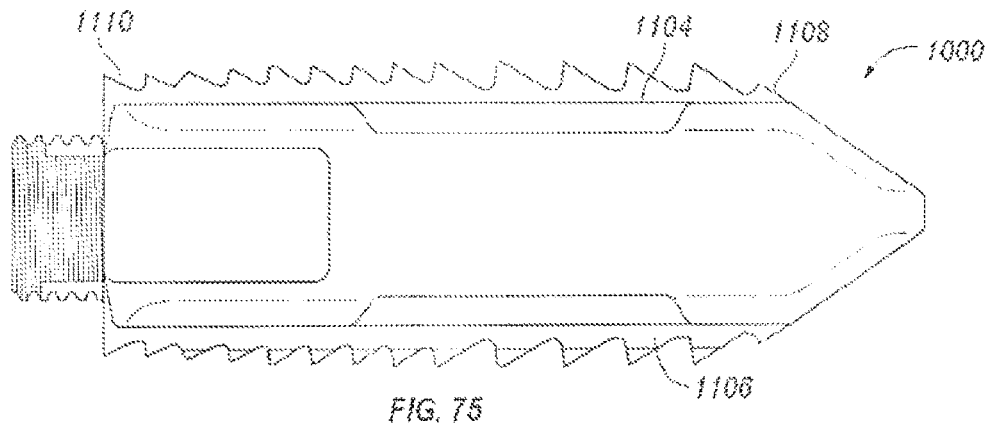
Figure 76:
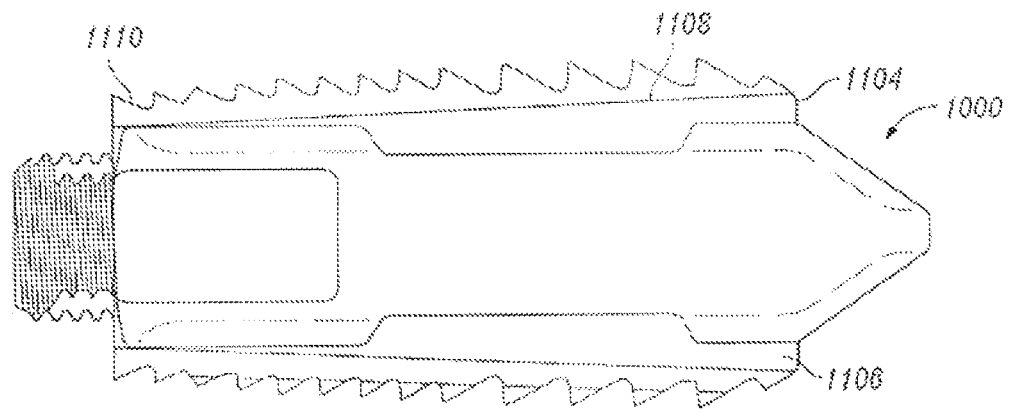
Figure 77:
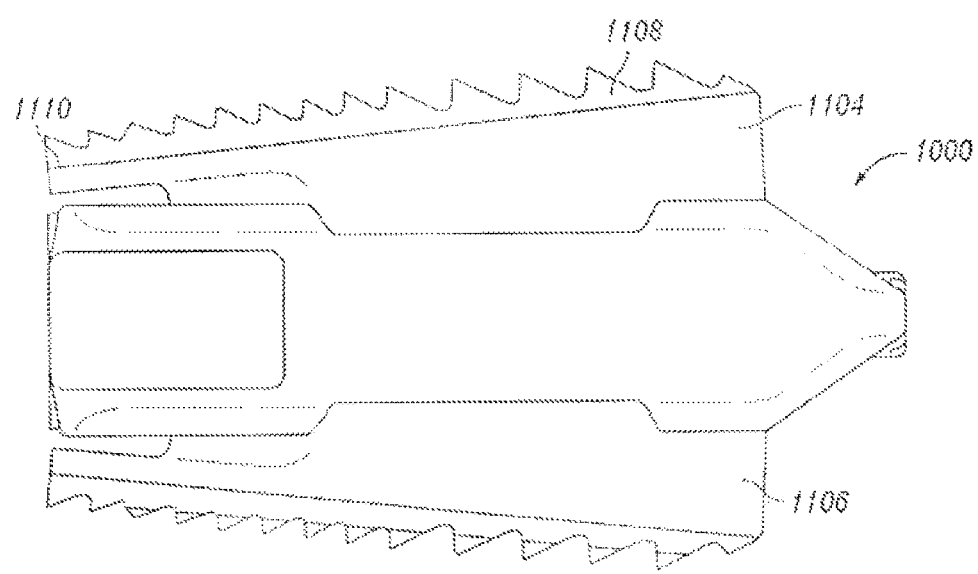
Figure 78:
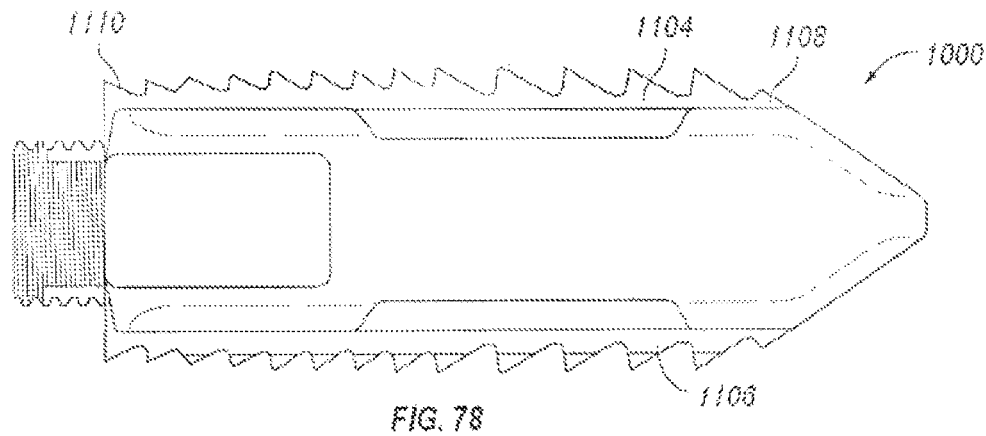
Figure 79:
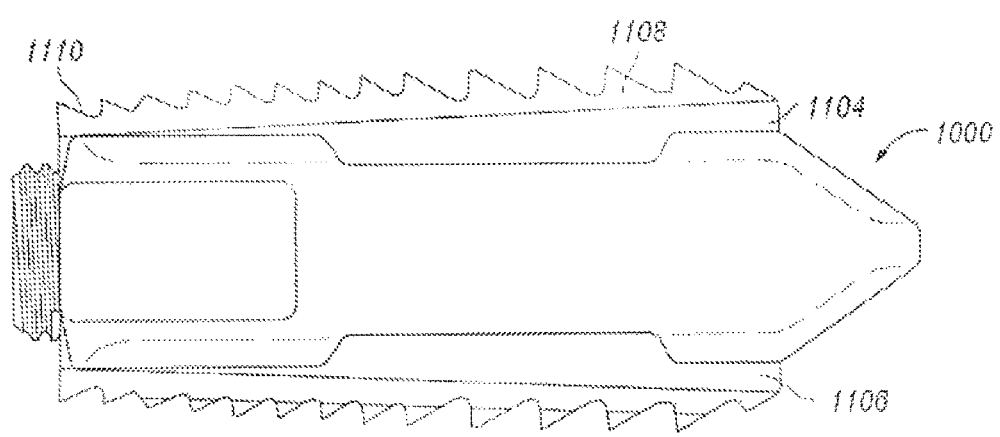
Figure 80:
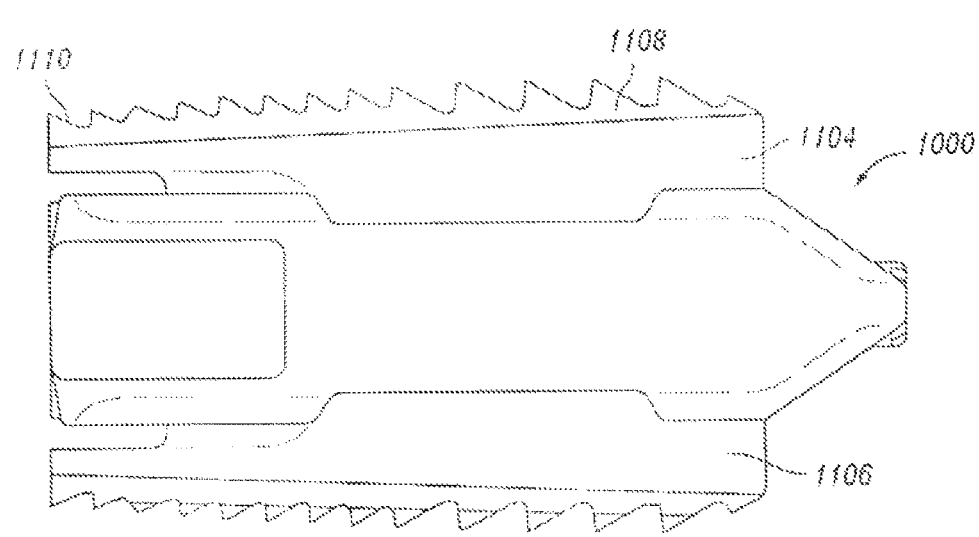
Figure 81:
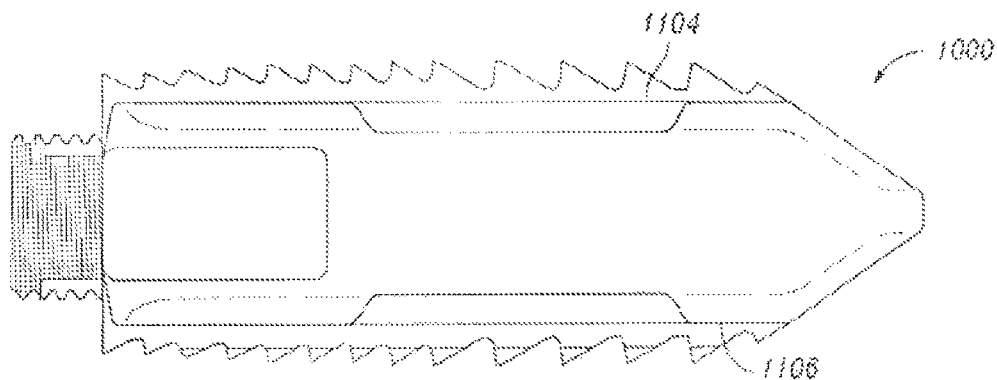
Figure 82:
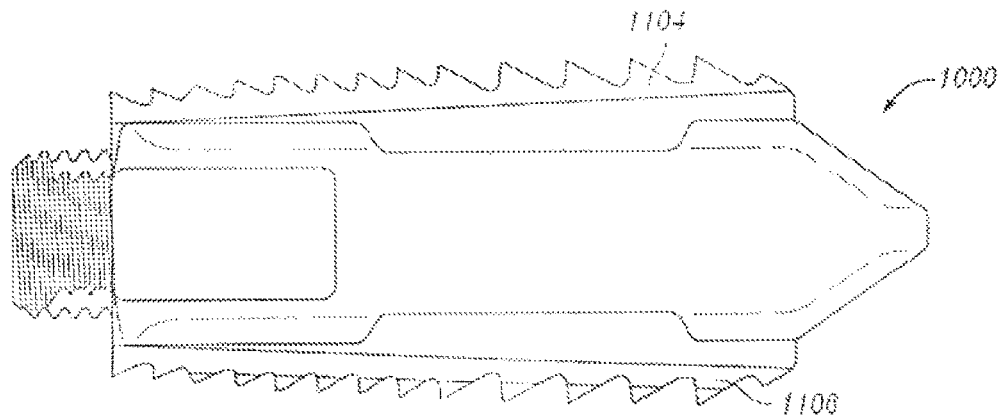
Figure 83:
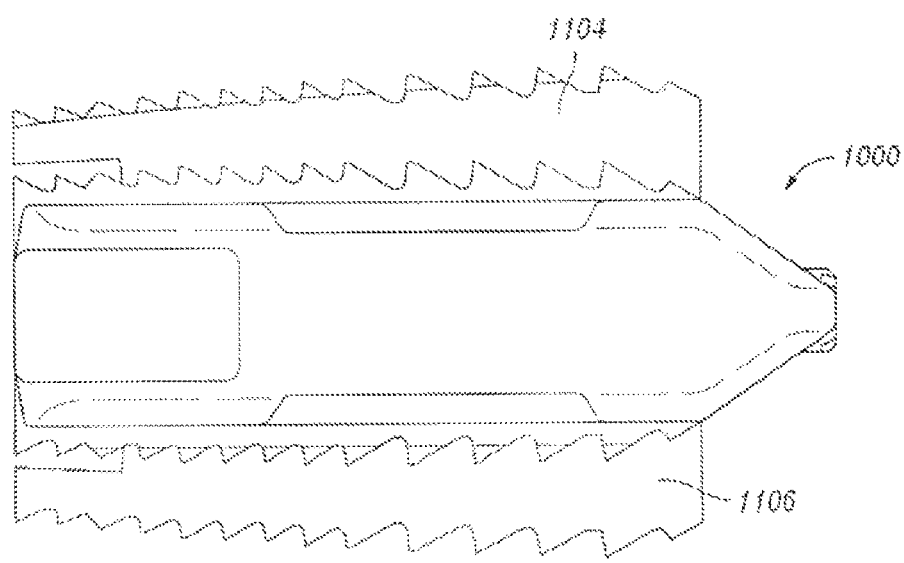

As previously mentioned, embodiments of the expandable fusion devices, such as expandable fusion device 1000 shown on FIGS. 61, 62-65 and 67 in which the endplates (e.g., endplates 14, 16 or first and second arms 1038, 1040) may expand into an angled configuration. As illustrated by FIGS. 72-83, the endplates 1104, 1106 of an expandable fusion device 1000 may be expanded in a number of different ways. For example, FIGS. 72-74 illustrate an expandable fusion device 1000 in which the endplates 1104, 1106 only expand at the anterior side 1108 while remaining fixed at the posterior side 1110. FIGS. 75-77 illustrate an additional example of an expandable fusion device 1000 in which the endplates 1104, 1106 expand at both the anterior side 1108 and the posterior side 1110 but at different rates. FIGS. 78-80 illustrate yet another example of an expandable fusion device 1000 in which the endplates 1104, 1106 first expand at only the anterior side 1108 to achieve lordotic angle followed by expansion at both the anterior side 1108 and the posterior side 1110 at constant rates to achieve height increase. Advantageously, the embodiment shown on FIGS. 78-80 allows for full angulation without the corresponding height increase. FIGS. 81-83 illustrate yet another example of an expandable fusion device 1000. As illustrated, the expandable fusion device 1000 has two separate degrees of freedom, allowing for independent angulation and expansion of the endplates 1104, 1106.

Although the preceding discussion only discussed having a single fusion device (e.g., fusion device 10, fusion device 210, or fusion device 1000) in the intervertebral space, it is contemplated that more than one fusion device can be inserted in the intervertebral space. It is further contemplated that each fusion device does not have to be finally installed in the fully expanded state. Rather, depending on the location of the fusion device in the intervertebral disc space, the height of the fusion device may vary from unexpanded to fully expanded.

One skilled in the art will appreciate that the instrument described herein is not limited to the expandable fusion device 10 described above, but can be applied to assist in the delivery and/or actuation of other implants as well. For example, in some embodiments, the instrument described can be used to deliver a non-expandable device having side recesses. In addition, the instrument can be used to deliver different types of expandable devices, including expandable TLIFs and other types of spinal implants.

Additional embodiments of expandable fusion devices are shown in FIGS. 84A-86B. In these embodiments, the fusion device 1210 includes an actuation member 1220 that is operatively attached to a translation member 1218. Rotation of the actuation member 1220 causes linear translation of the translation member 1218, thereby causing expansion of the fusion device 1210. Advantageously, in these embodiments, the actuation member 1220 is fixed at an anterior portion of the fusion device 1210, thereby leaving a posterior opening 1222 available for which material (e.g., bone graft material) can be easily inserted therethrough. The ability to insert and pack bone graft material through the posterior opening 1222 is highly beneficial, as such material can be packed even when the expandable fusion device has already been expanded, thereby maximizing the amount of bone graft material in the device 1210.

Figure 84A:
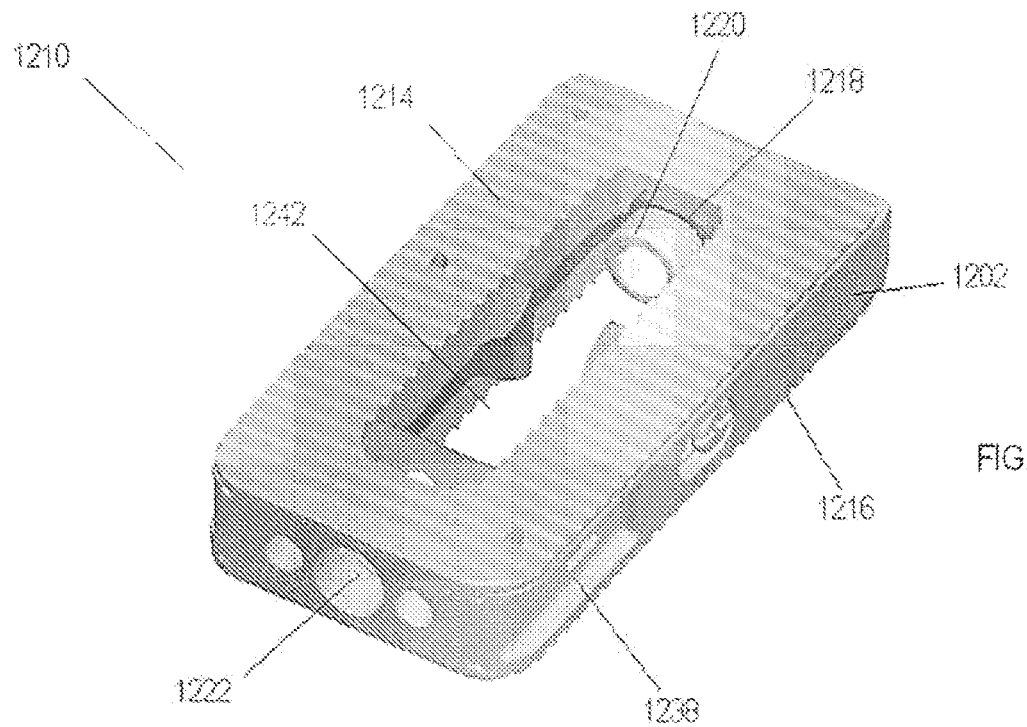
FIGS. 84A and 84B are top perspective views of an alternative expandable fusion device having an anterior-based actuation member.
Figure 84B:
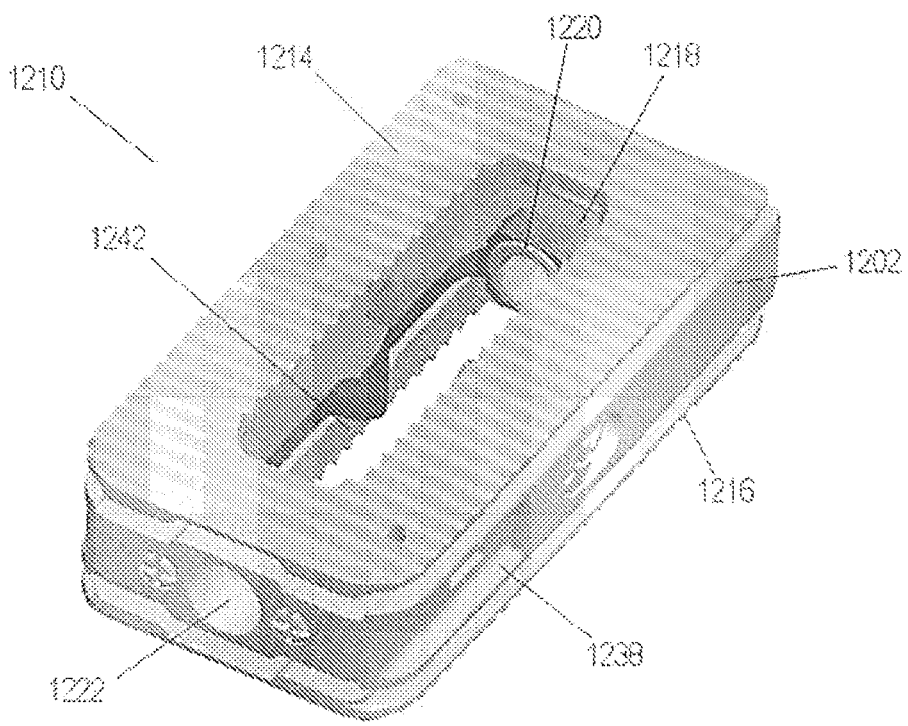

As shown in FIGS. 84A and 84B, the expandable fusion device 1210 comprises an upper endplate 1214, a lower endplate 1216, sidewalls including one or more inserter instrument recesses 1238, a body portion 1202, a threaded actuation member 1220 and a translation member 1218 having angled surfaces or ramps. The upper endplate 1214 and lower endplate 1216 can include texturing, such as teeth or ridges, to assist in gripping of adjacent vertebral bodies. On the inner sides of the upper endplate 1214 and the lower endplate 1216 are inner angled surfaces or ramps (similar to prior embodiments) that are configured to interact with ramps on the translation member 1218 to cause expansion or contraction of the device. The sidewalls include one or more inserter instrument recesses 1238 that serve as gripping surfaces to deliver the device 1210.

The translation member 1218 can include one or more angled surfaces or ramps 1251, 1252, 1254. The ramps can be separated by bridge members 1256. As in prior embodiments, the ramps 1251, 1252, 1254 are configured to engage and interact with ramps on the upper and lower endplates 1214, 1216, thereby causing expansion or contraction of the fusion device 1210. The translation member 1218 can include upwardly facing ramps that interact with downwardly facing ramps from the upper endplate 1214, and downwardly facing ramps that interact with upwardly facing ramps from the lower endplate 1216. Thus, while only the upwardly facing ramps 1251, 1252 and 1254 are visible from the top views in FIGS. 85A and 85B, one skilled in the art will appreciate that downwardly facing ramps can also be provided. In addition, while the translation member 1218 is illustrated as having three ramps along a length of the translation member, in other embodiments, the translation member 1218 can have one, two, four, five or more ramps separated by bridges.

Figure 85A:
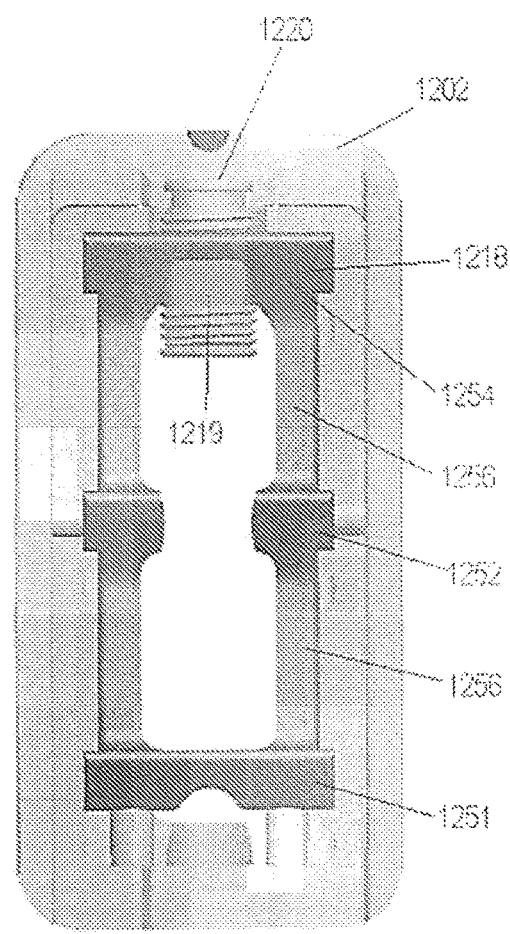
FIGS. 85A and 85B are top views of the alternative expandable fusion device of FIG. 84A with endplates removed.

In addition to the ramps, the translation member 1218 includes an engaging portion 1219 that engages the actuation member 1220 (as shown in FIG. 85A). The engaging portion 1219 is configured to include inner threads that engage with threads of the actuation member 1220. Rotation of the actuation member 1220 causes the translation member 1218 to move linearly along the threads of the actuation member 1220.

In the present embodiments, the actuation member 1220 is threaded through the translation member 1218 near the anterior or front side of the body portion 1202, which can be tapered (e.g., to assist in distraction of bone members). With the actuation member 1220 near the anterior side of the body, a posterior opening 1222 remains exposed. In some embodiments, the posterior opening 1222 is configured to receive an expansion instrument or tool that can expand or contract the height of the spacer 1210. In addition, the posterior opening 1222 is capable of advantageously receiving bone graft material therein, even when the fusion device 1210 has already been expanded, thereby maximizing the amount of bone graft material in the device.

FIG. 84A shows the expandable fusion device 1210 in a collapsed or unexpanded state. In the collapsed state, the device 1210 is capable of being delivered through a relatively small surgical opening to a desired anatomical location. To assist in delivering the device 1210 to a desired anatomical location, a surgeon can use an inserter tool to grasp the device 1210 along its sidewalls via inserter instrument recesses 1238.

Figure 85B:
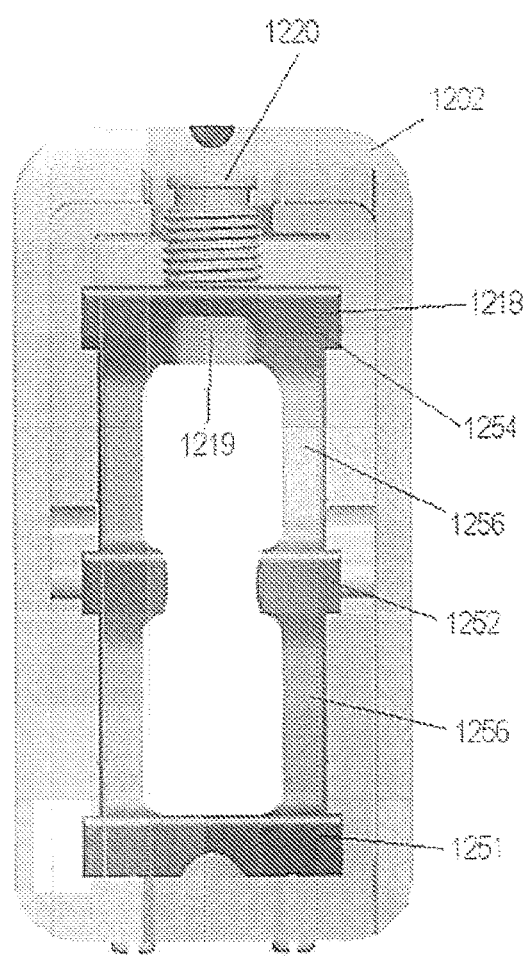

FIG. 84B shows the expandable fusion device 1210 in an extended or expanded state. To expand the device 1210, an expansion tool is inserted through the posterior opening 1222 and into the threaded actuation member 1220. The expansion tool can rotate the threaded actuation member 1220. As the actuation member 1220 is rotated in a first direction, the translation member 1220 (which threadingly engages the actuation member 1220), translates in a linear direction along the length of the actuation member 1220 (as shown in FIGS. 85A and 85B). As the translation member 1220 translates from an anterior-to-posterior direction, ramps 1251, 1252, 1254 of the translation member 1220 engage corresponding ramps on the endplates, thereby causing expansion of the device 1210. To reduce the height of the device 1210, the expansion tool can rotate the actuation member 1220 in a reversed second direction, thereby causing the translation member 1220 to translate from a posterior-to-anterior direction, and reduce the height of the device 1210.

FIGS. 85A and 85B are top views of the alternative expandable fusion device of FIG. 84A with endplates removed. From this view, one can see the actuation member 1220 screwed within the threaded engagement portion 1219 of the translation member 1218 according to some embodiments. The actuation member 1220 and the translation member 1218 both fit within the body 1202 of the fusion device 1210.

FIG. 85A shows the expandable fusion device 1210 in a collapsed state. From this view, one can see an anterior end of the translation member 1218 is adjacent the anterior wall of the body 1202. In some embodiments, the translation member 1218 is pressed against the anterior wall of the body 1202.

FIG. 85B shows the expandable fusion device 1210 in an expanded state. From this view, one can see how the translation member 1218 has translated in anterior-to-posterior direction, such that the anterior end of the translation member 1218 is removed away from the anterior wall of the body 1202. The translation member 1218 has shifted slightly in the posterior direction, such that upper and lower ramps of the translation member 1218 would engage corresponding ramps on the upper and lower endplates (not shown), thereby causing the expansion of the device.

Figure 86A:
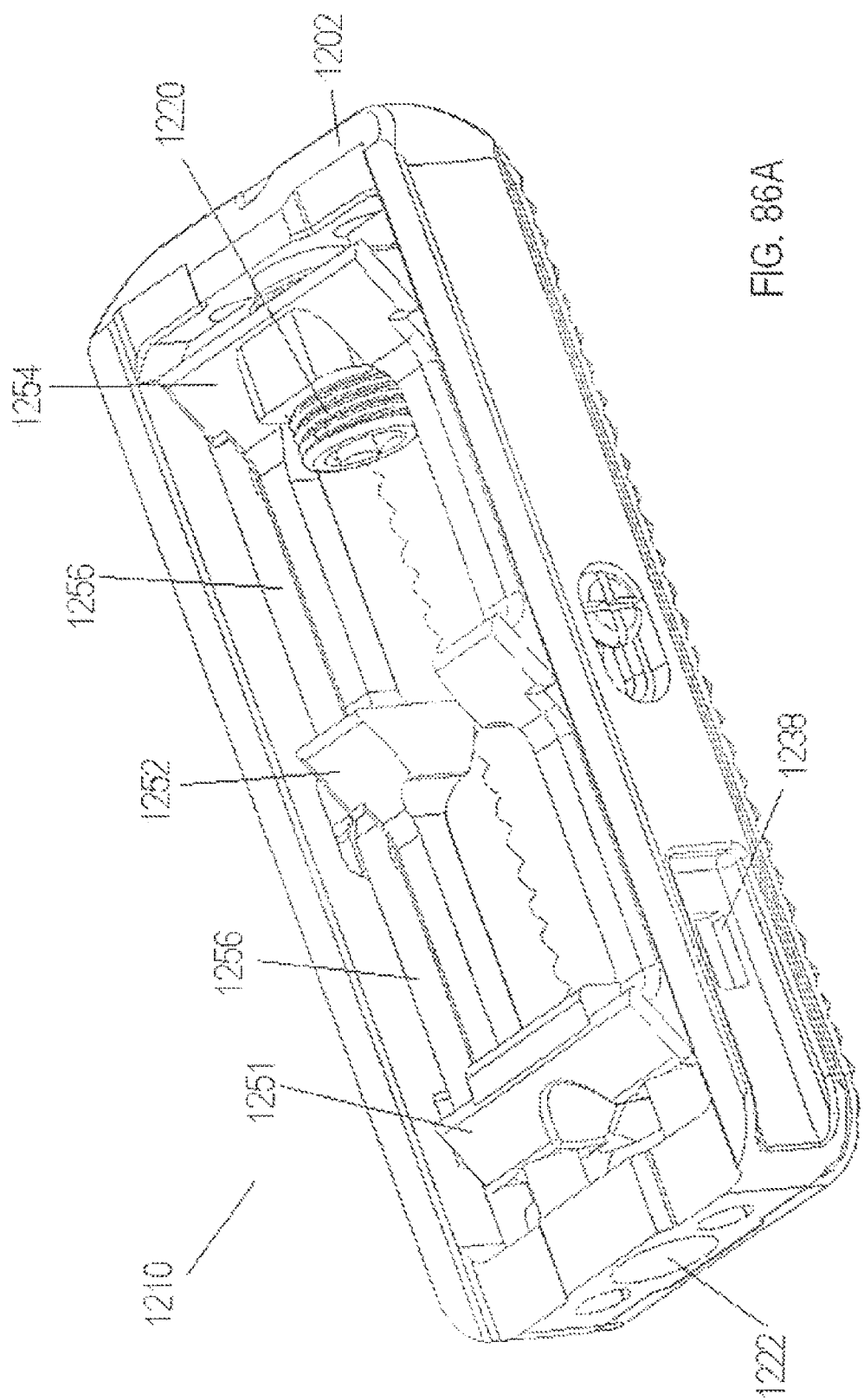
FIGS. 86A and 86B are top perspective views of the alternative expandable fusion device of FIG. 84A with endplates removed.
Figure 86B:
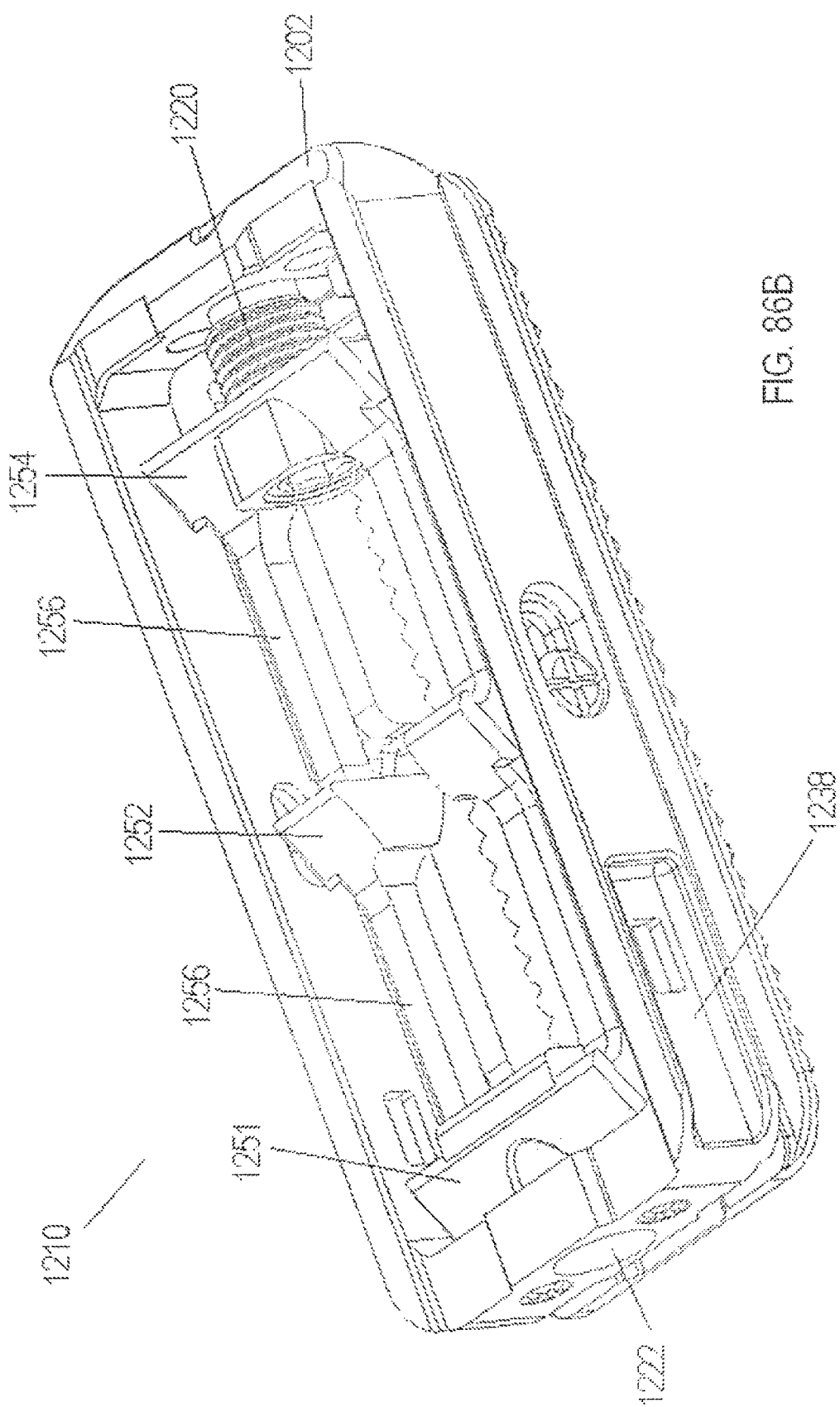

FIGS. 86A and 86B are top perspective views of the alternative expandable fusion device of FIG. 84A with endplates removed. In FIG. 86A, the fusion device 1210 is in a collapsed configuration, while in FIG. 86B, the fusion device 1210 is in an expanded configuration. From these views, one can see additional features not shown in FIGS. 85A and 85B, such as the side recess 1238 for receiving an insertion instrument.

In operation, the fusion device 1210 of FIGS. 84A-86B can be used as follows. A surgeon can deliver the fusion device 1210 in a collapsed configuration through an opening. The fusion device 1210 can be delivered into a desired anatomical space, whereby its tapered anterior end is a leading end. Once the fusion device 1210 is placed in a desired anatomical space, the surgeon can insert an expansion tool through a posterior opening 1222 in the body 1202 of the device 1210. The expansion tool can extend through the body 1202 and into the actuation member 1220, whereby it can rotate the actuation member 1220. Upon rotation of the actuation member 1220, the translation member 1218 translates in a posterior direction, such that its ramps engage with corresponding ramps of endplates. This translation of the translation member 1218 causes expansion of the fusion device 1210. Once the device 1210 has been properly expanded, the expansion tool can be removed from the posterior opening 1222, thereby leaving the posterior opening 1222 exposed. The surgeon can then insert bone graft material or other desirable materials into the posterior opening 1222 to assist in the proper fusion in the disc space.

Various mechanisms (shown in FIGS. 87A-102C) for providing lordotic expansion are now described below. These mechanisms can be used, for example, with the embodiments in FIGS. 72-83 to assist in providing lordotic expansion for the expandable devices. One skilled in the art will appreciate, however, that these mechanisms are not limited to those in FIGS. 72-83, and that any of the expandable implants shown above can benefit from these lordotic expansion mechanisms. For example, in some embodiments, an implant having an upper plate, lower plate, translation member having ramps and an actuation member can be provided with one of the lordotic mechanisms provided below in order to provide lordotic expansion. In some embodiments, an endplate can be angled in an anterior-posterior direction, such that either an anterior or posterior portion of the endplate is higher or lower than the opposite end. In other embodiments, an endplate can be angled in a side-to-side direction, such that either side of the endplate is higher or lower than the opposite end.

In FIGS. 87A-87C, an implant having a lordotic mechanism is provided comprising one or more rounded pivots that can slide back and forth and rotate in order to provide lordosis. The expandable implant 1310 comprises a first endplate 1314, a second endplate 1316, a graft opening 1349 through each of the first endplate and second endplate, and at least one rounded pivot mechanism. Like previous embodiments, the implant 1310 is configured to be placed in a disc space, whereby the first endplate 1314 can engage an upper vertebra and the second endplate 1316 can engage a lower vertebra. As shown in FIG. 87A, the implant 1310 comprises an upper rounded pivot 1322 and a lower rounded pivot 1324. In some embodiments, a single actuation member (e.g., the drive screw 1333) can rotate both the upper rounded pivot 1322 and the lower rounded pivot 1324. In other embodiments, each of the upper rounded pivot 1322 and the lower rounded pivot 1324 has its own actuation member for individual rotation. When the upper rounded pivot 1322 is rotated, this causes the upper rounded pivot 1322 to engage a contact surface of the first endplate 1314, thereby causing the first endplate 1314 to advantageously tilt and angle. Likewise, when the lower rounded pivot 1324 is rotated, this causes the lower rounded pivot 1324 to engage a contact surface of the second endplate 1316, thereby causing the second endplate 1316 to advantageously tilt and angle. Accordingly, these rounded pivots 1322, 1324 allow one side of an endplate to be higher than another side of an endplate, thereby better accommodating different anatomies.

Once a desired amount of lordosis, tilting or angulation is achieved by the rounded pivots 1322, 1324, a locking mechanism can be provided to lock the degree of lordosis. In some embodiments, each of the rounded pivots 1322, 1324 can include one or more lock wings 1330 that lock the degree of lordosis. In some embodiments, the lock wings 1330 can be hooks, grips or other protrusions that extend from the rounded pivots 1322, 1324 that prevent further rotation of the rounded pivots.

FIG. 87B shows a close-up view of a first endplate 1314 in accordance with some embodiments. The second endplate 1316 can include similar features. The endplate 1314 comprises an upper surface 1318, an opposing lower surface 1319, and a graft opening 1349 extending therethrough. The upper surface 1318 is configured to engage a vertebra while the lower surface 1319 provides a contact surface that engages the upper rounded pivot 1322. As shown in FIG. 87B, the first endplate 1314 is configured such that the upper surface 1318 and the lower surface 1319 are each curved. By having a curved lower surface 1319, the upper rounded pivot 1322 is capable of being nested within the opening created by the curvature of the curved lower surface 1319. The upper rounded pivot 1322 can be nested in the opening in a first configuration such that the first endplate 1314 is not tilted (as shown in FIG. 87A). If tilting is necessary, the upper rounded pivot 1322 can rotate, thereby causing the first endplate 1314 to angle.

FIG. 87C illustrates an alternate embodiment of a single-bodied rounded pivot 1326. In contrast to the embodiment in FIG. 87A that utilizes an upper rounded pivot 1322 and a lower rounded pivot 1324, FIG. 87C provides a single-bodied rounded pivot 1326 that can engage both the first endplate 1314 and the second endplate 1316. Advantageously, these rounded pivots can allow for lordotic expansion. In some embodiments, these rounded pivots can accommodate coronal and sagittal correction.

Figure 88A:
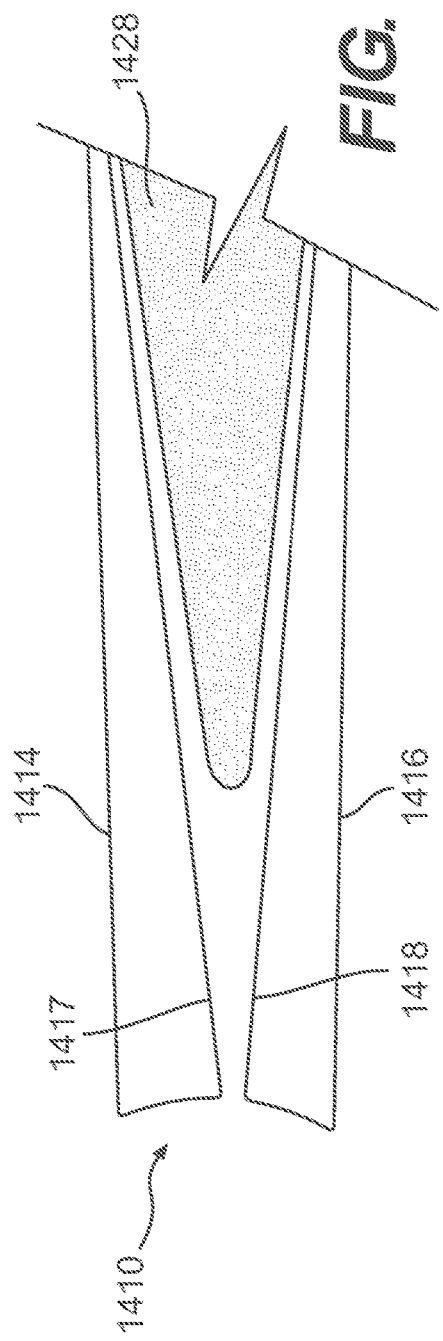
FIGS. 88A-88C are different views of different components of an alternate expandable fusion device having a ramped actuator for providing lordosis.
Figure 88C:
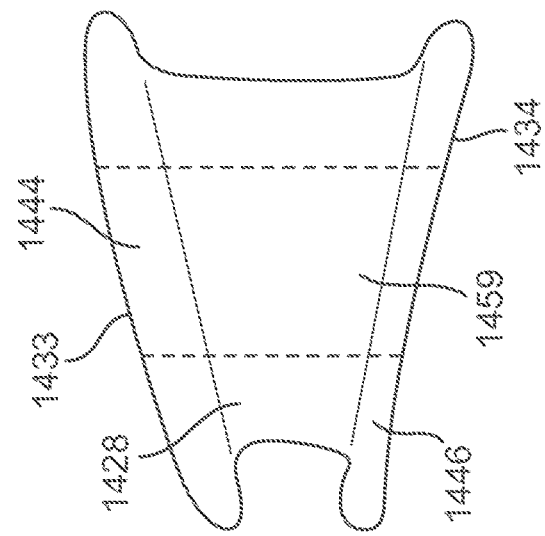
Figure 88B:
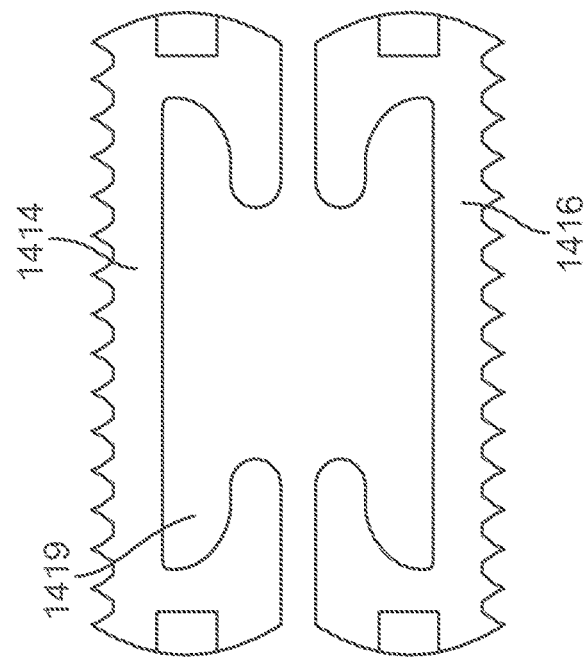

FIGS. 88A-88C illustrate different views of an alternate embodiment of an implant having a mechanism having a ramped actuator for providing lordotic expansion in accordance with some embodiments. As shown in FIG. 88A, the implant 1410 comprises a first endplate 1414, a second endplate 1416, and a ramped actuator 1428 positioned between the first endplate 1414 and the second endplate 1416. The ramped actuator 1428 is configured to have a ramped upper surface that engages a ramped lower surface of the first endplate 1414, as well as a ramped lower surface that engages a ramped upper surface of the second endplate 1416. As the ramped actuator 1428 translates linearly, this advantageously causes lordotic expansion of the implant.

FIG. 88B shows one embodiment of the opposing endplates 1414, 1416 in accordance with some embodiments. Each of the endplates can include one or more slots 1419 for receiving overhanging portions 1444, 1446 (shown in FIG. 88C) of the ramped actuator 1428. These slots 1419 advantageously serve as a guide for the ramped actuator 1428 as it linearly translates and causes lordotic expansion.

FIG. 88C shows one embodiment of the ramped actuator 1428 in accordance with some embodiments. The ramped actuator 1428 comprises an upper ramped surface 1433 configured to engage a lower ramped surface of the first endplate 1414 and a lower ramped surface 1434 configured to engage an upper ramped surface of the second endplate 1416. The upper ramped surface 1433 includes one or more overhangs 1444, while the lower ramped surface 1434 includes one or more overhangs 1446. These overhangs 1444, 1446 are received in slots 1419 formed in the first endplate 1414 and the second endplate 1416. In addition, as shown in FIG. 88C, the ramped actuator 1428 advantageously includes a hole or opening for receiving graft material therein.

Figure 89A:
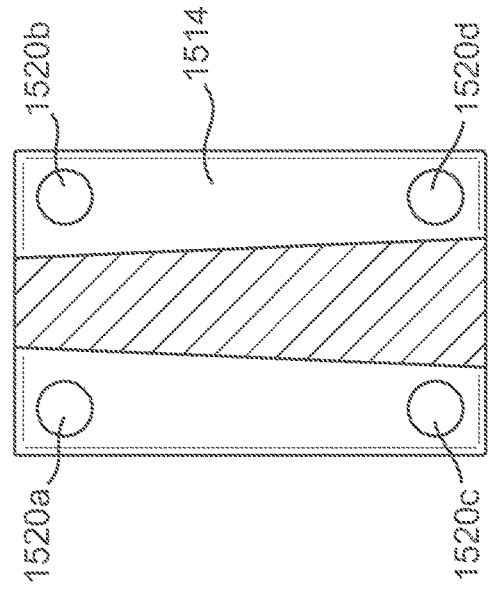
FIGS. 89A-89D are different views of different components of an alternate expandable fusion device having worm gears for providing lordosis.
Figure 89B:
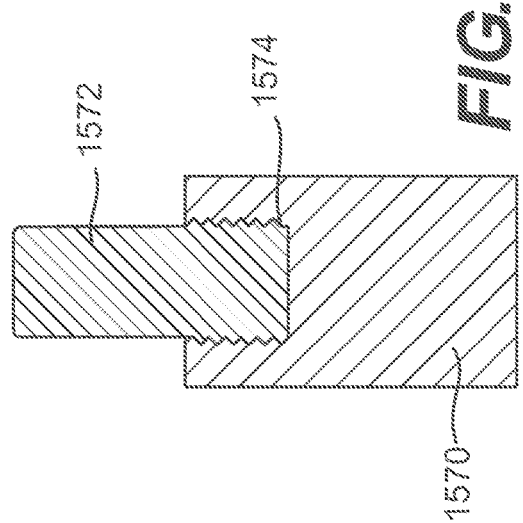

FIGS. 89A-89D are different views of different components of an alternate expandable fusion device having one or more worm gears for providing lordosis. As shown in FIG. 89A, the implant 1510 can comprise a first endplate 1514, a second endplate 1516, at least one worm gear 1520, and an actuator for the worm gear 1530. The one or more worm gears 1530 can be used to expand one portion (e.g., a corner) of the implant, thereby providing lordosis to the implant. As shown in FIG. 89B, in some embodiments, the implant 1510 can include four worm gears 1520a, 1520b, 1520c, and 1520d, wherein each is responsible for increasing the height or lordosis of one portion (e.g., a corner) of the implant.

Figure 89C:
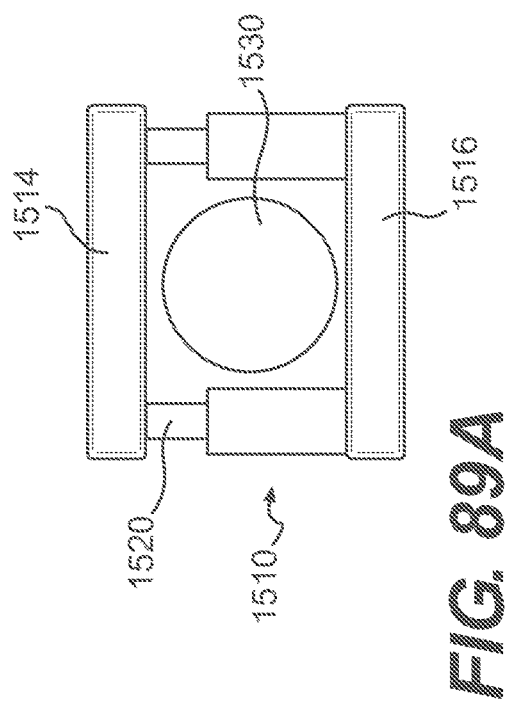
Figure 89D:
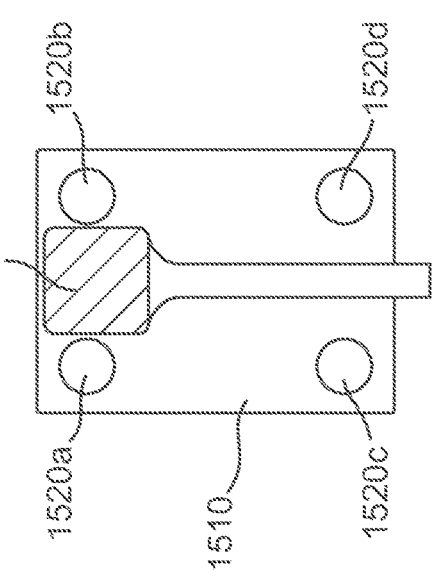

FIGS. 89C and 89D illustrate different embodiments of an instrument that engages the worm gears to provide lordosis to the implant. The instrument 1570 is capable of operating on a single worm gear at a time. FIG. 89D illustrates a distal end of the instrument 1570 that engages the worm gears. As shown in the figure, the distal end can include both endplate threads 1572 and worm gear threads 1574. Having dual threads advantageously allows the instrument 1570 to actuate different components. For example, the endplate threads 1572 can engage threads to cause the endplates to separate, while the worm gear threads 1574 can work specifically with threads of the worm gear to cause lordotic expansion.

FIGS. 90A-90C illustrate different embodiments of different components of an alternative expandable fusion device having moveable wedges for providing lordosis. The implant 1610 comprises an upper endplate 1614 and a lower endplate 1616. In between the upper and lower endplates are wedge members. As shown in FIG. 90A, the implant 1610 can include at least a first wedge member 1634 and a second wedge member 1636. The wedge members 1634, 1636 are attached to a shaft 1640. The wedge members 1634, 1636 are configured to have angled or ramped surfaces that cause lordotic expansion of the implant 1610. In some embodiments, the wedge members 1634, 1636 are configured to move at the same rate relative to one another. In another embodiment, the wedge members 1634, 1636 are configured to move at different rates relative to one another. In some embodiments, the shaft 1640 can include one type of thread correspond to wedge member 1634 and a second type of thread corresponding to wedge member 1636, such that the rate of translation of the wedge members differ from another. If one wedge members moves inwardly faster than another, this can cause lordotic expansion of the implant 1610.

FIG. 90C shows one embodiment of an implant 1610 having two sets of wedges: a first set of wedges 1634a, 1636a on a first shaft 1640a, and a second set of wedges 1634b, 1636b on a second shaft 1640b. Each of the wedges can be controlled by their own individual actuation nut 1647. This set of four wedges, each individually controlled, allows for any type of angling or lordotic expansion of the implant 1610. For example, if one desires lordotic expansion of one side of the implant (e.g., an anterior side), one can simply actuate wedges 1634a and 1634b. If one desires lordotic expansion of the other side of the implant (e.g., a posterior side), one can simply actuate the opposing wedges 1636a and 1636b.

FIGS. 91A-91D illustrate different views of an alternative expandable fusion device having an internal wedge mechanism for providing lordosis. The device 1710 comprises an upper endplate 1714 and a lower endplate 1716. In some embodiments, the upper endplate 1714 and the lower endplate 1716 can be separate from another, as in prior embodiments. In other embodiments, the upper endplate 1714 and the lower endplate 1716 are attached to one another via a hinge mechanism 1719 (as shown in FIG. 91A). As shown in FIG. 91A, an internal wedge 1730 can be received between the upper endplate 1714 and the lower endplate 1716. When the internal wedge 1730 rotates (as shown in FIG. 91B), it causes portions of the upper endplate 1714 to separate further away from the lower endplate 1716, thereby providing an implant with lordosis. FIG. 91A shows the internal wedge 1730 in a first reduced height configuration, while FIG. 91B shows the internal wedge 1730 in a second expanded height configuration. In some embodiments, the internal wedge 1730 can comprise a rotatable ramp mechanism that rotates via a keyed actuator.

FIGS. 91C and 91D show additional embodiments of an implant having an internal wedge mechanism to provide lordosis. From these views, one can see how the internal wedge 1730 can include an actuator 1734. In some embodiments, the actuator 1734 can receive an instrument that causes rotation of the internal wedge 1730, thereby changing its height and adjusting lordosis. In other embodiments, the actuator 1734 can receive an instrument that increases the height of the internal wedge 1730, thereby adjusting lordosis.

FIGS. 92A and 92B illustrate different views of an alternative expandable fusion device having linking members for providing lordosis. The implant 1810 comprises an upper endplate 1814 and a lower endplate 1816 separated by linking members. Linking members 1832 and 1834 work in associate with one another on one side of the implant, while linking members 1836 and 1838 work in associate with one another on an opposing side of the implant. Advantageously, the linking members enable each side of the implant to have a different degree of lordosis if desired.

Figure 93A:
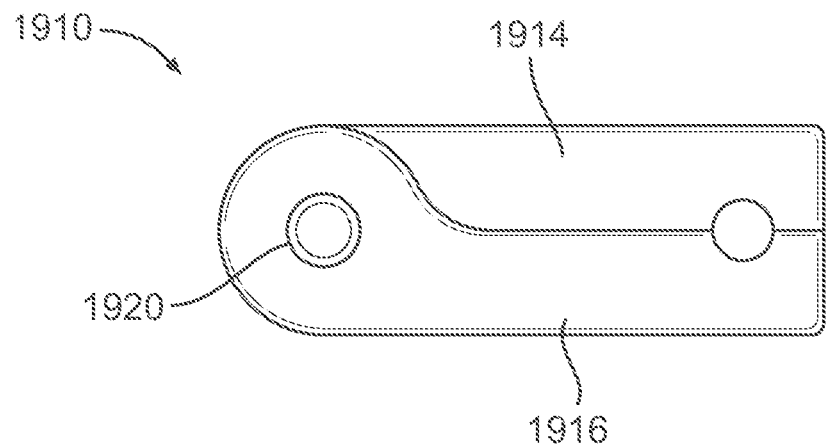
FIGS. 93A and 93B illustrate different views of an alternative expandable fusion device having a ramp wedge member for providing lordosis.
Figure 93B:
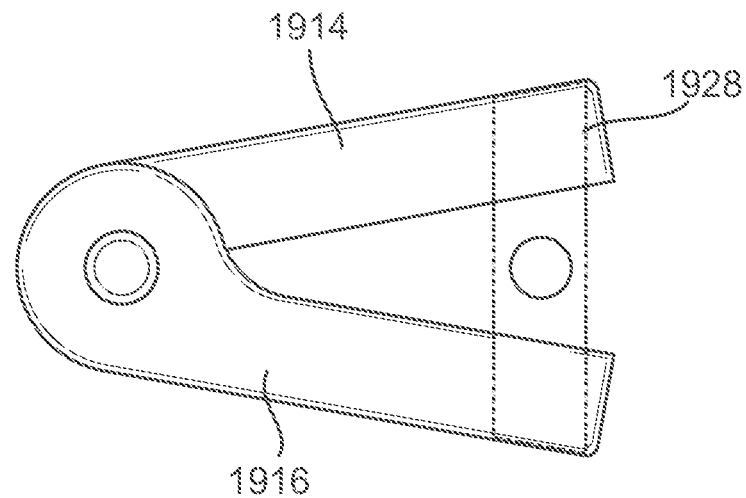

FIGS. 93A and 93B illustrate different views of an alternative expandable fusion device having a ramp wedge member for providing lordosis. The expandable fusion device 1910 includes a first endplate 1914 and a second endplate 1916. In some embodiments, the first endplate 1914 and the second endplate 1916 are independent of one another. In other embodiments, as shown in FIG. 93A, the first endplate 1914 is connected to the second endplate 1916 via a hinged member 1920. A ramped wedge member 1928 is inserted between the first endplate 1914 and the second endplate 1916, thereby causing lordotic expansion of the implant, as shown in FIG. 93B.

Figure 94A:
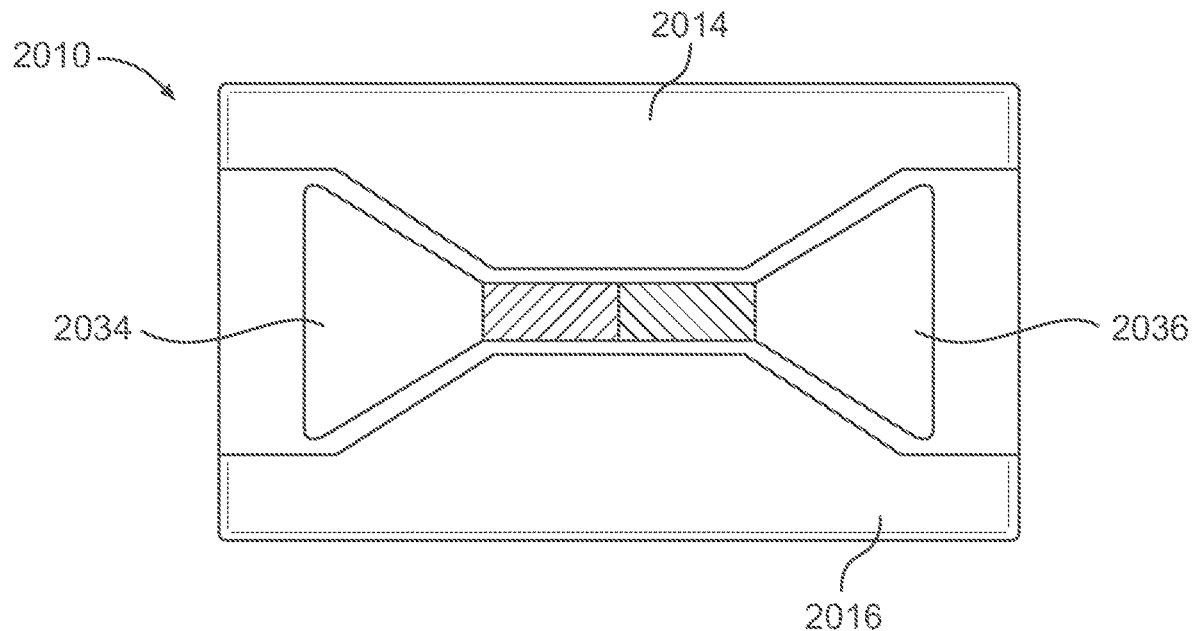
FIGS. 94A and 94B illustrates different embodiments of an implant having a lordotic expansion mechanism comprising tapered barrels.
Figure 94B:
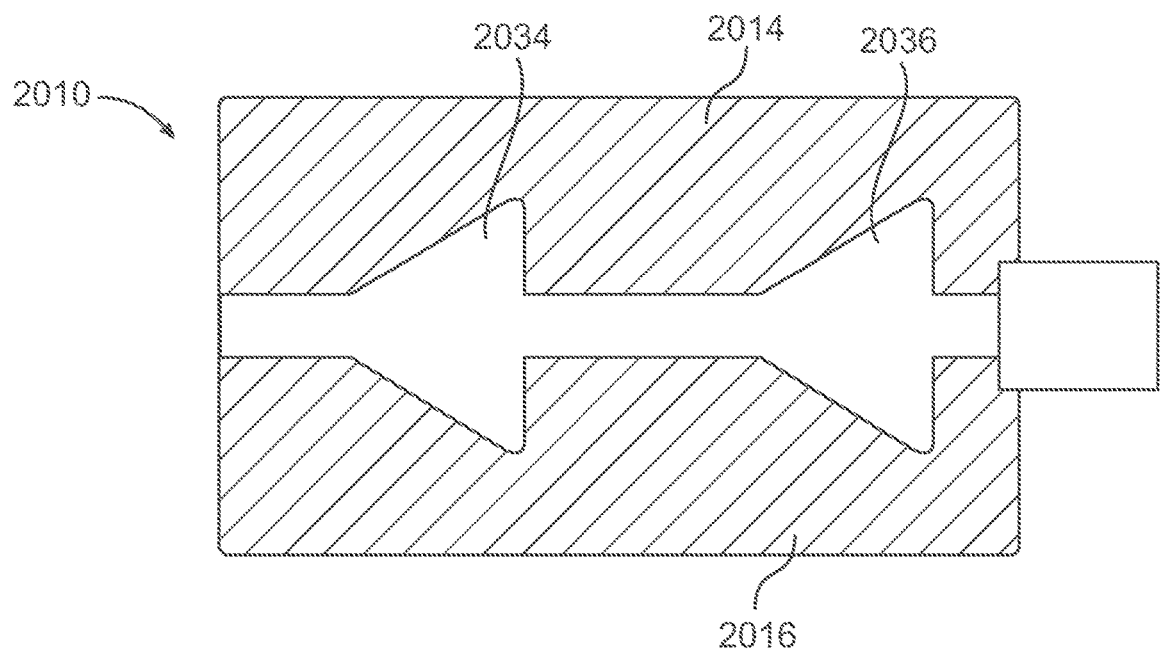

FIGS. 94A and 94B illustrate different embodiments of an implant having a lordotic expansion mechanism comprising tapered barrels. FIG. 94A illustrates an implant having an upper endplate 2014 and a lower endplate 2016. A first tapered barrel 2034 and a second tapered barrel 2036 are positioned on a shaft 2040 in between the upper endplate and the lower endplate. Like the wedge members in FIG. 90A, the tapered barrels 2034 and 2036 are capable of independently moving from one another, thereby causing lordosis of the implant.

FIG. 94B illustrates an alternative embodiment of an implant having tapered barrels. As opposed to the embodiment in FIG. 94A, in which the tapered barrels 2034, 2036 faced in different directions, the tapered barrels 2034, 2036 in FIG. 94B face in the same direction on the shaft 2040. In some embodiments, each of the tapered barrels 2034, 2036 can be independently controlled to cause a desired amount of angling or lordotic expansion of the upper and/or lower endplates.

Figure 95B:
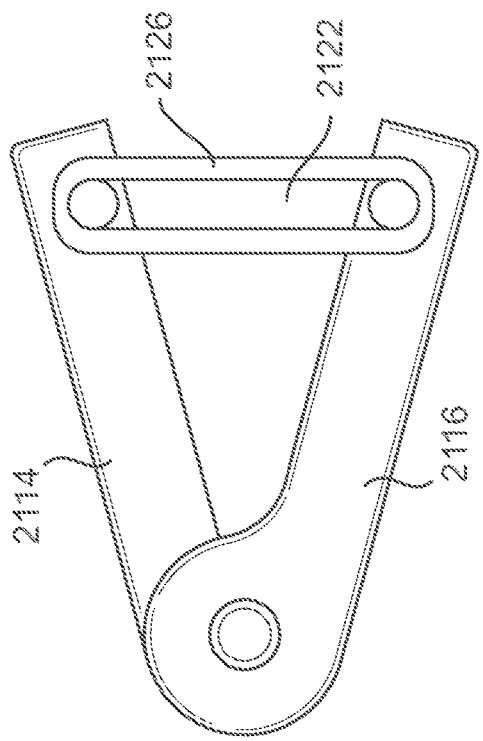
FIGS. 95A-95C illustrate different views of different components of an implant having a lordotic expansion mechanism comprising a serrated plate.
Figure 95C:
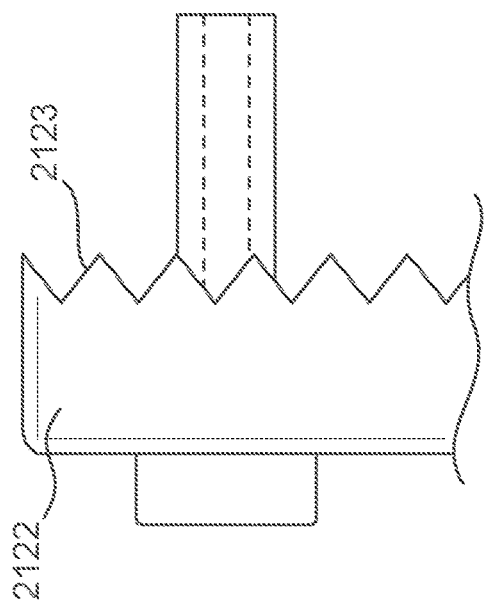
Figure 95A:
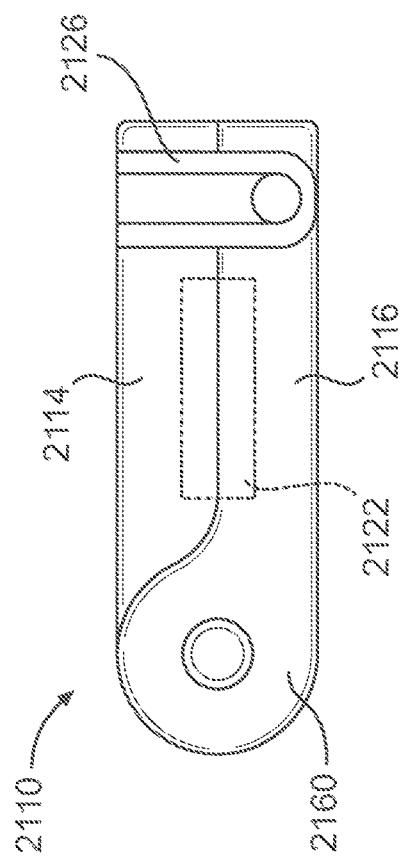

FIGS. 95A-95C illustrate different views of different components of an implant having a lordotic expansion mechanism comprising a serrated plate. The implant 2110 comprises a first endplate 2114 and a second endplate 2116. While in some embodiments, the first endplate 2114 and the second endplate 2116 are independent from one another, in the present embodiment (as shown in FIG. 95A), the first endplate 2114 is connected via a hinged portion 2160 to the second endplate 2116. In an opposite end of the implant 2110, a ratchet plate 2126 is provided having ratchet members or teeth. In between the first endplate 2114 and the second endplate 2116 is a serrated plate 2122.

FIG. 95A shows a first configuration in which the serrated plate 2122 is lay sideways or flat, while FIG. 95B shows a second configuration in which the serrated plate 2122 is propped upwards to cause lordosis of the implant. An instrument (e.g., an actuator) can be used to prop the serrated plate 2122 upwards into the second configuration. When the serrated plate 2122 is brought upwards, its serrations or teeth can engage the teeth of the ratchet plate 2126, thereby creating a ratchet mechanism for controlling the lordotic height of the implant.

FIGS. 96A-96C show different views of an implant having a lordotic expansion mechanism comprising threaded barrels. The implant 2210 comprises an upper endplate 2214 and a lower endplate 2216. Positioned in between the endplates are threaded barrels 2232 and 2234 positioned on a shaft 2240. Each of the threaded barrels 2232, 2234 are movable along the shaft to cause lordosis of the implant. Advantageously, the threaded barrels 2232, 2234 have threads that engage corresponding threads on the endplates. The threads on the threaded barrels 2232, 2234 advantageously provide controlled, gradual lordotic expansion of the implant. As shown in FIG. 96B, a single implant 2210 can include multiple thread barrels (e.g., four threaded barrels 2032, 2034, 2036, 2038) thereby providing lordotic expansion on different portions (e.g., different corners) of the implant.

Figure 97:
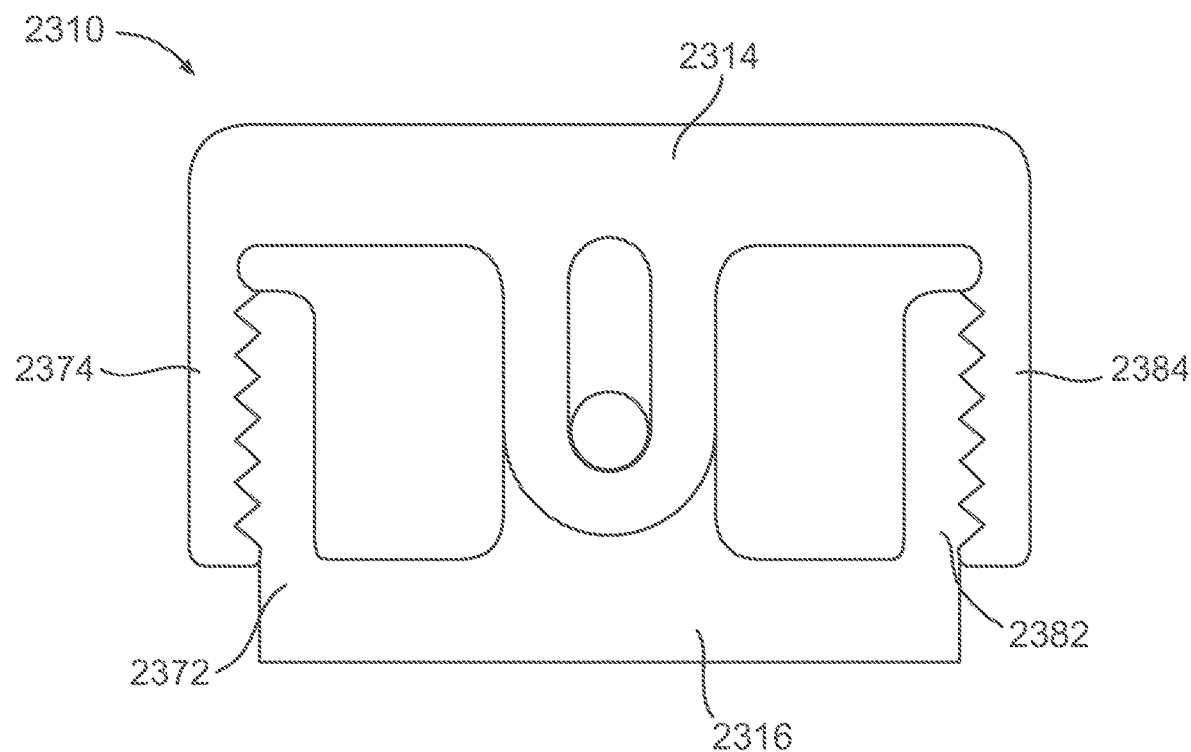
FIG. 97 show a different embodiment of an implant comprising one or more ratcheting mechanisms for lordotic expansion.

FIG. 97 show a different embodiment of an implant comprising one or more ratcheting mechanisms for lordotic expansion. In the present embodiment, the implant 2310 includes an upper endplate 2314 and a lower endplate 2316. The upper endplate 2314 includes a downwardly facing first arm 2374 having ratcheting teeth and a downwardly facing second arm 2384 having ratcheting teeth. The lower endplate 2316 includes an upwardly facing first arm 2372 having ratcheting teeth and an upwardly facing second arm 2382 having ratcheting teeth. In some embodiments, the first arm 2374 of the upper endplate 2314 engages the first arm 2372 of the lower endplate, while the second arm 2372 of the upper endplate 2314 engages the second arm 2382 of the second endplate, thereby creating two pairs of ratcheting mechanisms. Each pair of ratcheting mechanism advantageously allows one side of the implant to be angled relative to another, thereby providing desirable lordotic expansion.

FIGS. 98A-98C show different views of an implant including a height changing wedge that provides lordosis and expansion. The implant 2410 comprises an upper endplate 2414 and a lower endplate 2416 separated by a first wedge 2432 and a second wedge 2434. As shown in FIG. 98A, the first wedge 2432 and the second wedge 2434 can be at a substantially equal height such that the upper endplate 2414 and the lower endplate 2416 are substantially parallel to one another. As shown in FIG. 98B, the first wedge 2432 has been expanded to a different height, thereby creating an implant having variable lordosis and expansion. As shown in FIG. 98C, both the first wedge 2432 and the second wedge 2434 include their own individual drive mechanism for modifying their specific height. First wedge 2432 includes drive screw 2445, while second wedge 2445 includes its own drive screw 2446. These drive screws 2445, 2446 provide an infinite number of height changes and combinations between the first wedge 2432 and the second wedge 2445, thereby providing variable lordosis in the implant.

FIGS. 99A-99C show different views of an implant having a driving wedge for providing lordotic expansion. The implant 2510 comprises an upper endplate 2514 and a lower endplate 2516 that are expandable away from one another. In some embodiments, the upper endplate 2514 and the lower endplate 2516 are detached from one another. In other embodiments, as shown in FIG. 99A, the upper endplate 2514 is attached to the lower endplate 2516 via a hinge 2519. In between the upper endplate 2514 and lower endplate 2516 is a driving wedge 2532. The driving wedge 2532 can be linearly translated (e.g., along a track or grooves formed in the upper and lower endplates) to thereby cause separation of the endplates. As the endplates are connected via a hinge 2519, the hinged portion will have a height that is less than the expanded portion, thereby creating an implant with lordotic expansion, as shown in FIG. 99B. FIG. 99C shows a top view of the implant 2510, which includes a graft window 2440 for receiving graft material therein.

Figure 100A:
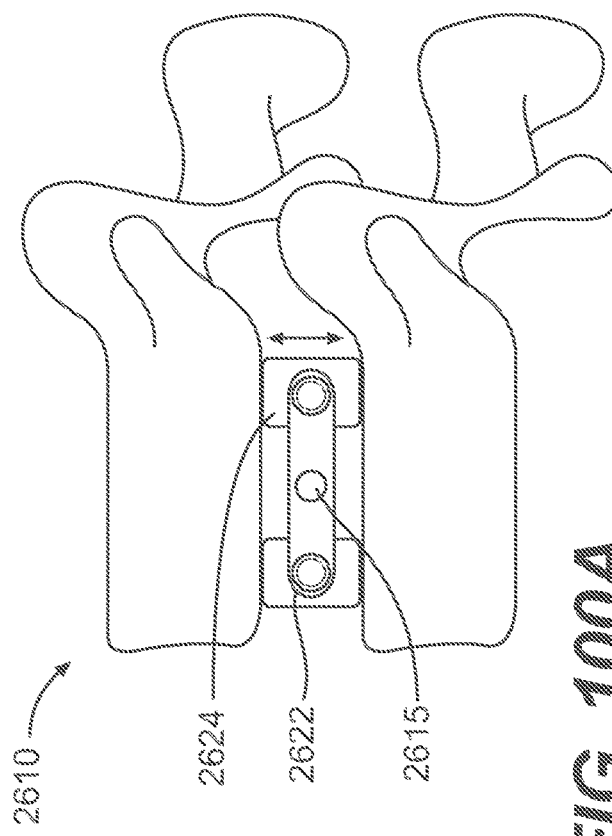
FIGS. 100A-100C show different views of different components of an implant having connectable side portions for providing lordotic expansion.
Figure 100B:
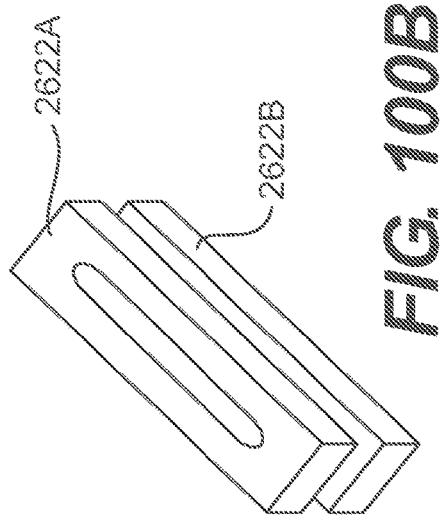
Figure 100C:
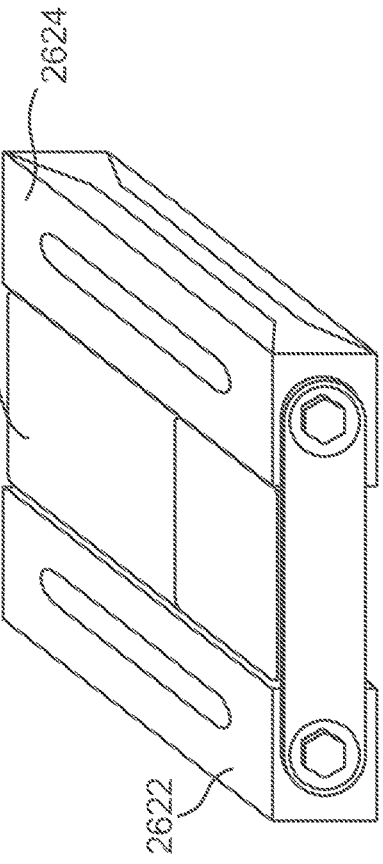

FIGS. 100A-100C show different views of different components of an implant having connectable side portions for providing lordotic expansion. The implant 2610 comprises a body 2615 having a first connectable side portion 2622 and a second connectable side portion 2624 for providing height changes and lordotic expansion. In some embodiments, the body and connectable side portions form the implant that is inserted into a disc space. In other embodiments, the body and connectable side portions are received between endplates to be inserted into a disc space. In some embodiments, the body 2615 can be static in height, while in other embodiments, the body 2615 can be expandable.

FIG. 100B shows a close-up view of a connectable side portion in accordance with some embodiments. The connectable side portion 2622 comprises an upper layer 2622A that is spaced from a lower layer 2622B. In some embodiments (as shown in FIG. 100A), the two layers are connected. In other embodiments, the upper layer 2622A is detached from the lower layer 2622B.

Figure 101:
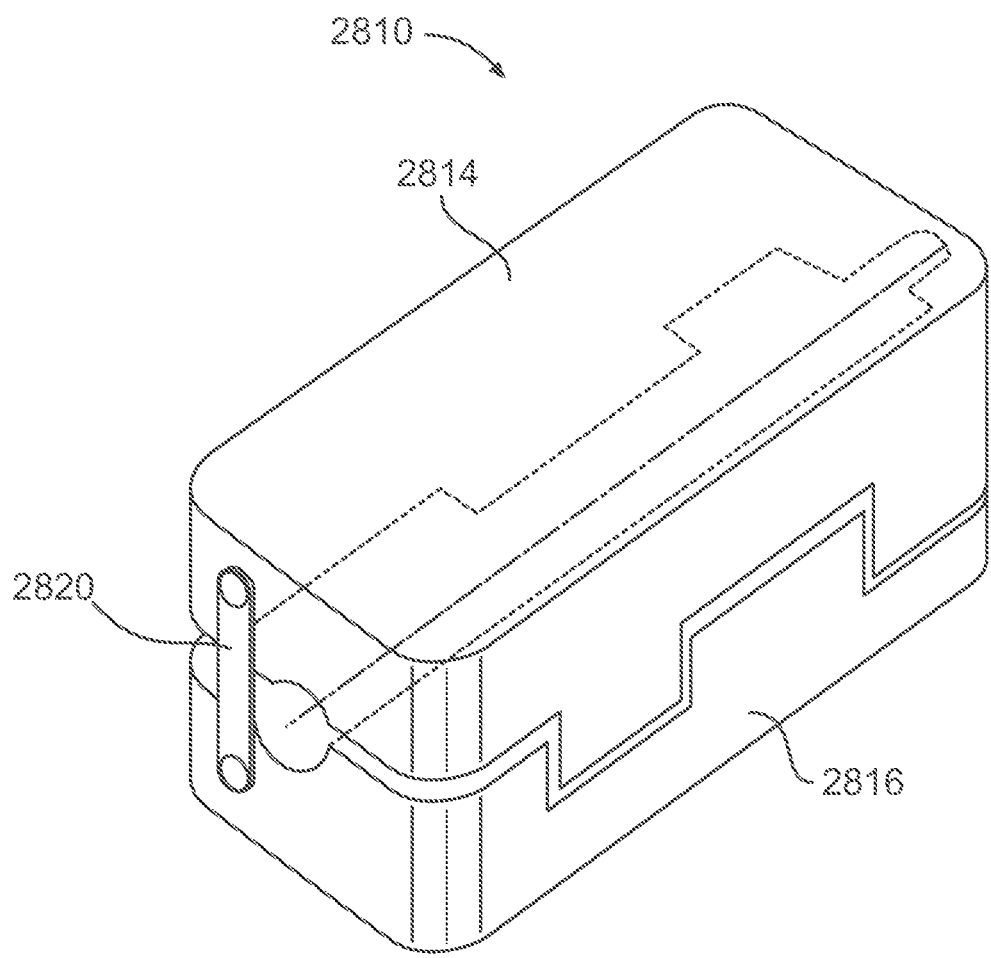
FIG. 101 shows a locking mechanism for maintaining an expansion height in accordance with some embodiments.

For each of the embodiments described above, it may be useful to maintain the expanded height of the implant. FIG. 101 shows an implant 2810 having an expandable upper endplate 2814, a lower endplate 2816 and a ratcheting lock mechanism 2820 that can be used to secure the height expansion between the two endplates. The ratcheting lock mechanism 2820 can include teeth (e.g., ratchet teeth) that are designed to mate with other teeth (e.g., found on an endplate) to thereby secure the height expansion of the implant.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An intervertebral implantation system comprising:
 a housing body having an anterior end, a posterior end, an anterior wall comprising an anterior opening, a posterior wall comprising a posterior opening, a first side wall connecting the anterior wall and the posterior wall, and a second side wall disposed on an opposite side of the first side wall and connecting the anterior wall and the posterior wall, each of the first and second side walls having an elongate slot;
 a first endplate received in the housing body in an unexpanded state;
 a translator received in the housing body and slidably coupled to the first endplate, the translator including first and second angled portions configured to slidably engage the first endplate, and a bridge disposed between the first and second angled portions;
 an actuator received in the posterior end of the housing body and operably attached to the translator; and a pair of laterally extending pins that are received in the elongate slots of the first and second side walls and threaded into the translator, wherein movement of the actuator causes translation of the translator which causes the first and second angled portions to push against the first endplate to vertically raise the first endplate to transition the first endplate to an expanded state.

2. The intervertebral implantation system of claim 1, wherein: the elongate slot is elongate in a longitudinal direction between the anterior and posterior ends of the housing body; the first side wall and the second side wall each include a posterior recess for attachment to an insertion instrument; the first endplate includes a plurality of openings for receiving bone graft material; and the first endplate includes a plurality of teeth for gripping a vertebral body.

3. The intervertebral implantation system of claim 1, wherein the elongate slot is elongate in a longitudinal direction between the anterior and posterior ends of the housing body.

4. The intervertebral implantation system of claim 1, wherein the first side wall and the second side wall each include a posterior recess for receiving an insertion instrument therein.

5. The intervertebral implantation system of claim 1, wherein the first endplate includes a plurality of openings for receiving graft material and a plurality of projections for gripping a vertebral body.

6. The intervertebral implantation system of claim 1, wherein the translator includes a posterior central opening through which an insertion instrument is configured to be received.

7. An intervertebral implantation system comprising:
a housing body having an anterior wall defining an anterior end, the anterior wall comprising an anterior opening, a posterior wall defining a posterior end, the posterior wall comprising a posterior opening, a first side wall connecting the anterior wall and the posterior wall, and a second side wall disposed on an opposite side of the first side wall and connecting the anterior wall and the posterior wall, each of the first and second side walls having an elongate slot;
a first endplate received in the housing body and having a first opening configured to receive bone graft material;
a second endplate disposed on an opposite side of the first endplate and having a second opening configured to receive bone graft material;
a translator received in the housing body between the first and second endplates and slidably coupled to the first endplate, the translator including first and second angled portions configured to slidably engage the first endplate, and a bridge disposed between the first and second angled portions;
an actuator received in the posterior end of the housing body and operably attached to the translator; and
a pair of laterally extending pins that are received in the elongate slots of the first and second side walls and threaded into the translator,
wherein movement of the actuator causes translation of the translator which causes the first and second angled portions to push against an underside of the first endplate to vertically raise the first endplate to transition the first endplate to an expanded.

8. The intervertebral implantation system of claim 7, wherein: the elongate slot is elongate in a longitudinal direction between the anterior and posterior ends of the housing body; the first side wall and the second side wall each include a posterior recess for attachment to an insertion instrument; and the first endplate includes a plurality of teeth for gripping a vertebral body.

9. The intervertebral implantation system of claim 7, wherein the first side wall and the second side wall each include a posterior recess for receiving an insertion instrument therein.

10. The intervertebral implantation system of claim 7, wherein the translator includes a posterior central opening through which an insertion instrument is configured to be received.

11. The intervertebral implantation system of claim 7, wherein the underside of the first endplate comprises a dovetail groove for receiving each of the first and second angled portions of the translator.

12. A method for stabilizing spinal vertebrae comprising the steps of:
providing an intervertebral implantation system comprising:
a housing body having an anterior end, a posterior end, an anterior wall comprising an anterior opening, a posterior wall comprising a posterior opening, a first side wall connecting the anterior wall and the posterior wall, and a second side wall disposed on an opposite side of the first side wall and connecting the anterior wall and the posterior wall, each of the first and second side walls having an elongate slot;
a first endplate received in the housing body in an unexpanded state;
a translator received in the housing body and slidably coupled to the first endplate, the translator including first and second angled portions configured to slidably engage the first endplate, and a bridge disposed between the first and second angled portions;
an actuator received in the posterior end of the housing body and operably attached to the translator; and
a pair of laterally extending pins that are received in the elongate slots of the first and second side walls and threaded into the translator,
wherein movement of the actuator causes translation of the translator which causes the first and second angled portions to push against the first endplate to vertically raise the first endplate to transition the first endplate to an expanded state; and
positioning the intervertebral implantation system between adjacent vertebral bodies; and
expanding the intervertebral implantation system to stabilize the adjacent vertebral bodies.

13. The method of claim 12, wherein: the elongate slot is elongate in a longitudinal direction between the anterior and posterior ends of the housing body; the first side wall and the second side wall each include a posterior recess for attachment to an insertion instrument; the first endplate includes a plurality of openings for receiving bone graft material; and the first endplate includes a plurality of teeth for gripping a vertebral body.

14. The method of claim 12, wherein the elongate slot is elongate in a longitudinal direction between the anterior and posterior ends of the housing body.

15. The method of claim 12, wherein the first side wall and the second side wall each include a posterior recess for receiving an insertion instrument therein.

16. The method of claim 12, wherein the first endplate includes a plurality of openings for receiving graft material and a plurality of projections for gripping a vertebral body.

17. The method of claim 12, wherein the translator includes a posterior central opening through which an insertion instrument is configured to be received.

\* \* \* \* \*